US007071293B1

(12) United States Patent
Tack et al.

(10) Patent No.: US 7,071,293 B1
(45) Date of Patent: Jul. 4, 2006

(54) ALPHA HELICAL PEPTIDES WITH BROAD SPECTRUM ANTIMICROBIAL ACTIVITY THAT ARE INSENSITIVE TO SALT

(75) Inventors: Brian F. Tack, Iowa City, IA (US); Paul B. McCray, Jr., Iowa City, IA (US); Michael Welsh, Riverside, IA (US); Sue M. Travis, Iowa City, IA (US); Robert Lehrer, Santa Monica, CA (US)

(73) Assignees: The University of Iowa Research Foundation, Iowa City, IA (US); The Regents of the University of California, Oakland, CA (US)

( * ) Notice: Subject to any disclaimer, the term of this patent is extended or adjusted under 35 U.S.C. 154(b) by 46 days.

(21) Appl. No.: 09/642,744

(22) Filed: Aug. 18, 2000

Related U.S. Application Data

(60) Provisional application No. 60/149,886, filed on Aug. 18, 1999.

(51) Int. Cl.
| | |
|---|---|
| A61K 38/00 | (2006.01) |
| A61K 38/04 | (2006.01) |
| C07K 14/00 | (2006.01) |
| C07K 16/00 | (2006.01) |
| C07K 17/00 | (2006.01) |
| C07K 5/00 | (2006.01) |
| C07K 7/00 | (2006.01) |

(52) U.S. Cl. .................. 530/300; 530/324; 530/325; 530/326; 530/327; 514/12
(58) Field of Classification Search .................. 514/12; 530/300; 536/23.1; 435/32, 4; 424/9.1
See application file for complete search history.

(56) References Cited

U.S. PATENT DOCUMENTS

| 5,618,675 | A * | 4/1997 | Larrick et al. ............... 435/7.1 |
| 6,103,888 | A * | 8/2000 | Larrick et al. ............. 536/23.5 |
| 6,492,328 | B1 * | 12/2002 | Lehrer et al. ................. 514/2 |
| 6,809,181 | B1 * | 10/2004 | McCray et al. ............ 530/350 |
| 2002/0082195 | A1 * | 6/2002 | Lehrer et al. ................. 514/2 |
| 2003/0022829 | A1 * | 1/2003 | Maury et al. ................ 514/12 |
| 2003/0054422 | A1 * | 3/2003 | Badley et al. ............. 435/7.32 |
| 2003/0143234 | A1 * | 7/2003 | Shi et al. ................. 424/178.1 |
| 2004/0086535 | A1 * | 5/2004 | Maury et al. ............. 424/278.1 |
| 2004/0137482 | A1 * | 7/2004 | Eckert et al. ................. 435/6 |
| 2005/0124064 | A1 * | 6/2005 | Schnorr et al. ............. 435/386 |
| 2005/0239709 | A1 * | 10/2005 | Hogenhaug ................. 514/13 |
| 2005/0250699 | A1 * | 11/2005 | Hogenhaug et al. .......... 514/13 |
| 2005/0277176 | A1 * | 12/2005 | McCray et al. ............ 435/69.1 |

FOREIGN PATENT DOCUMENTS

| EP | 1359930 A2 * | 9/2004 |
| WO | WO 94/02589 * | 2/1994 |

OTHER PUBLICATIONS

Turner et al.,Antimicrobial and Chemotherapy vol. 42, No. 9, pp. 2206-2214, 1998..*
Tossi et al. , FEBS Letters vol. 339, pp. 108-112, 1994..*
Merluzzi et al.,Peptides, vol. 261, pp. 639-640, 1996.*
Bagella et al., FEBS Letters, vol. 376, pp. 225-228, 1995.*
Mahoney et al., FEBS Letters, vol. 377, pp. 519-522, 1995.*
Sequence alignments for SEQ ID No. 27.*
Sequence Alignment # AAR45671.*
Larrick et al. Infection and Immunity, vol. 63, No. 4, pp. 1291-1297, 1995.*
Sequence alignment Accession No. JQ1171.*
Bagella et al., "cDNA sequences of three sheep myeloid cathelicidins," *FEBS Lett.*, 376:225-228, 1995.
Boman, "Peptide antibiotics and their role in innate immunity," *Annu. Rev. Immunol.*, 13:61-92, 1995.
Gallo et al., "Antimicrobial peptides: an emerging concept in cutaneous biology," *J Invest Dermatol.*, 111(5):739-43, 1998.
Ganz and Lehrer, "Antimicrobial peptides of vertebrates," *Current Opinions Immun,.* 10:41-44, 1998.
Gennaro and Zanetti, "Structural features and biological activities of the cathelicidin-derived antimicrobial peptides," *Bipoly*, 55:31-49, 2000.
Hirata, et al., "Characterization of a rabbit cationic protein (CAP18) with lipopolysaccharide-inhibitory activity," *Infect. Immun.* 62 (4), 1421-1426 (1994).
Hwang et al., "Structure-function relationships of antimicrobial peptides," *Biochem Cell Biol*, 76(2-3):235-46, 1998.
Mahoney et al., "Molecular analysis of the sheep cathelin family reveals a novel antimicrobial peptide," *FEBS Lett*, 377:519-522, 1995.
Oren et al., "Mode of action of linear amphipathic α-helical antimicrobial peptides," *Biopolymers*, 47(6):451-63, 1998.
Russell et al., "Coordinate induction fo two antibiotic genes in tracheal epithelial cells exposed to the inflammatory mediators lipopolysaccharide and tumor necrosis factor alpha," *Infect Immun*, 64(5):1565-8, 1996.
Skerlavaj et al., "SMAP-29: a potent antibacterial and antifungal peptide from sheep leukocytes," *FEBS Letters*, 463:58-62, 1999.

(Continued)

Primary Examiner—N. M. Minnifield
(74) Attorney, Agent, or Firm—Fulbright & Jaworski

(57) ABSTRACT

The present invention relates to the use of antimicrobial peptides in the inhibition of microbial growth and proliferation. Novel antimicrobial truncated peptides are disclosed which are based upon SMAP 29 and RCAP 18, but which contain a lesser number of amino acid residues yet still retain bactericidal activity. In addition, synthetic peptides based upon the SMAP 29 protein are disclosed which have fewer amino acid residues and include substitutions yet retain substantial activity. The invention also relates to a method of inhibiting microbial growth by administering an effective amount of a peptide in accordance with the invention, or by combining the peptides with other antimicrobial agents or antibiotics.

21 Claims, 21 Drawing Sheets

OTHER PUBLICATIONS

Bals et al., "The peptide antibiotic LL-37/hCAP-18 is expressed in epithelia of the human lung where it has broad antimicrobial activity at the airway surface," *Proc. Natl., Acad. Sci. USA*, 95:9541-9546, 1998.

Huttner et al., "Localization and genomic organization of sheep antimicrobial peptide genes," *Gene*, 206:85-91, 1998.

Merluzzi et al., "Biological Activity of a navel, cathelicidin-derived antimicrobial peptide from sheep," *Peptides*, 261:639-640, 1996.

Tossi et al., "Design of synthetic antimicrobial peptides based on sequence analogy and amphipathicity," *Eur. J. Biochem.*, 250:549-558, 1997.

Tossi et al., "Identification and characterization of a primary antibacterial domain in CAP 18, a lipopolysaccharide binding protein from rabbit leukocytes," *FEBS Letters*, 339:108-112, 1994.

Travis et al., "Bactericidal activity of mammalian cathelicidin-derived peptides," *Infection and Immunity*, 68:2748-2755, 2000.

* cited by examiner

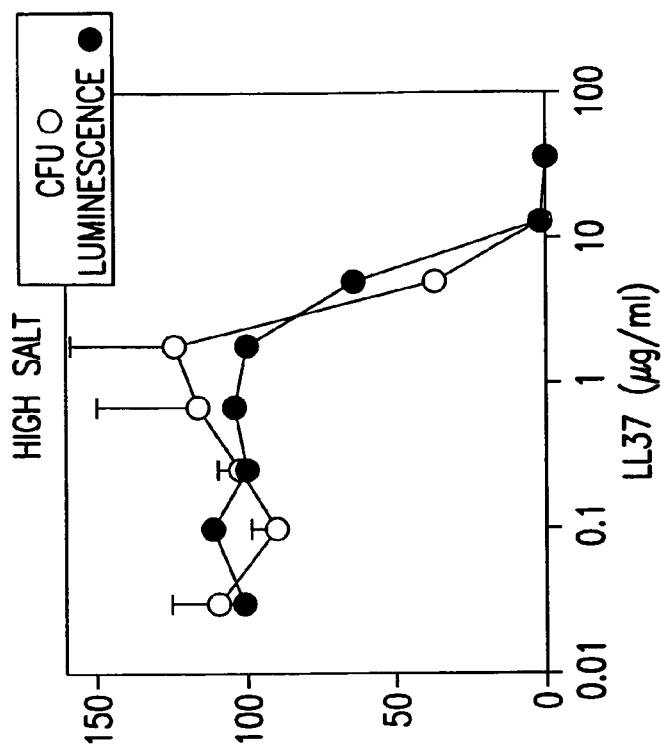
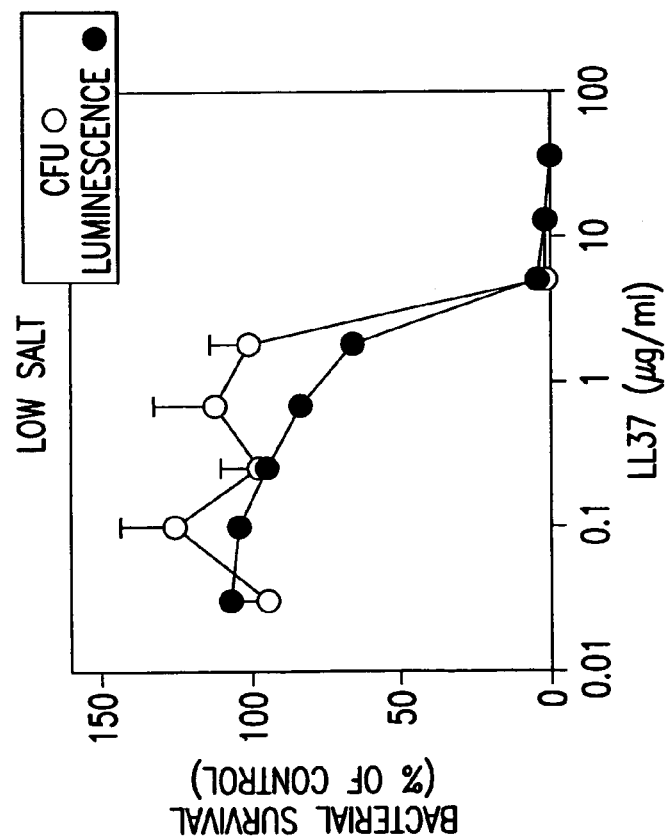

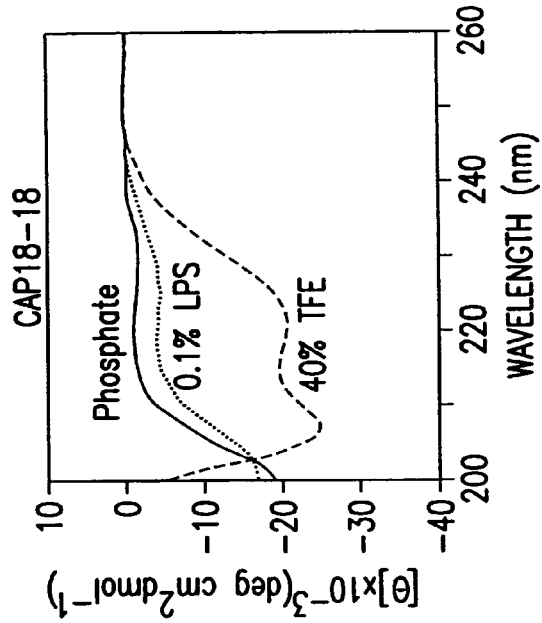
FIG. 3A-2
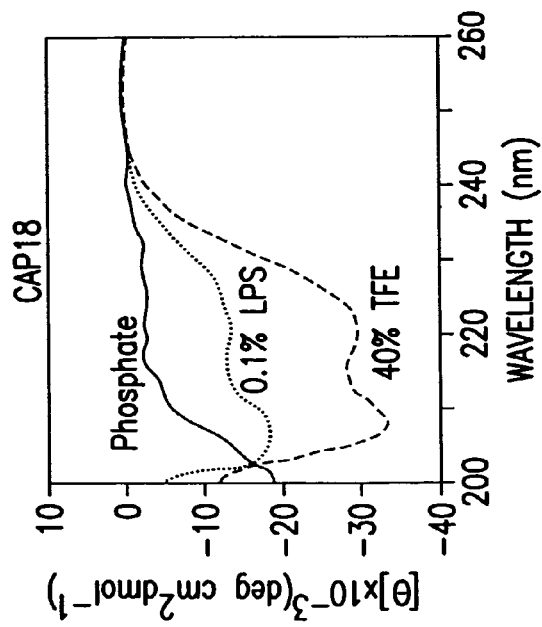
FIG. 3A-1
| | Pi | 0.1% LPS | 40% TFE |
|---|---|---|---|
| CAP18 | 8.1 | 39.2 | 84.6 |
| CAP18-21a | 7.7 | 19.2 | 97.0 |
| CAP18-18 | 3.8 | 13.4 | 64.8 |
| CAP18-17 | 3.1 | 14.6 | 68.8 |
| CAP18-15a | 2.7 | 11.5 | 44.7 |
FIG. 3A-3

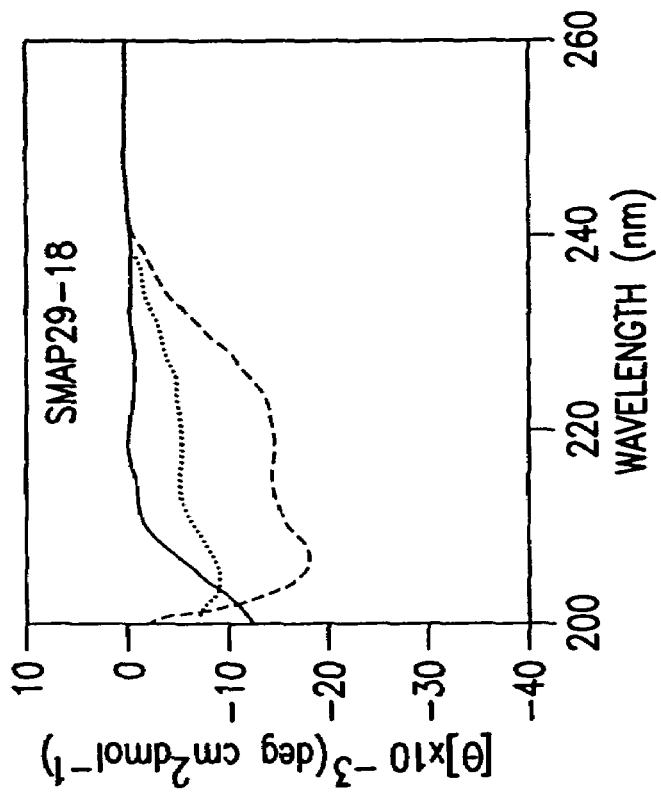
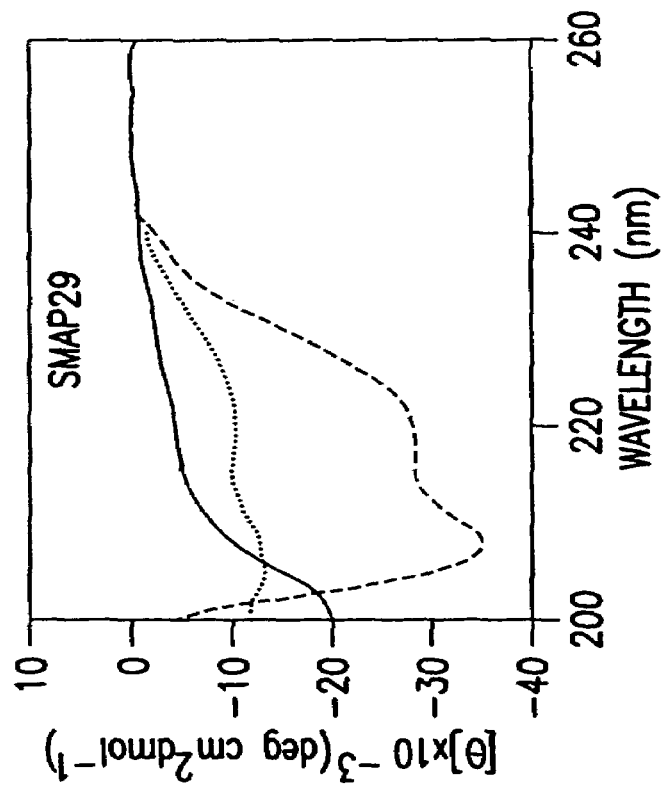
FIG. 3B-1
FIG. 3B-2

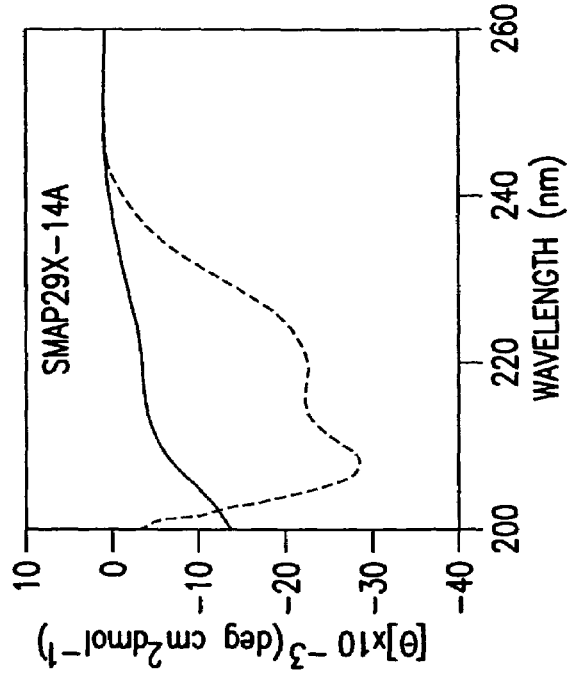
FIG.3B-3
FIG.3B-4
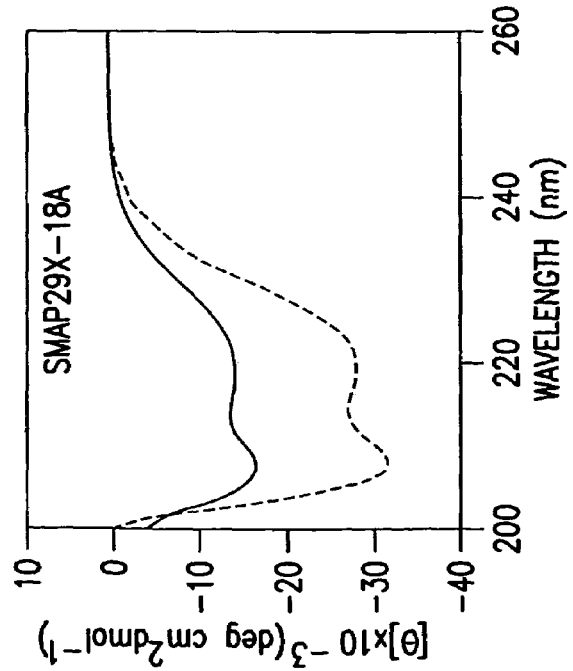
|  | Pi | 0.1% LPS | 40% TFE |
|---|---|---|---|
| SMAP29 | 12.6 | 30.1 | 80.9 |
| SMAP29-18 | 2.0 | 16.4 | 45.4 |
| SMAP29X-18A | 45.6 | — | 88.8 |
| SMAP29X-14A | 13.9 | — | 77.4 |
FIG.3B-5

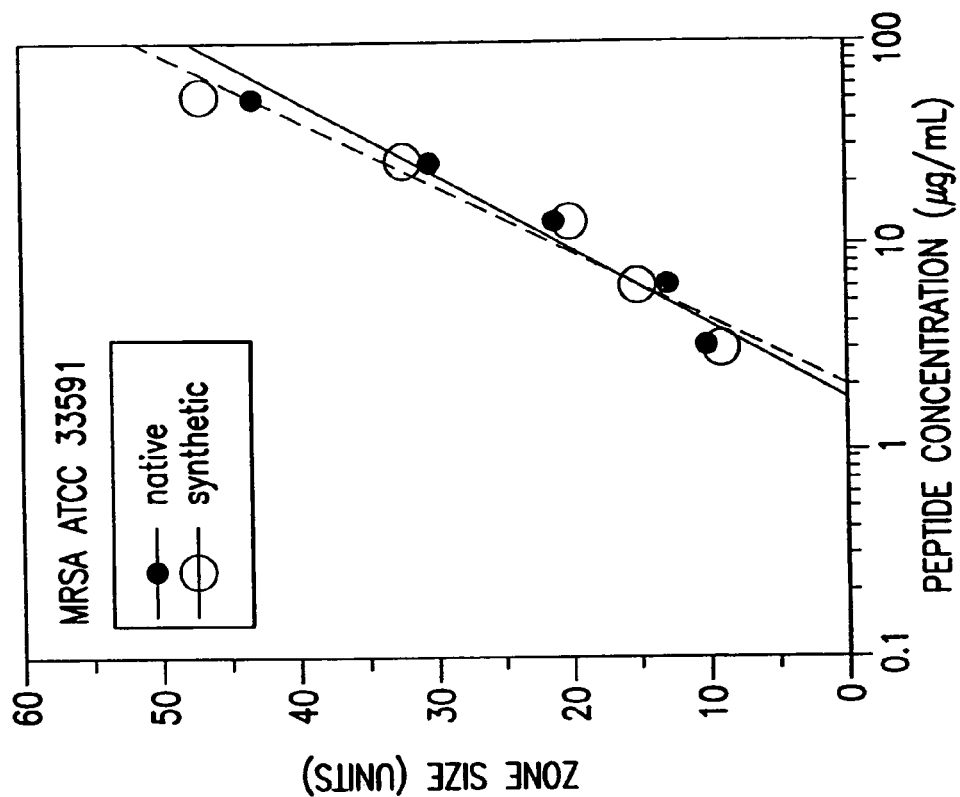
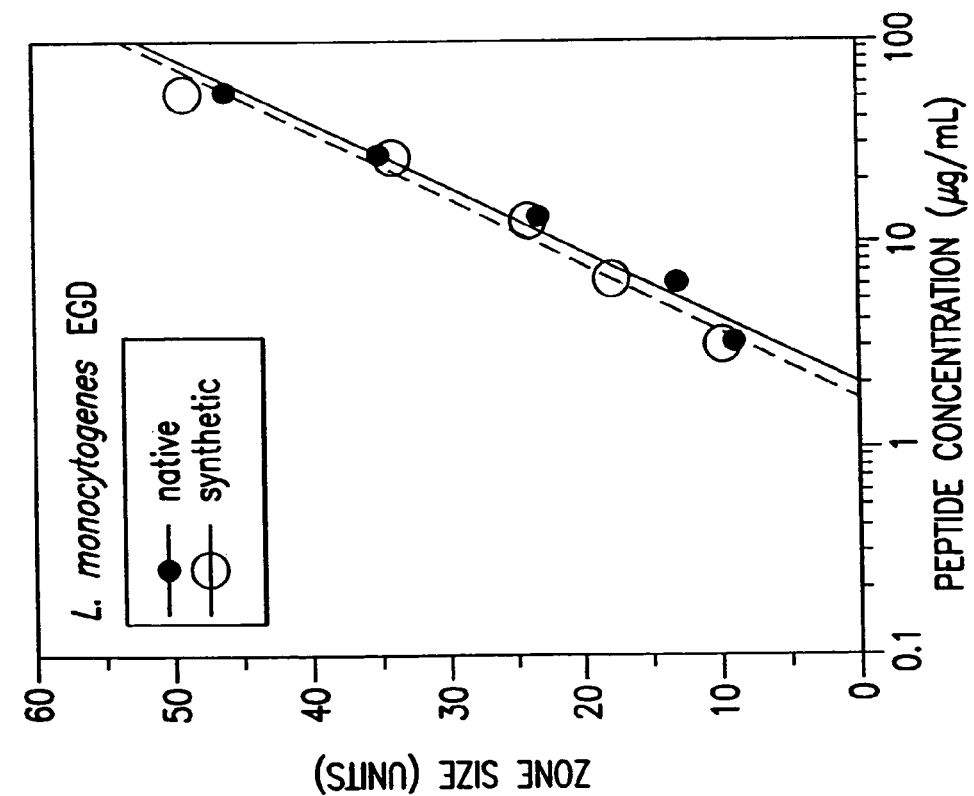
FIG. 9B
FIG. 9A

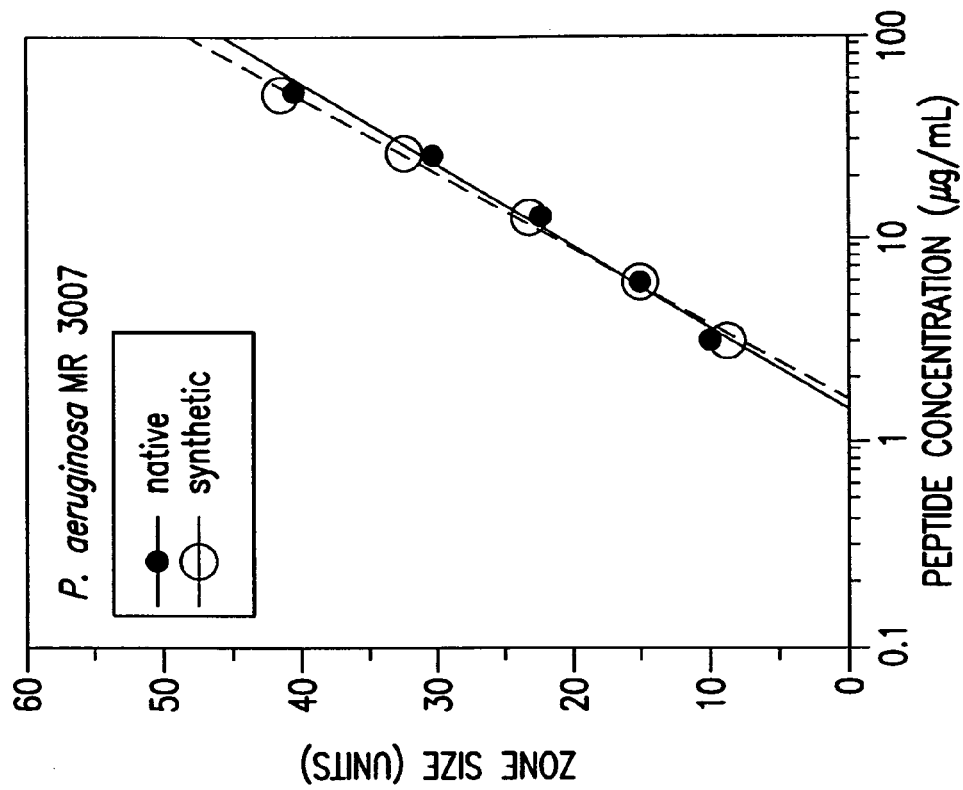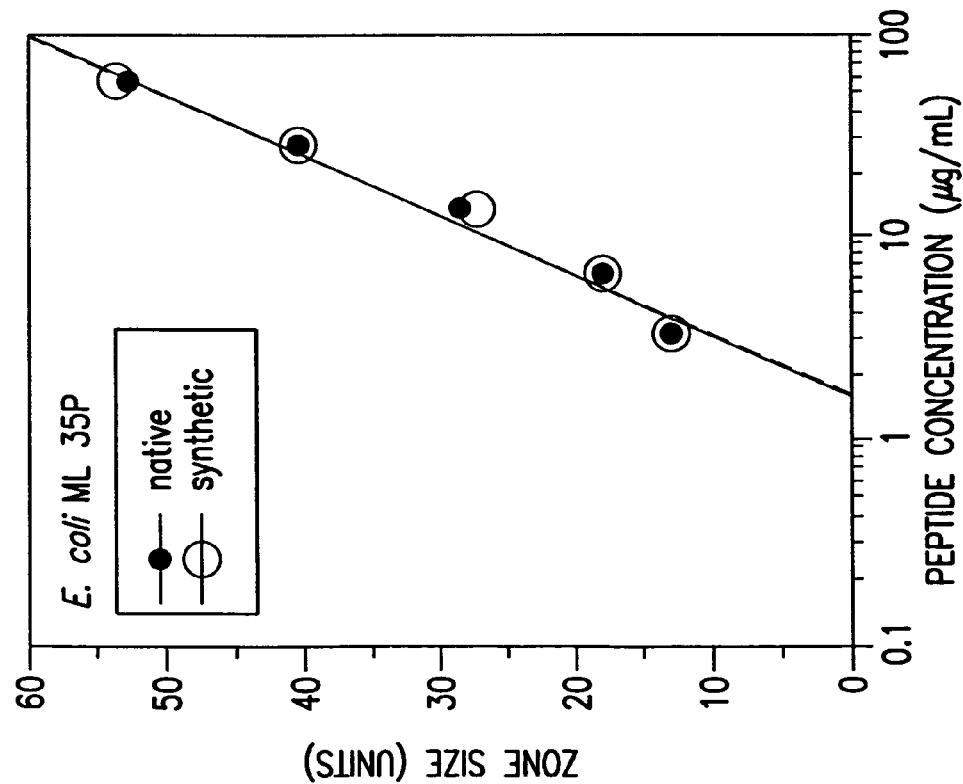

SEQUENCE LISTING

```
<160> NUMBER OF SEQ ID NOS: 34

<210> SEQ ID NO 1
<211> LENGTH: 18
<212> TYPE: PRT
<213> ORGANISM: Ovis aries

<400> SEQUENCE: 1

Lys Asn Leu Arg Arg Ile Ile Arg Lys Ile Ile His Ile Ile Lys Lys
 1               5                  10                  15

Tyr Gly

<210> SEQ ID NO 2
<211> LENGTH: 29
<212> TYPE: PRT
<213> ORGANISM: Ovis aries

<400> SEQUENCE: 2

Arg Gly Leu Arg Arg Leu Gly Arg Lys Ile Ala His Gly Val Lys Lys
 1               5                  10                  15
```

-continued

```
Tyr Gly Pro Thr Val Leu Arg Ile Ile Arg Ile Ala Gly
            20                  25

<210> SEQ ID NO 3
<211> LENGTH: 21
<212> TYPE: PRT
<213> ORGANISM: Ovis aries

<400> SEQUENCE: 3

Lys Ile Ala His Gly Val Lys Lys Tyr Gly Pro Thr Val Leu Arg Ile
 1               5                  10                  15

Ile Arg Ile Ala Gly
            20

<210> SEQ ID NO 4
<211> LENGTH: 20
<212> TYPE: PRT
<213> ORGANISM: Ovis aries

<400> SEQUENCE: 4

Leu Gly Arg Lys Ile Ala His Gly Val Lys Lys Tyr Gly Pro Thr Val
 1               5                  10                  15

Leu Arg Ile Ile
            20

<210> SEQ ID NO 5
<211> LENGTH: 18
<212> TYPE: PRT
<213> ORGANISM: Ovis aries

<400> SEQUENCE: 5

Arg Gly Leu Arg Arg Leu Gly Arg Lys Ile Ala His Gly Val Lys Lys
 1               5                  10                  15

Tyr Gly

<210> SEQ ID NO 6
<211> LENGTH: 18
<212> TYPE: PRT
<213> ORGANISM: Ovis aries

<400> SEQUENCE: 6

Lys Asn Ile Arg Arg Ile Ile Arg Lys Ile Ile His Ile Ile Lys Lys
 1               5                  10                  15

Tyr Gly

<210> SEQ ID NO 7
<211> LENGTH: 18
<212> TYPE: PRT
<213> ORGANISM: Ovis aries

<400> SEQUENCE: 7

Lys Asn Ile Arg Arg Ile Ile Arg Lys Ile Ile His Ile Ile Lys Lys
 1               5                  10                  15

Tyr Gly

<210> SEQ ID NO 8
<211> LENGTH: 18
<212> TYPE: PRT
<213> ORGANISM: Ovis aries

<400> SEQUENCE: 8

Lys Asn Leu Arg Arg Ile Ile Arg Lys Ile Ile His Ile Ile Lys Lys
```

```
                1               5                  10                 15
Tyr Gly

<210> SEQ ID NO 9
<211> LENGTH: 16
<212> TYPE: PRT
<213> ORGANISM: Ovis aries

<400> SEQUENCE: 9

Asn Leu Arg Arg Ile Ile Arg Lys Ile Ile His Ile Ile Lys Lys Tyr
 1               5                  10                 15

<210> SEQ ID NO 10
<211> LENGTH: 16
<212> TYPE: PRT
<213> ORGANISM: Ovis aries

<400> SEQUENCE: 10

Asn Ile Arg Arg Ile Ile Arg Lys Ile Ile His Ile Ile Lys Lys Tyr
 1               5                  10                 15

<210> SEQ ID NO 11
<211> LENGTH: 14
<212> TYPE: PRT
<213> ORGANISM: Ovis aries

<400> SEQUENCE: 11

Leu Arg Arg Ile Ile Arg Lys Ile Ile His Ile Ile Lys Lys
 1               5                  10

<210> SEQ ID NO 12
<211> LENGTH: 14
<212> TYPE: PRT
<213> ORGANISM: Ovis aries

<400> SEQUENCE: 12

Leu Arg Arg Ile Ile Arg Lys Ile Ile His Ile Ile Lys Lys
 1               5                  10

<210> SEQ ID NO 13
<211> LENGTH: 14
<212> TYPE: PRT
<213> ORGANISM: Ovis aries

<400> SEQUENCE: 13

Ile Arg Arg Ile Ile Arg Lys Ile Ile His Ile Ile Lys Lys
 1               5                  10

<210> SEQ ID NO 14
<211> LENGTH: 14
<212> TYPE: PRT
<213> ORGANISM: Ovis aries

<400> SEQUENCE: 14

Ile Arg Arg Ile Ile Arg Lys Ile Ile His Ile Ile Lys Lys
 1               5                  10

<210> SEQ ID NO 15
<211> LENGTH: 13
<212> TYPE: PRT
<213> ORGANISM: Ovis aries

<400> SEQUENCE: 15

Leu Arg Arg Ile Ile Arg Lys Ile Ile His Ile Ile Lys
```

```
                    1               5                   10
```

<210> SEQ ID NO 16
<211> LENGTH: 13
<212> TYPE: PRT
<213> ORGANISM: Ovis aries

<400> SEQUENCE: 16

```
Arg Arg Ile Ile Arg Lys Ile Ile His Ile Ile Lys Lys
 1               5                   10
```

<210> SEQ ID NO 17
<211> LENGTH: 12
<212> TYPE: PRT
<213> ORGANISM: Ovis aries

<400> SEQUENCE: 17

```
Arg Arg Ile Ile Arg Lys Ile Ile His Ile Ile Lys
 1               5                   10
```

<210> SEQ ID NO 18
<211> LENGTH: 37
<212> TYPE: PRT
<213> ORGANISM: Oryctolagus cuniculus

<400> SEQUENCE: 18

```
Gly Leu Arg Lys Arg Leu Arg Lys Phe Arg Asn Lys Ile Lys Glu Lys
 1               5                   10                  15

Leu Lys Lys Ile Gly Gln Lys Ile Gln Gly Leu Leu Pro Lys Leu Ala
            20                  25                  30

Pro Arg Thr Asp Tyr
        35
```

<210> SEQ ID NO 19
<211> LENGTH: 21
<212> TYPE: PRT
<213> ORGANISM: Oryctolagus cuniculus

<400> SEQUENCE: 19

```
Gly Leu Arg Lys Arg Leu Arg Lys Phe Arg Asn Lys Ile Lys Glu Lys
 1               5                   10                  15

Leu Lys Lys Ile Gly
            20
```

<210> SEQ ID NO 20
<211> LENGTH: 18
<212> TYPE: PRT
<213> ORGANISM: Oryctolagus cuniculus

<400> SEQUENCE: 20

```
Lys Arg Leu Arg Lys Phe Arg Asn Lys Ile Lys Glu Lys Leu Lys Lys
 1               5                   10                  15

Ile Gly
```

<210> SEQ ID NO 21
<211> LENGTH: 22
<212> TYPE: PRT
<213> ORGANISM: Oryctolagus cuniculus

<400> SEQUENCE: 21

```
Arg Lys Arg Leu Arg Lys Phe Arg Asn Lys Ile Lys Glu Lys Leu Lys
 1               5                   10                  15
```

-continued

Lys Ile Gly Gln Lys Ile
            20

<210> SEQ ID NO 22
<211> LENGTH: 19
<212> TYPE: PRT
<213> ORGANISM: Oryctolagus cuniculus

<400> SEQUENCE: 22

Leu Arg Lys Phe Arg Asn Lys Ile Lys Glu Lys Leu Lys Lys Ile Gly
1               5                  10                  15

Gln Lys Ile

<210> SEQ ID NO 23
<211> LENGTH: 21
<212> TYPE: PRT
<213> ORGANISM: Oryctolagus cuniculus

<400> SEQUENCE: 23

Leu Arg Lys Phe Arg Asn Lys Ile Lys Glu Lys Leu Lys Lys Ile Gly
1               5                  10                  15

Gln Lys Ile Gln Gly
            20

<210> SEQ ID NO 24
<211> LENGTH: 15
<212> TYPE: PRT
<213> ORGANISM: Oryctolagus cuniculus

<400> SEQUENCE: 24

Arg Lys Phe Arg Asn Lys Ile Lys Glu Lys Leu Lys Lys Ile Gly
1               5                  10                  15

<210> SEQ ID NO 25
<211> LENGTH: 15
<212> TYPE: PRT
<213> ORGANISM: Oryctolagus cuniculus

<400> SEQUENCE: 25

Lys Ile Lys Glu Lys Leu Lys Lys Ile Gly Gln Lys Ile Gln Gly
1               5                  10                  15

<210> SEQ ID NO 26
<211> LENGTH: 17
<212> TYPE: PRT
<213> ORGANISM: Oryctolagus cuniculus

<400> SEQUENCE: 26

Lys Ile Lys Glu Lys Leu Lys Lys Ile Gly Gln Lys Ile Gln Gly Leu
1               5                  10                  15

Leu

<210> SEQ ID NO 27
<211> LENGTH: 28
<212> TYPE: PRT
<213> ORGANISM: Ovis aries

<400> SEQUENCE: 27

Arg Gly Leu Arg Arg Leu Gly Arg Lys Ile Ala His Gly Val Lys Lys
1               5                  10                  15

Tyr Gly Pro Thr Val Leu Arg Ile Ile Arg Ile Ala
            20                  25

-continued

<210> SEQ ID NO 28
<211> LENGTH: 29
<212> TYPE: PRT
<213> ORGANISM: Ovis aries

<400> SEQUENCE: 28

Lys Asn Leu Arg Arg Ile Ile Arg Lys Ile Ile His Ile Ile Lys Lys
 1               5                  10                  15

Tyr Gly Pro Thr Ile Leu Arg Ile Ile Arg Ile Ile Gly
            20                  25

<210> SEQ ID NO 29
<211> LENGTH: 18
<212> TYPE: PRT
<213> ORGANISM: Ovis aries

<400> SEQUENCE: 29

Arg Gly Leu Arg Ala Leu Gly Arg Lys Ile Ala His Gly Val Lys Ala
 1               5                  10                  15

Tyr Gly

<210> SEQ ID NO 30
<211> LENGTH: 16
<212> TYPE: PRT
<213> ORGANISM: Ovis aries

<400> SEQUENCE: 30

Asn Leu Arg Arg Ile Ile Arg Lys Ile Ile His Ile Ile Lys Lys Tyr
 1               5                  10                  15

<210> SEQ ID NO 31
<211> LENGTH: 16
<212> TYPE: PRT
<213> ORGANISM: Ovis aries

<400> SEQUENCE: 31

Asn Ile Arg Arg Ile Ile Arg Lys Ile Ile His Ile Ile Lys Lys Tyr
 1               5                  10                  15

<210> SEQ ID NO 32
<211> LENGTH: 11
<212> TYPE: PRT
<213> ORGANISM: Ovis aries

<400> SEQUENCE: 32

Arg Arg Ile Ile Arg Lys Ile Ile His Ile Ile
 1               5                  10

<210> SEQ ID NO 33
<211> LENGTH: 11
<212> TYPE: PRT
<213> ORGANISM: Ovis aries

<400> SEQUENCE: 33

Arg Ile Ile Arg Lys Ile Ile His Ile Ile Lys
 1               5                  10

<210> SEQ ID NO 34
<211> LENGTH: 10
<212> TYPE: PRT
<213> ORGANISM: Ovis aries

<400> SEQUENCE: 34

Arg Ile Ile Arg Lys Ile Ile His Ile Ile
1               5                   10

ALPHA HELICAL PEPTIDES WITH BROAD SPECTRUM ANTIMICROBIAL ACTIVITY THAT ARE INSENSITIVE TO SALT

This application claims the benefit of priority to U.S. Provisional Application serial No. 60/149,886 filed Aug. 18, 1999, which is specifically incorporated by reference in its entirety.

The government may have rights in the present invention pursuant to grant number NIH P50 HL-61234-01 from the National Institutes of Health, Cystic Fibrosis Foundation

BACKGROUND OF THE INVENTION

1. Field of the Invention

The present invention relates generally to the fields of molecular biology and microbiology. More particularly, it concerns the use of antimicrobial peptides for the inhibition of microbial growth.

2. Description of Related Art

The first antibiotics were used clinically in the 1940s and 1950s, and their use has been increasing significantly since this period. Although an invaluable advance, antibiotic and antimicrobial therapy suffers from several problems, particularly when strains of various bacteria appear that are resistant to antibiotics. Interestingly, bacteria resistant to streptomycin were isolated about a year after this antibiotic was introduced (Waksman, 1945).

The development of antibiotic resistance is a serious and life-threatening event of worldwide importance. For example, strains of Staphylococcus are known that are immune to all antibiotics except one (Travis, 1994). Such bacteria often cause fatal hospital infections. Among other drug resistant organisms are: pneumococci that cause pneumonia and meningitis; Cryptosporidium and E. coli that cause diarrhea; and enterococci that cause blood-stream, surgical wound and urinary tract infections (Berkelman et. al., 1994). The danger is further compounded by the fact that antibiotic and antimicrobial resistance may be spread vertically and horizontally by plasmids and transposons.

Davies (1986) described seven basic biochemical mechanisms for naturally-occurring antibiotic resistance: (1) alteration (inactivation) of the antibiotic; (2) alteration of the target site; (3) blockage in the transport of the antibiotic; (4) by-pass of the antibiotic sensitive-step (replacement); (5) increase in the level of the inhibited enzyme (titration of drug); (6) sparing the antibiotic-sensitive step by endogenous or exogenous product; and (7) production of a metabolite that antagonizes action of inhibitor.

Antimicrobial peptides have been isolated from plants, insects, fish, amphibia, birds, and mammals (Gallo, 1998; Ganz & Lehrer, 1998). Although previously considered an evolutionarily ancient system of immune protection with little relevance beyond minimal primary protection, recent developments have found that mammalian cells express these peptide antibiotics during inflammatory events such as wound repair, contact dermatitis and psoriasis (From Nilsson, 1999). These peptides are apparently a primary component of innate host protection against microbial pathogenesis functioning to create pores in the cytoplasmic membrane of microorganisms (Oren et al., 1998). Furthermore, antimicrobial peptides also act on animal cells by stimulating them to change behaviors such as syndecan expression, chemotaxis, and chloride secretion (Gallo, 1998). After contact with microorganisms, vertebrate skin, trachea and tongue epithelia are rich sources of peptide antibiotics, which may explain the unexpected resistance of these tissues to infection (Russell et al. 1996).

The present invention seeks to overcome these and other drawbacks inherent in the prior art by providing new compositions, combined compositions, methods and kits, for use in reducing resistance to antimicrobials and antibiotics and for treating infections.

SUMMARY OF THE INVENTION

The present invention provides new methods, combined compositions and kits, for use in inhibiting microbial growth and proliferation, reducing resistance to antimicrobials, and providing novel antibiotics for treating infections. The invention rests in the surprising use of one or more antimicrobial peptides alone, or in conjunction with an antimicrobial agent or antibiotic in the control of microbial growth and or proliferation.

The invention therefore encompasses methods, compositions, and kits that relate to an antimicrobial peptide. One embodiment thus represents an isolated antimicrobial peptide comprising the amino acid sequence: KNLRRIIRKII-HIIKKYG-$NH_2$ (SEQ ID NO: 1), KNIRRIIRKIIHIIKKYG-$NH_2$ (SEQ ID NO: 6), KNIRRIIRKIIHIIKKYG (SEQ ID NO: 7), KNLRRIIRKIIHIIKKYG (SEQ ID NO: 8), NLR-RIIRKIIHIIKKY (SEQ ID NO 9), NIRRIIRKIIHIIKKY (SEQ ID NO: 10), LRRIIRKIIHIIKK-$NH_2$ (SEQ ID NO: 11), LRRIIRKIIHIIKK (SEQ ID NO: 12), IRRIIRKIIHI-IKK-$NH_2$ (SEQ ID NO: 13), IRRIIRKIIHIIKK (SEQ ID NO: 14), LRRIIRKIIHIIK-$NH_2$ (SEQ ID NO: 15), RRI-IRKIIHIIKK-$NH_2$ (SEQ ID NO: 16), RRIIRKIIHIIK-$NH_2$ (SEQ ID NO: 17) GLRKRLRKFRNKIKEKLKKIG (SEQ ID NO: 19), KRLRKFRNKIKEKLKKIG (SEQ ID NO: 20), RKRLRKFRNKIKEKLKKIGQKI (SEQ ID NO: 21), LRK-FRNKIKEKLKKIGQKI (SEQ ID NO: 22), LRK-FRNKIKEKLKKIGQKIQG (SEQ ID NO: 23), RKFRNKIKEKLKKIG (SEQ ID NO: 24), KIKEKLK-KIGQKIQG (SEQ ID NO: 25), KIKEKLKKIGQKIQGLL (SEQ ID NO: 26) RGLRRLGRKIAHGVKKYGPTVLRI-IRIA-$NH_2$ (SEQ ID NO. 27), or KNLRRIIRKIIHI-IKKYGPTILRIIRIIG-$NH_2$ (SEQ ID NO. 28).

An additional embodiment would consist of a pharmaceutical composition wherein said composition comprises the antimicrobial peptide comprising the amino acid sequence: KNLRRIIRKIIHIIKKYG-$NH_2$ (SEQ ID NO: 1), KNIRRIIRKIIHIIKKYG-$NH_2$ (SEQ ID NO:6), KNIRRI-IRKIIHIIKKYG (SEQ ID NO: 7), KNLRRIIRKIIHI-IKKYG (SEQ ID NO: 8), NLRRIIRKIIHIIKKY (SEQ ID NO 9), NIRRIIRKIIHIIKKY (SEQ ID NO: 10), LRRI-IRKIIHIIKK-$NH_2$ (SEQ ID NO: 11), LRRIIRKIIHIIKK (SEQ ID NO: 12), IRRIIRKIIHIIKK-$NH_2$ (SEQ ID NO: 13), IRRIIRKIIHIIKK (SEQ ID NO: 14), LRRIIRKIIHIIK-$NH_2$ (SEQ ID NO: 15), RRIIRKIIHIIKK-$NH_2$ (SEQ ID NO: 16), RRIIRKIIHIIK-$NH_2$ (SEQ ID NO: 17), GLRKRLRK-FRNKIKEKLKKIG (SEQ ID NO: 19), KRLRK-FRNKIKEKLKKIG (SEQ ID NO: 20), RKRLRK-FRNKIKEKLKKIGQKI (SEQ ID NO: 21), LRKFRNKIKEKLKKIGQKI (SEQ ID NO: 22), LRK-FRNKIKEKLKKIGQKIQG (SEQ ID NO: 23), RKFRNKIKEKLKKIG (SEQ ID NO: 24), KIKEKLK-KIGQKIQG (SEQ ID NO: 25), KIKEKLKKIGQKIQGLL (SEQ ID NO: 26) RGLRRLGRKIAHGVKKYGPTVLRI-IRIA-$NH_2$ (SEQ ID NO. 27), or KNLRRIIRKIIHI-IKKYGPTILRIIRIIG-$NH_2$ (SEQ ID NO. 28), and a pharmaceutically acceptable carrier.

In a further embodiment of the invention, an antimicrobial peptide will be introduced into an environment, including but not limited to a host, in order to inhibit the growth and/or proliferation of microbial organisms. Such an introduction envisions that the microbial organism will be contacted by the antimicrobial peptide, and as a result of this contact, the growth and or proliferation of the microbial organism will be inhibited. A preferred embodiment is a method of inhibiting microbial growth in an environment capable of sustaining such growth comprising administering to said environment the antimicrobial peptide comprising the amino acid sequence: KNLRRIIRKIIHIIKKYG-NH$_2$ (SEQ ID NO: 1), KNIRRIIRKIIHIIKKYG-NH$_2$ (SEQ ID NO: 6), KNIRRIIRKIIHIIKKYG (SEQ ID NO: 7), KNLRRIIRKIIHIIKKYG (SEQ ID NO: 8), NLRRIIRKIIHIIKKY (SEQ ID NO 9), NIRRIIRKIIHIIKKY (SEQ ID NO: 10), LRRIIRKIIHIIKK-NH$_2$ (SEQ ID NO: 11), LRRIIRKIIHIIKK (SEQ ID NO: 12), IRRIIRKIIHIIKK-NH$_2$ (SEQ ID NO: 13), IRRIIRKIIHIIKK (SEQ ID NO: 14), LRRIIRKIIHIIK-NH$_2$ (SEQ ID NO: 15), RRIIRKIIHIIKK-NH$_2$ (SEQ ID NO: 16), RRIIRKIIHIIK-NH$_2$ (SEQ ID NO: 17), GLRKRLRKFRNKIKEKLKKIGQKIQGLLPKLAPRTDY (SEQ ID NO: 18), GLRKRLRKFRNKIKEKLKKIG (SEQ ID NO: 19), KRLRKFRNKIKEKLKKIG (SEQ ID NO: 20), RKRLRKFRNKIKEKLKKIGQKI (SEQ ID NO: 21), LRKFRNKIKEKLKKIGQKI (SEQ ID NO: 22), LRKFRNKIKEKLKKIGQKIQG (SEQ ID NO: 23), RKFRNKIKEKLKKIG (SEQ ID NO: 24), KIKEKLKKIGQKIQG (SEQ ID NO: 25), KIKEKLKKIGQKIQGLL (SEQ ID NO: 26) RGLRRLGRKIAGVKKYGPTVLRIIRIA-NH$_2$ (SEQ ID NO. 27), or KNLRRIIRKIIHIIKKYGPTILRIIRIIG-N$_{12}$ (SEQ ID NO. 28).

Such a method may further consist of administering an antimicrobial peptide in a pharmaceutically acceptable carrier and/or in combination with a second antimicrobial agent or antibiotic. Such antimicrobial agents or antibiotics may include but are not limited to the peptides listed in SEQ ID NO: 2, SEQ ID NO: 3, SEQ ID NO: 4, SEQ ID NO: 5, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 SEQ ID NO: 26, SEQ ID NO: 27 or SEQ ID NO: 28 or a protein synthesis inhibitor, a cell wall growth inhibitor, a cell membrane synthesis inhibitor, a nucleic acid synthesis inhibitor, and a competitive inhibitor.

An additional embodiment would consist of a method of inhibiting microbial growth in a host, comprising administering to said host the antimicrobial peptide comprising the amino acid sequence: KNLRRIIRKIIHIIKKYG-NH$_2$ (SEQ ID NO: 1), RGLRRLGRKIAHGVKKYGPTVLRIIRIAG (SEQ ID NO: 2), KIAHGVKKYGPTVLRIIRIAG (SEQ ID NO: 3), LGRKIAHGVKKYGPTVLRII (SEQ ID NO: 4), RGLRRLGRKIAHGVKKYG (SEQ ID NO: 5), KNIRRIIRKIIHIIKKYG-NH$_2$ (SEQ ID NO: 6), KNIRRIIRKIIHIIKKYG (SEQ ID NO: 7), KNLRRIIRKIIHIIKKYG (SEQ ID NO: 8), NLRRIIRKIIHIIKKY (SEQ ID NO: 9), NIRRIIRKIIHIIKKY (SEQ ID NO: 10), LRRIIRKIIHIIKK-NH$_2$ (SEQ ID NO: 11), LRRIIRKIIHIIKK (SEQ ID NO: 12), IRRIIRKIIHIIKK-NH$_2$ (SEQ ID NO: 13), IRRIIRKIIHIIKK (SEQ ID NO: 14), LRRIIRKIIHIIK-NH$_2$ (SEQ ID NO: 15), RRIIRKIIHIIKK-NH$_2$ (SEQ ID NO: 16), RRIIRKIIHIIK-NH$_2$ (SEQ ID NO: 17), GLRKRLRKFRNKIKEKLKKIGQKIQGLLPKLAPRTDY (SEQ ID NO: 18), GLRKRLRKFRNKIKEKLKKIG (SEQ ID NO: 19), KRLRKFRNKIKEKLKKIG (SEQ ID NO: 20), RKRLRKFRNKIKEKLKKIGQKI (SEQ ID NO: 21), LRKFRNKIKEKLKKIGQKI (SEQ ID NO: 22), LRKFRNKIKEKLKKIGQKIQG (SEQ ID NO: 23), RKFRNKIKEKLKKIG (SEQ ID NO: 24), KIKEKLKKIGQKIQG (SEQ ID NO: 25), KIKEKLKKIGQKIQGLL (SEQ ID NO: 26) RGLRRLGRKIAGVKKYGPTVLRIIRIA-NH$_2$ (SEQ ID NO. 27), or KNLRRIIRKIIHIIKKYGPTILRIIRIIG-NH$_2$ (SEQ ID NO. 28).

The microorganism, e.g., bacterium, yeast, or population thereof, may be contacted either in vitro or in vivo. Contacting in vivo may be achieved by administering to an animal (including a human patient) that has, or is suspected to have a microbial or bacterial infection, a therapeutically effective amount of pharmacologically acceptable antimicrobial peptide formulation alone or in combination with a therapeutic amount of a pharmacologically acceptable formulation of a second agent. The invention may thus be employed to treat both systemic and localized microbial, bacterial, and fungal infections by introducing the agent or agents into the general circulation or by applying the combination, e.g., topically to a specific site, such as a wound or burn, or to the eye, ear or other site of infection.

An "effective amount of an antimicrobial agent or peptide" means an amount, or dose, within the range required to inhibit bacterial growth and/or proliferation. Such ranges would be readily determinable to those of skill in the art depending upon the use to which the peptide is to be applied. An "effective amount of an antimicrobial agent or antibiotic" means an amount, or dose, within the range normally given or prescribed. Such ranges are well established in routine clinical practice and will thus be readily determinable to those of skill in the art. Doses may be measured by total amount given or by concentration. Ten, 20, 50, 100, 500 and 1000 µg/ml solutions all are appropriate for treatment. Total doses of 100, 500, 1000, 2000, 5000 and 10,000 µg also appear to be appropriate doses. Appropriate oral and parenteral doses and treatment regimens are further detailed herein in Table 5 and Table 6.

As this invention provides for enhanced microbial and/or bacterial killing, it will be appreciated that effective amounts of an antimicrobial agent or antibiotic may be used that are lower than the standard doses previously recommended when the antimicrobial or antibiotic is combined with an antimicrobial peptide. It is further envisioned that the antimicrobial peptide may be used in combination with other antimicrobial agents or antibiotics for a variety of purposes. These purposes include but are not limited to: enhancing the activity of an agent or antibiotic, allowing for a lower dose of an agent or antibiotic due to toxicity or dosing concerns relating to the second agent or antibiotic, enhancing the activity of agents or antibiotics against strains that have previously exhibited resistance to an agent or antibiotic or providing an additional agent in individuals whose immune system is damaged or compromised and are thus unable to mount an effective immune response.

Where a combination of an antimicrobial peptide and one or more antimicrobial agents or antibiotics is contemplated, it is envisioned that the antimicrobial peptide and the second agent or antibiotic may be delivered either simultaneously or either of the agents may be administered prior to the administration of the other. It is envisioned that staggered administration might weaken the microbial organism and increase the efficacy of the additional agent.

In a preferred embodiment of the invention, an antimicrobial peptide will be used alone or in combination with one or more additional antimicrobial agents or antibiotics in the treatment of microbial strains previously determined to be resistant to one or more methods of treatment. It is envisioned that this method will comprise inhibiting the growth of drug-resistant microbial strains comprising administering to an environment capable of sustaining such growth an antimicrobial peptide comprising the amino acid sequence: KNLRRIIRKIIHIIKKYG-NH₂ (SEQ ID NO: 1), RGLRRLGRKIAHGVKKYGPTVLRIIRIAG (SEQ ID NO: 2), KIAHGVKKYGPTVLRIIRIAG (SEQ ID NO 3), LGRKIAHGVKKYGPTVLRII (SEQ ID NO: 4), RGLRRLGRKIAHGVKKYG (SEQ ID NO: 5), KNIRRIIRKIIHIIKKYG-NH₂ (SEQ ID NO:6), KNIRRIIRKIIHIIKKYG (SEQ ID NO: 7), KNLRRIIRKIIHIIKKYG (SEQ ID NO: 8), NLRRIIRKIIHIIKKY (SEQ ID NO 9), NIRRIIRKIIHIIKKY (SEQ ID NO: 10), LRRIIRKIIHIIKK-NH₂ (SEQ ID NO: 11), LRRIIRKIIHIIKK (SEQ ID NO: 12), IRRIIRKIIHIIKK-NH₂ (SEQ ID NO: 13), IRRIIRKIIHIIKK (SEQ ID NO: 14), LRRIIRKIIHIIK-NH₂ (SEQ ID NO: 15), RRIIRKIIHIIKK-NH₂ (SEQ ID NO: 16), RRIIRKIIHIIK-NH₂ (SEQ ID NO: 17), GLRKRLRKFRNKIKEKLKKIGQKIQGLLPKLAPRTDY (SEQ ID NO: 18), GLRKRLRKFRNKIKEKLKKIG (SEQ ID NO: 19), KRLRKFRNKIKEKLKKIG (SEQ ID NO: 20), RKRLRKFRNKIKEKLKKIGQKI (SEQ ID NO: 21), LRKFRNKIKEKLKKIGQKI (SEQ ID NO: 22), LRKFRNKIKEKLKKIGQKIQG (SEQ ID NO: 23), RKFRNKIKEKLKKIG (SEQ ID NO: 24), KIKEKLKKIGQKIQG (SEQ ID NO: 25), KIKEKLKKIGQKIQGLL (SEQ ID NO: 26) RGLRRLGRKIAHGVKKYGPTVLRIIRIA-NH₂ (SEQ ID NO. 27), or KNLRRIIRKIIHIIKKYGPTILRIIRIIG-NH₂ (SEQ ID NO. 28).

Pharmaceutically acceptable compositions may be formulated such that resistant strains may be treated in a host either ex vivo or in vivo depending upon the requisite circumstances. A list of resistant strains against which an antimicrobial peptide might be employed includes, but is not limited to: *Pseudomonas aeruginosa, Burkholderia cepacia, Alcaligenes, Xanthamonas, Listeria monocytogenes, Staphylococcus aureus* and *Escherichia coli*

In a preferred embodiment of the present invention, the antimicrobial peptides are useful alone or in combination with other antimicrobial agents or antibiotics in the treatment of cystic fibrosis or other diseases of the respiratory system. In the setting of cystic fibrosis, the peptides may be used either prophylactically or therapeutically. Because a variety of bacterial strains cause infections associated with cystic fibrosis the broad spectrum properties of antimicrobial peptides make them well suited for use in the prevention of infection associated with the disease.

A further embodiment of the invention envisions a nucleic acid molecule encoding the antimicrobial peptide comprising the amino acid sequence: KNLRRIIRKIIHIIKKYG-NH₂ (SEQ ID NO: 1), KNIRRIIRKIIHIIKKYG-NH₂ (SEQ ID NO: 6), KNIRRIIRKIIHIIKKYG (SEQ ID NO: 7), KNLRRIIRKIIHIIKKYG (SEQ ID NO: 8), NLRRIIRKIIHIIKKY (SEQ ID NO 9), NIRRIIRKIIHIIKKY (SEQ ID NO: 10), LRRIIRKIIHIIKK-NH₂ (SEQ ID NO: 11), LRRIIRKIIHIIKK (SEQ ID NO: 12), IRRIIRKIIHIIKK-NH₂ (SEQ ID NO: 13), IRRIIRKIIHIIKK (SEQ ID NO: 14), LRRIIRKIIHIIK-NH₂ (SEQ ID NO: 15), RRIIRKIIHIIKK-NH₂ (SEQ ID NO: 16), RRIIRKIIHIIK-NH₂ (SEQ ID NO: 17), GLRKRLRKFRNKIKEKLKKIG (SEQ ID NO: 19), KRLRKFRNKIKEKLKKIG (SEQ ID NO: 20), RKRLRKFRNKIKEKLKKIGQKI (SEQ ID NO: 21), LRKFRNKIKEKLKKIGQKI (SEQ ID NO: 22), LRKFRNKIKEKLKKIGQKIQG (SEQ ID NO: 23), RKFRNKIKEKLKKIG (SEQ ID NO: 24), KIKEKLKKIGQKIQG (SEQ ID NO: 25), KIKEKLKKIGQKIQGLL (SEQ ID NO: 26) RGLRRLGRKIAHGVKKYGPTVLRIIRIA-NH₂ (SEQ ID NO. 27), or KNLRRIIRKIIHIIKKYGPTILRIIRIIG-NH₂ (SEQ ID NO. 28).

It is envisioned that uses of this nucleic acid sequence could include, but are not limited to, creation of degenerate probes for the detection of further antimicrobial peptide species, use in gene therapy or in the creation of fusion constructs linking the antimicrobial peptides of the instant invention to other proteins.

A further embodiment consists of a kit for use in inhibiting microbial growth in a host comprising an antimicrobial peptide comprising the amino acid sequence: KNLRRIIRKIIHIIKKYG-NH₂ (SEQ ID NO: 1), RGLRRLGRKIAHGVKKYGPTVLRIIRIAG (SEQ ID NO: 2), KIAHGVKKYGPTVLRIIRIAG (SEQ ID NO 3), LGRKIAHGVKKYGPTVLRII (SEQ ID NO: 4), RGLRRLGRKIAHGVKKYG (SEQ ID NO: 5), KNIRRIIRKIIHIIKKYG-NH₂ (SEQ ID NO: 6), KNIRRIIRKIIHIIKKYG (SEQ ID NO: 7), KNLRRIIRKIIHIIKKYG (SEQ ID NO: 8), NLRRIIRKIIHIIKKY (SEQ ID NO 9), NIRRIIRKIIHIIKKY (SEQ ID NO: 10), LRRIIRKIIHIIKK-NH₂ (SEQ ID NO: 11), LRRIIRKIIHIIKK (SEQ ID NO: 12), IRRIIRKIIHIIKK-NH₂ (SEQ ID NO: 13), IRRIIRKIIHIIKK (SEQ ID NO: 14), LRRIIRKIIHIIK-NH₂ (SEQ ID NO: 15), RRIIRKIIHIIKK-NH₂ (SEQ ID NO: 16), RRIIRKIIHIIK-NH₂ (SEQ ID NO: 17), GLRKRLRKFRNKIKEKLKKIGQKIQGLLPKLAPRTDY (SEQ ID NO: 18), GLRKRLRKFRNKIKEKLKKIG (SEQ ID NO: 19), KRLRKFRNKIKEKLKKIG (SEQ ID NO: 20), RKRLRKFRNKIKEKLKKIGQKI (SEQ ID NO: 21), LRKFRNKIKEKLKKIGQKI (SEQ ID NO: 22) LRKFRNKIKEKLKKIGQKIQG (SEQ ID NO: 23), RKFRNKIKEKLKKIG (SEQ ID NO: 24), KIKEKLKKIGQKIQG (SEQ ID NO: 25), KIKEKLKKIGQKIQGLL (SEQ ID NO: 26) RGLRRLGRKIAHGVKKYGPTVLRIIRIA-NH₂ (SEQ ID NO. 27), or KNLRRIIRKIIHIIKKYGPTILRIIRIIG-NH₂ (SEQ ID NO. 28). in a suitable container. In an additional embodiment, a kit may contain the antimicrobial peptide and a second antimicrobial agent. The second antimicrobial agent may be selected from the group consisting of a protein synthesis inhibitor, a cell wall growth inhibitor, a cell membrane synthesis inhibitor, a nucleic acid synthesis inhibitor, and a competitive inhibitor.

For the purpose of the instant invention, the term microbe or microbial is considered to encompass, but not be limited to a microscopic pathogen, such as, for example, a virus, virion, bacteria, ricketssial, helminth, nematode, fungi, protozoan or other invasive pathogen.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

Luminescence was measured after 5 hr. Values are percent of control in the absence of antimicrobial peptide; controls were determined for each salt concentration. Symbols indicate mean±range, n=2; in most cases, the error bars are covered by the symbol.

Figures 1, 2A:
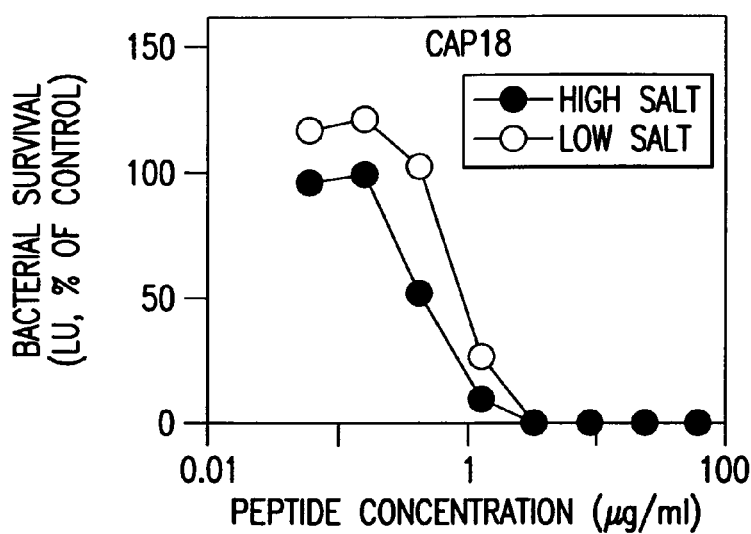
FIG. 1: Antimicrobial activity measured with luminescence assay. Relationship between viability (cfu, o) and luminescence (○) of *P. aeruginosa* PAO1 containing pBBR1MCS-5. Bacteria were incubated with the indicated concentration of LL37 for 5 hr, then luminescence was measured an surviving organisms were plated and counted. Studies were performed at an ionic strength of 25 mM (A) and 175 mM (B). Values are percent of control in absence of LL37. Symbols indicate mean±sem, n=4.
FIGS. 2A and 2B: Effect of ionic strength of antimicrobial activity of CAP18 (FIG. 2A) and SMAP peptides (FIG. 2B). *P. aeruginosa* was incubated with the indicated concentrations of antimicrobial peptide in the standard assay buffer at 25 mM ionic strength (O), or with 150 mM NaCl added (○).
Figures 2, 2A:
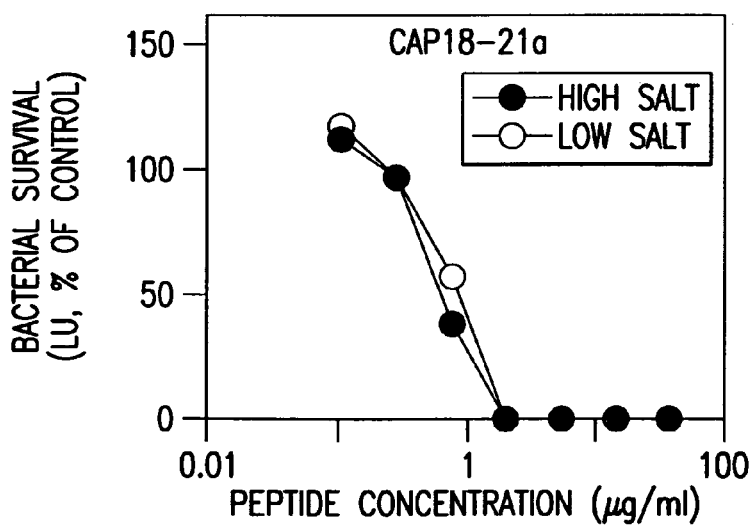
Figures 2, 2A, 3:
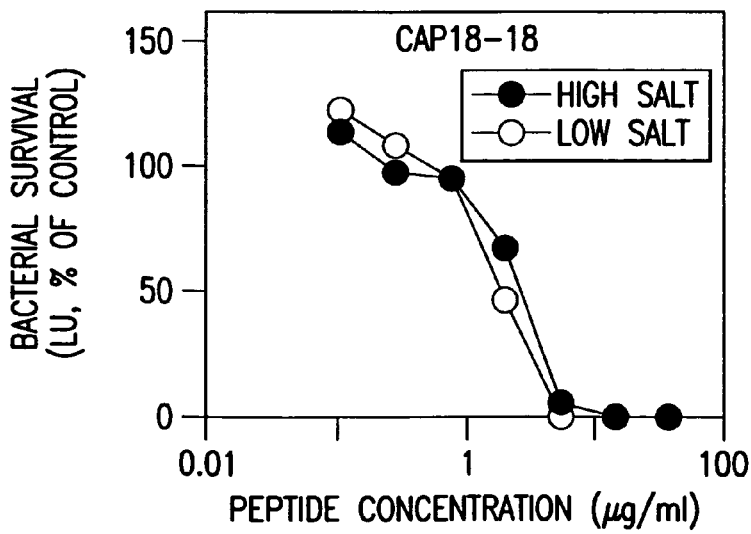
Figures 2, 2A, 3, 4:
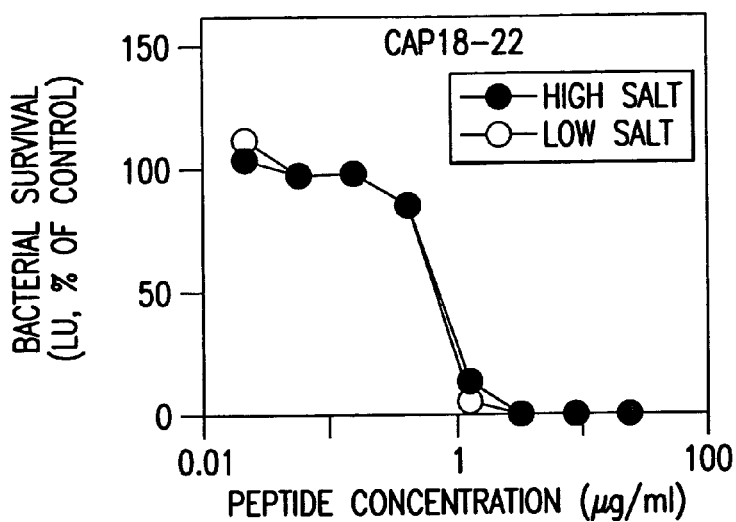
Figures 2, 2A, 3, 4, 5:
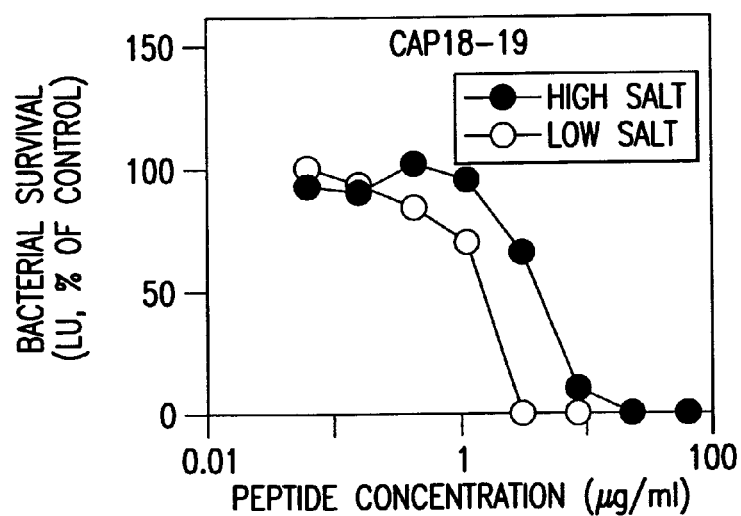

FIGS. 3A and 3B: CD spectra of CAP 18 (FIG. 3A) and SMAP peptides (FIG. 3 B). Spectra of selected peptides were recorded in 0.05 M phosphate buffer pH 7.0 (solid curve), 0.1% LPS (dotted curve) and in a 40% solution of trifluoroethanol (dashed curve) at peptide concentrations of 0.2 mg/ml.

Figures 1, 4A:
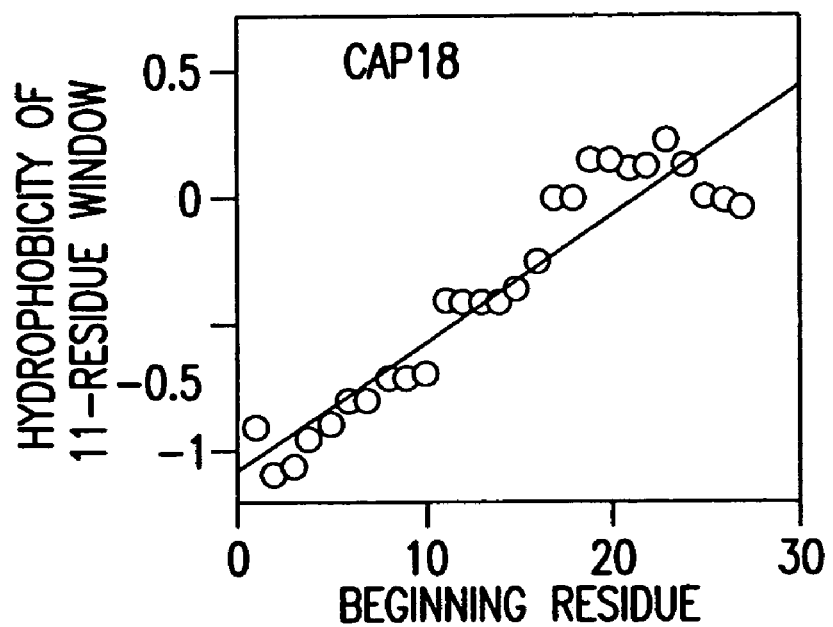
Figures 2, 4A:
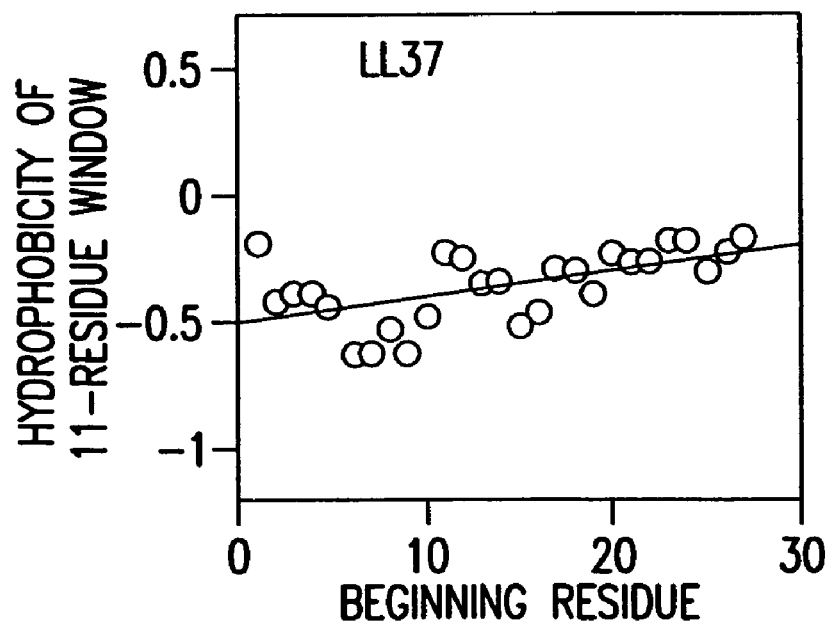
Figures 3, 4A:
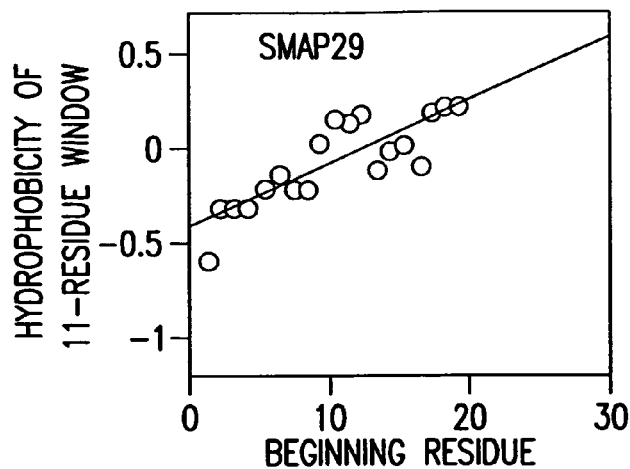
Figures 4, 4A:
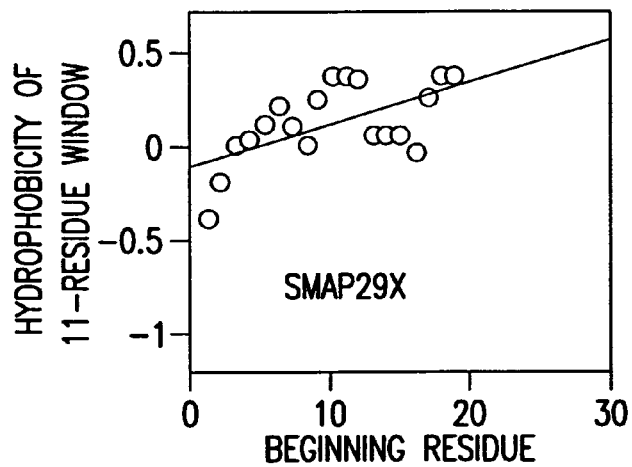
Figures 4, 4A, 5:
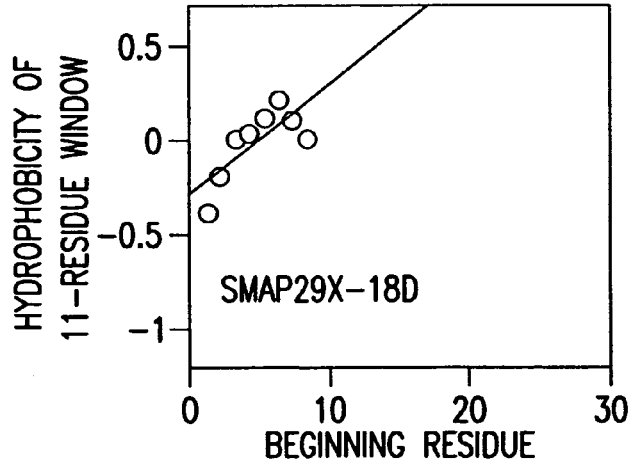
Figure 4B:
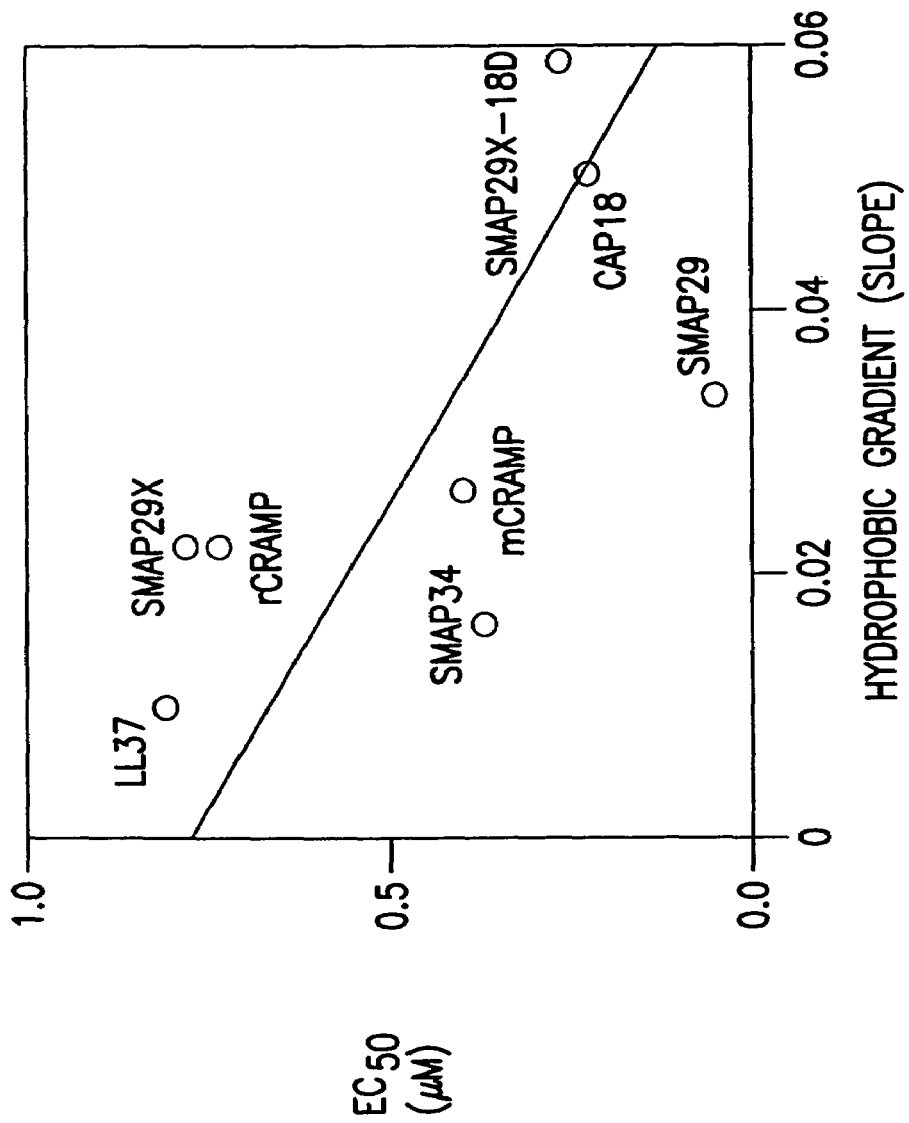

FIGS. 4A and 4B: Hydrophobicity gradients of cathelicidin peptides. FIG. 4A. The hydrophobicity of each 11-residue window was calculated as described by Eisenberg (1986), and a line was fit by linear regression. The more hydrophobic regions have more negative hydrohobicity values. FIG. 4B. Relationship between antipseudomonal potency (PAO1) and the slope of the hydrophobicity gradient across the peptide.

Figures 1, 5A:
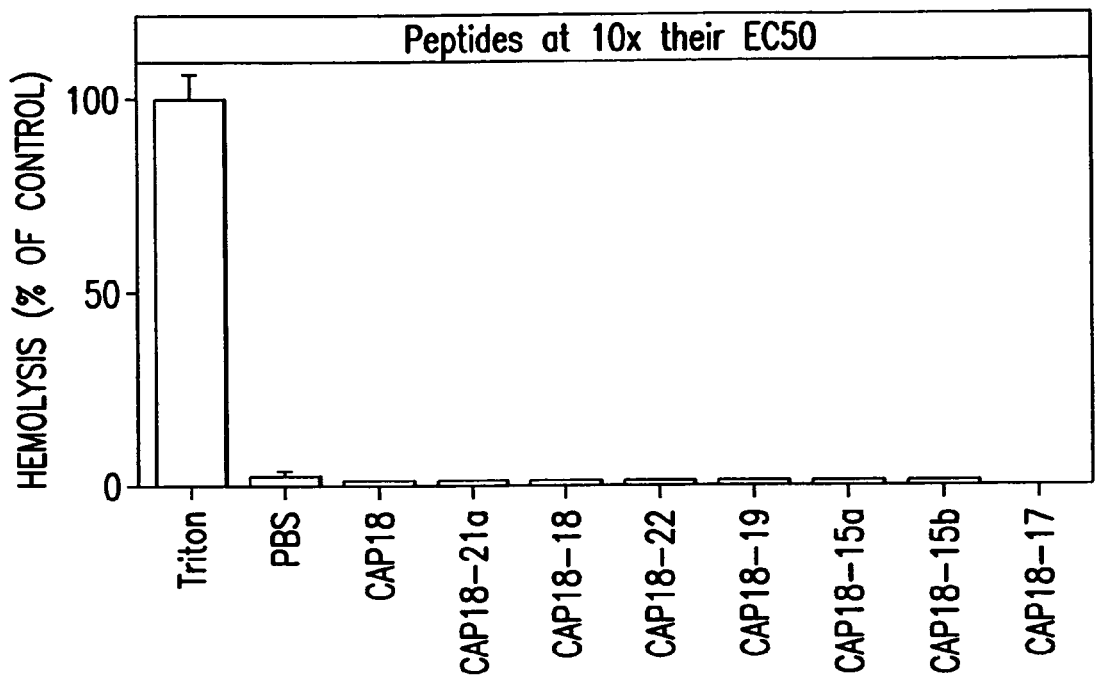
Figures 2, 5A:
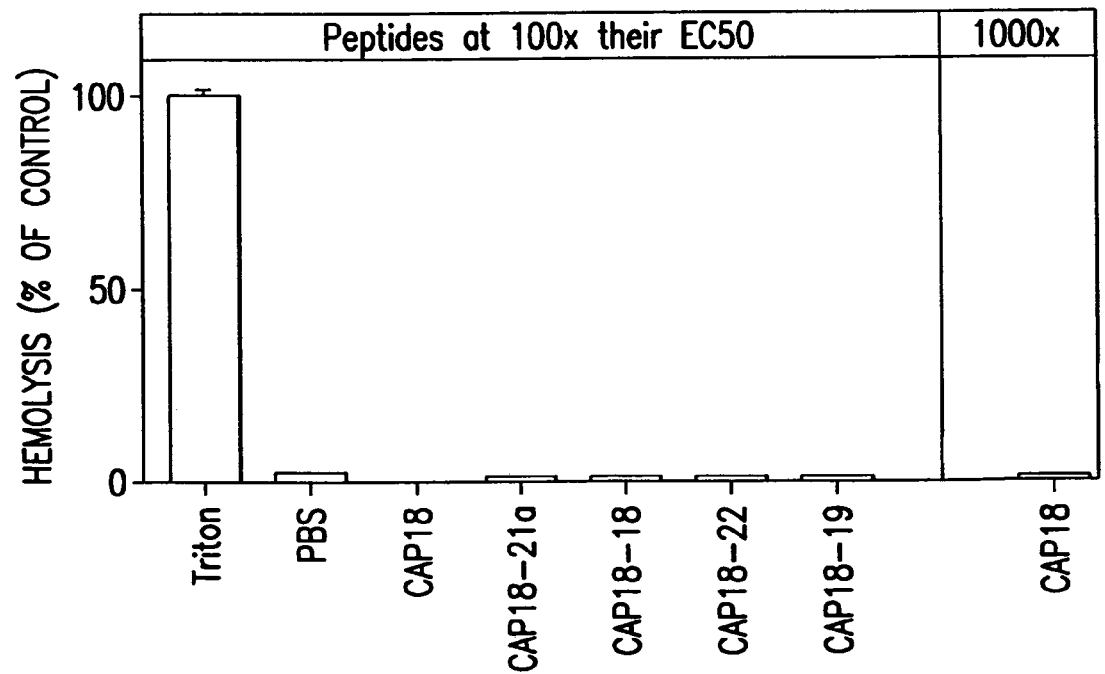
Figures 1, 5B:
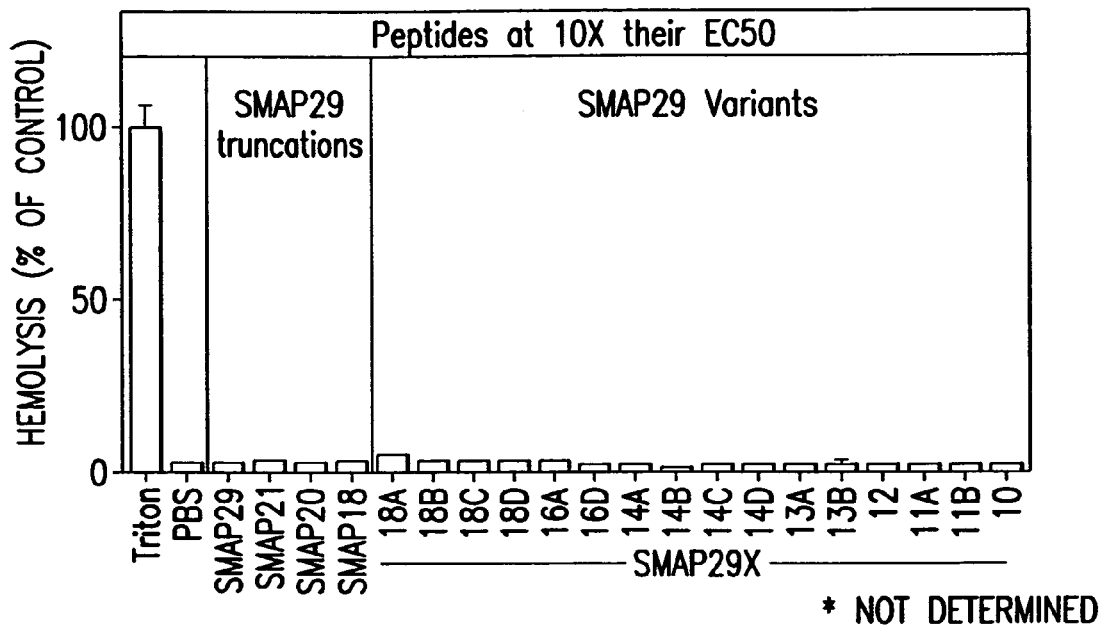
Figures 2, 5B:
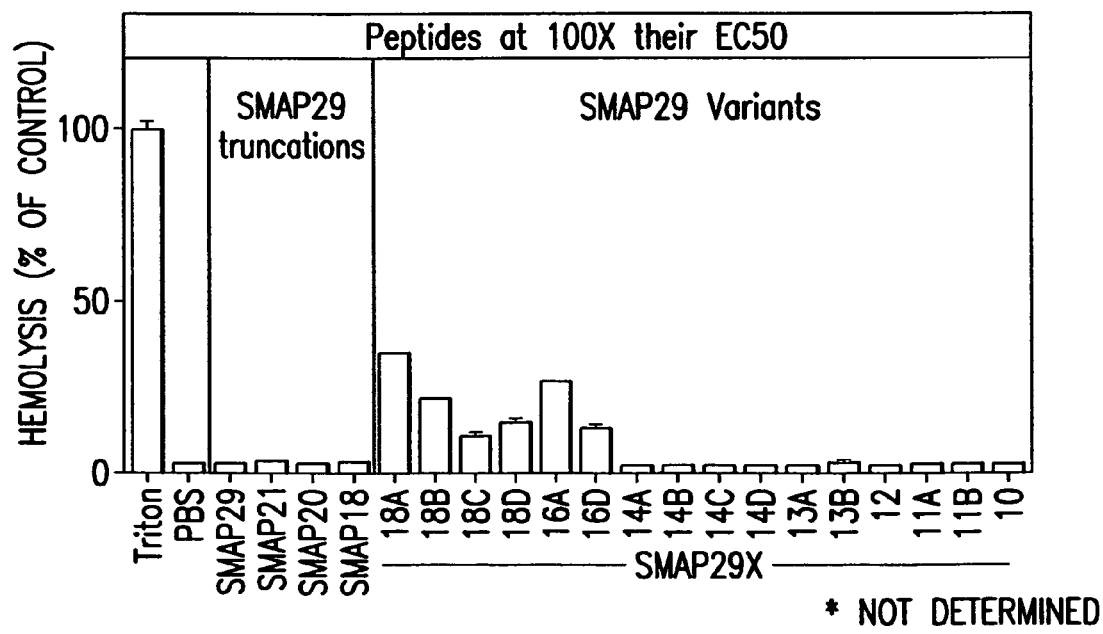
Figures 3, 5B:
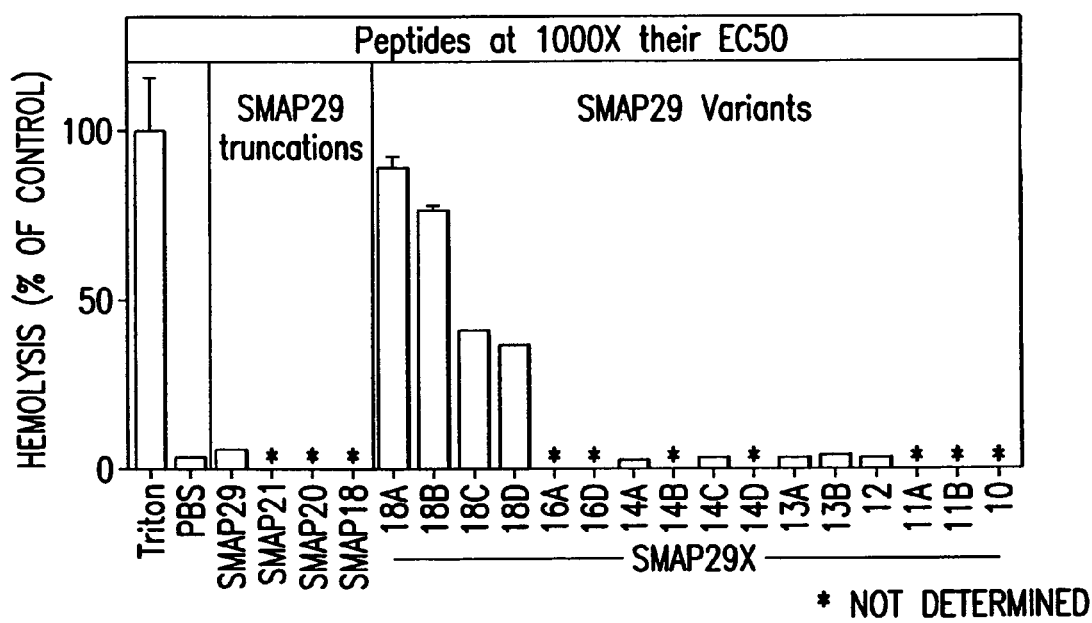
Figure 6:
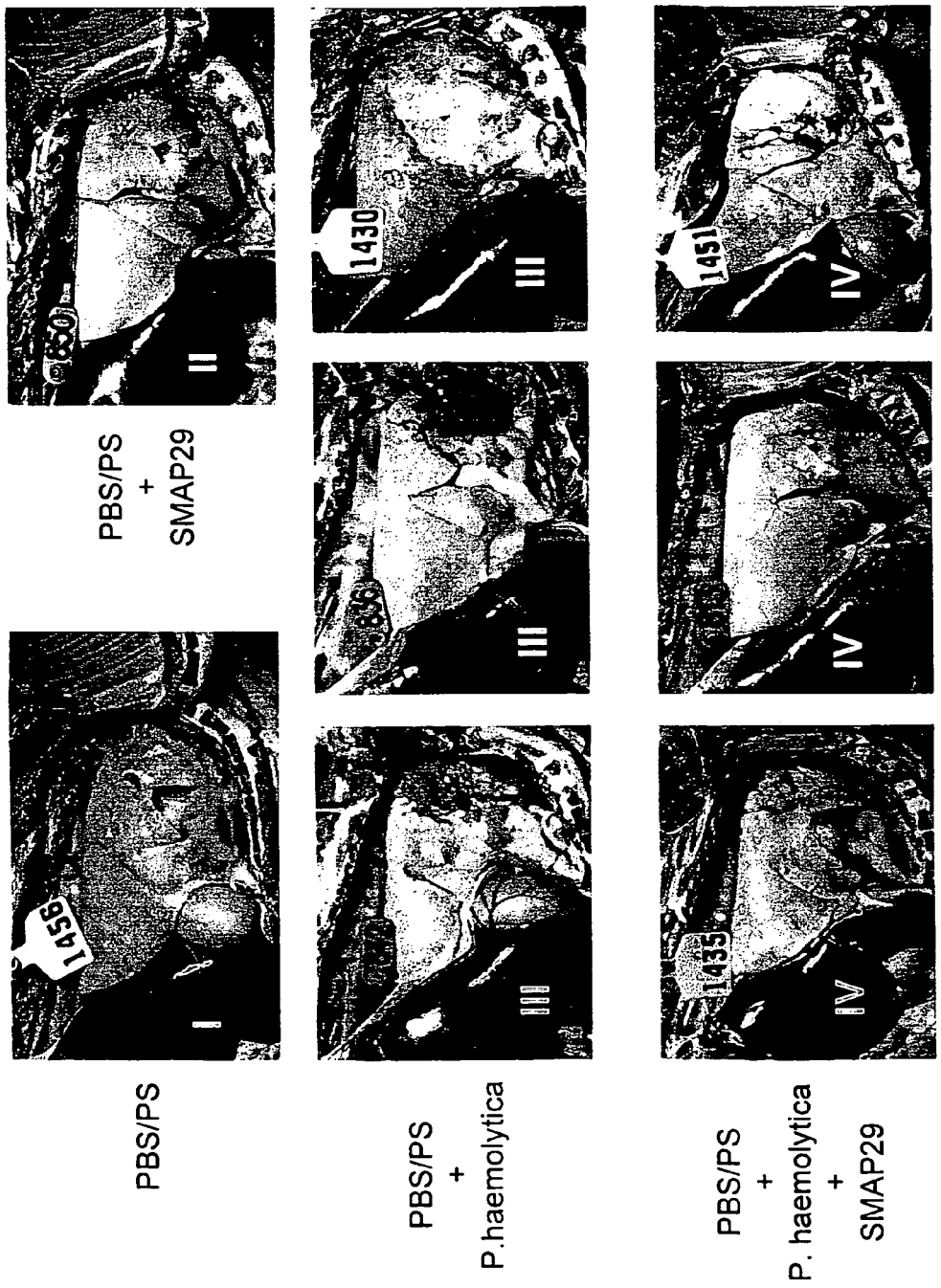
Figure 7:
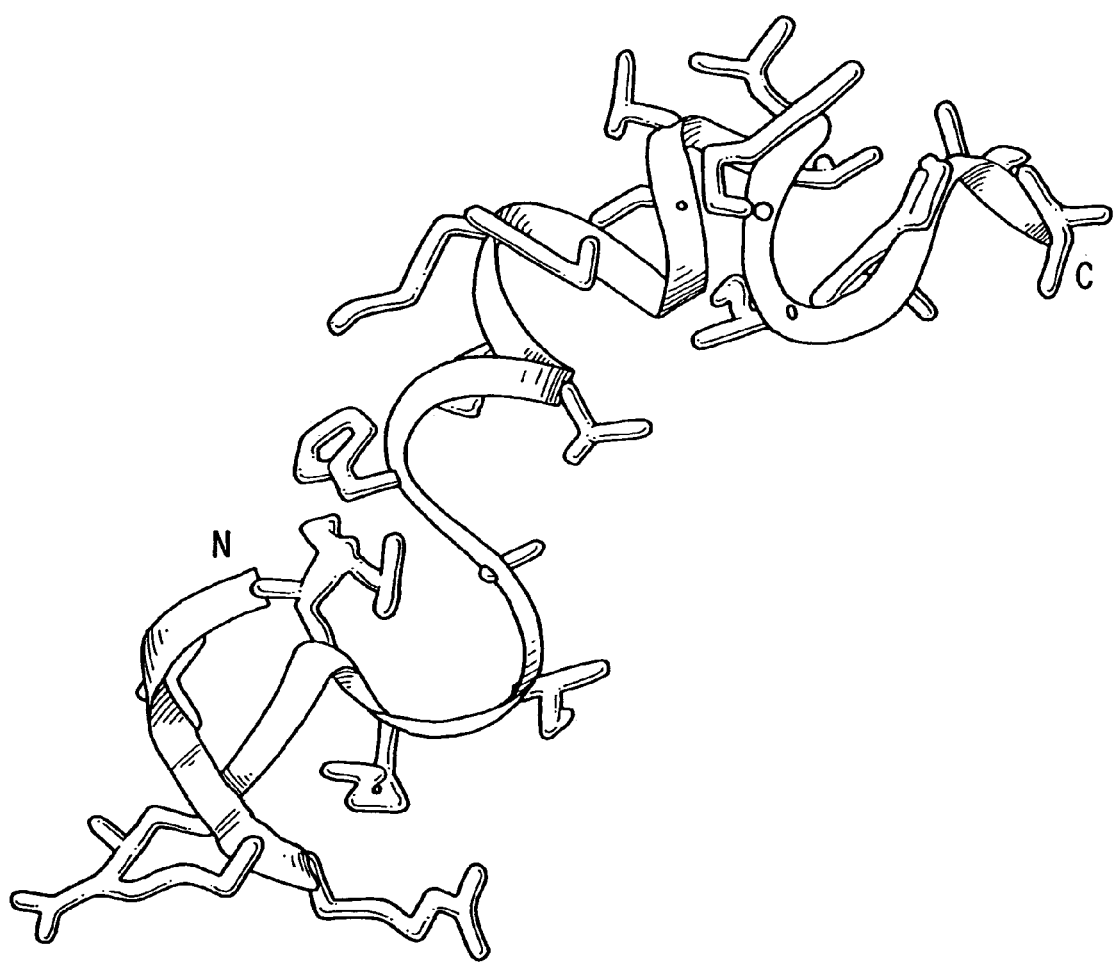
Figure 8:
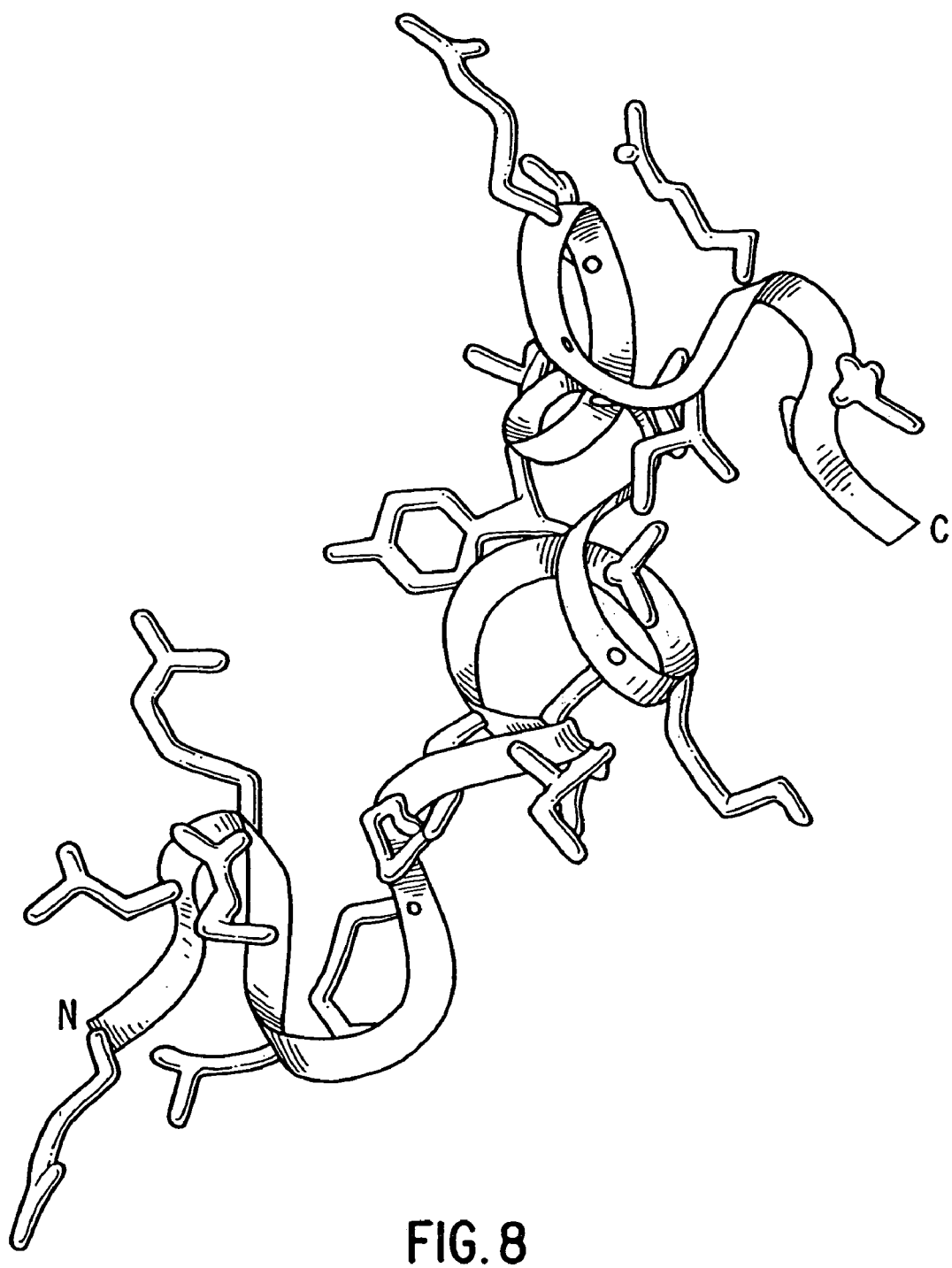

FIGS. 5A and 5B: Effects of CAP 18 (FIG. 5A) and SMAP 29 (FIG. 5B) peptides on human red blood cells. Erythrocytes were incubated with the indicated concentration of each peptide and hemolysis was measured as discussed in the Examples. Values are percent of control in the absence of antimicrobial peptide. Bars indicate mean±range, n=2; in some cases, the error bars are covered by the symbols.

Figures 2, 2A, 3, 4, 5, 6:
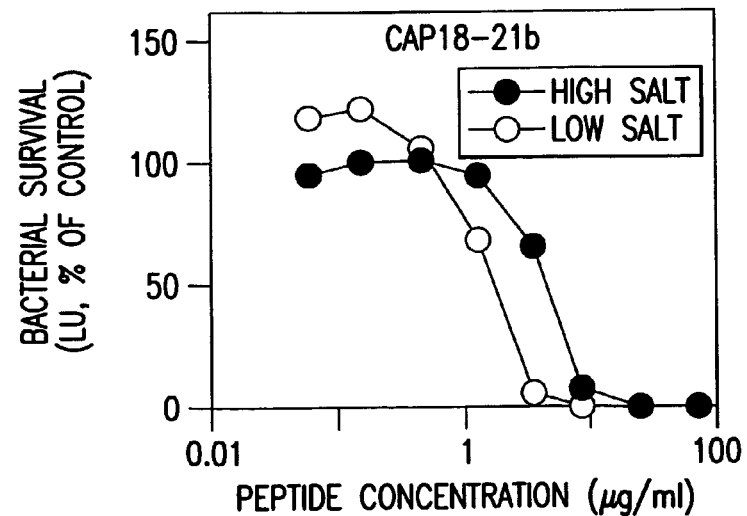
Figures 1, 2B:
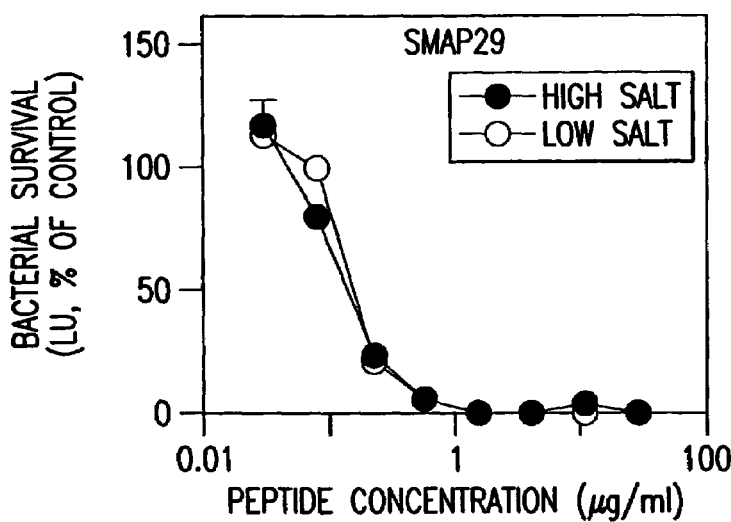
Figures 2, 2B:
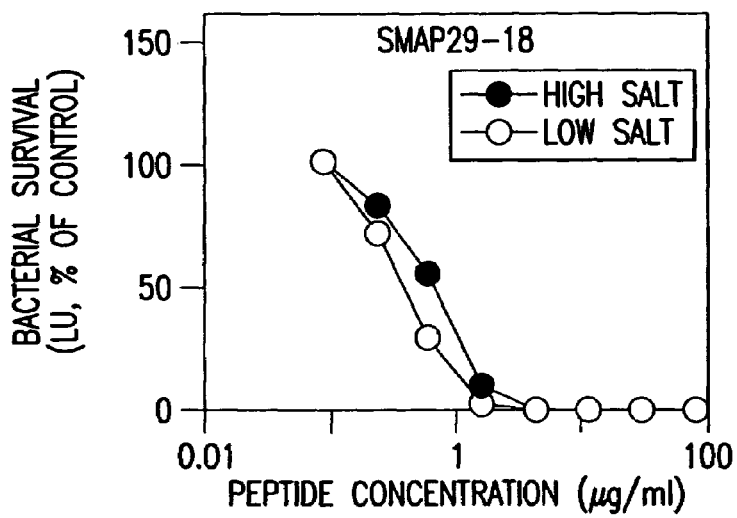
Figures 2, 2B, 3:
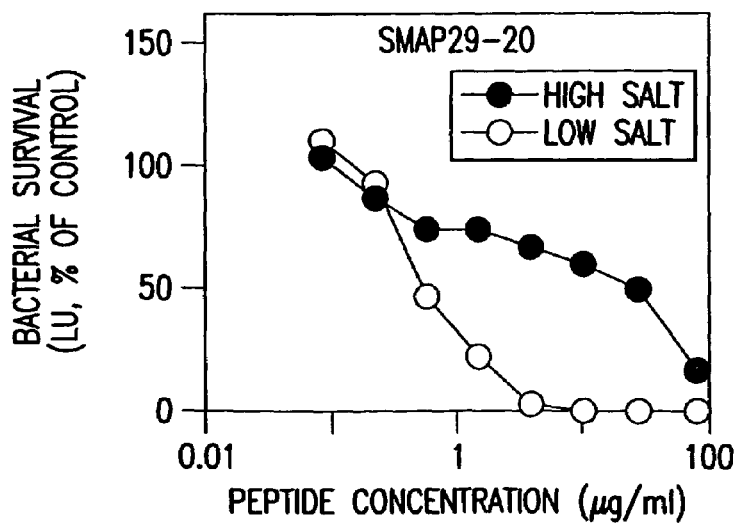
Figures 2, 2B, 3, 4:
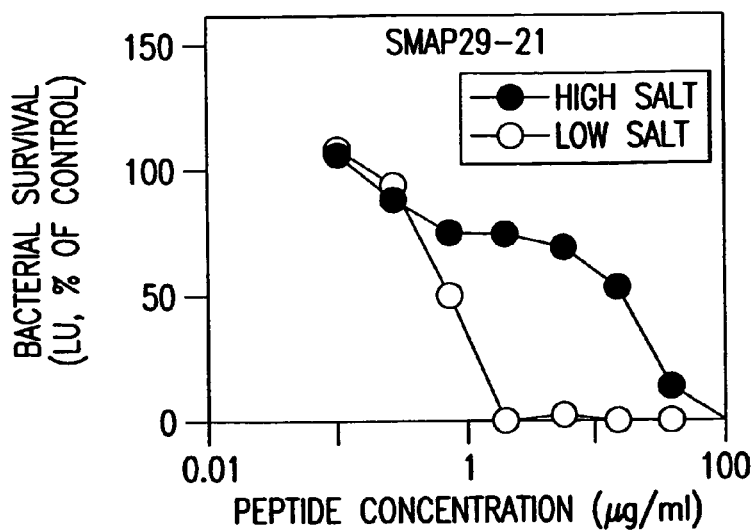
Figures 2, 2B, 3, 4, 5:
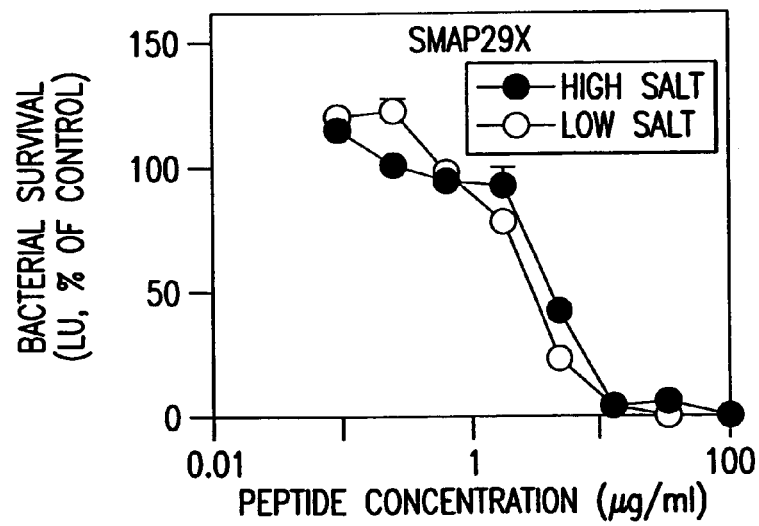
Figures 2, 2B, 3, 4, 5, 6:
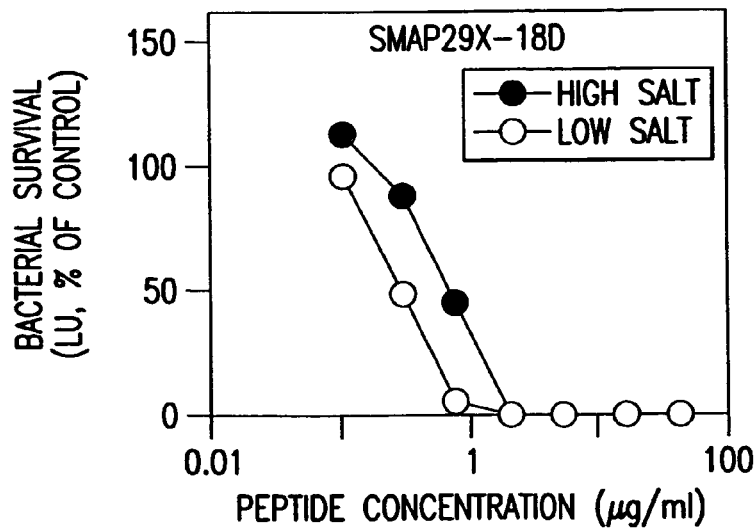

FIG. 6: Postmortem examination of the lungs of lambs infected with an ovine pneumonic isolate of *Pasturella haemolytica* and subsequently treated with SMAP 29. In infected lambs that did not receive SMAP 29 (Group 3), the pathologic gross lesions were higher than in the SMAP 29 treated group (Group 4) and the scores for microscopic lesions were also higher for the untreated group. SMAP 29 alone was well tolerated and did not induce significant changes at the pulmonary deposition site (Group 2).

Figures 2, 2B, 3, 4, 5, 6, 7:
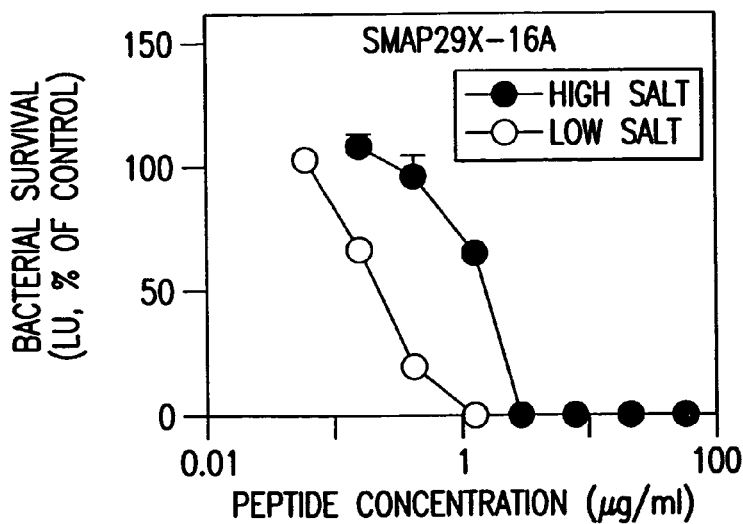

FIG. 7: Major Conformer A of Smap29 by 2D NMR.

Figures 2, 2B, 3, 4, 5, 6, 7, 8:
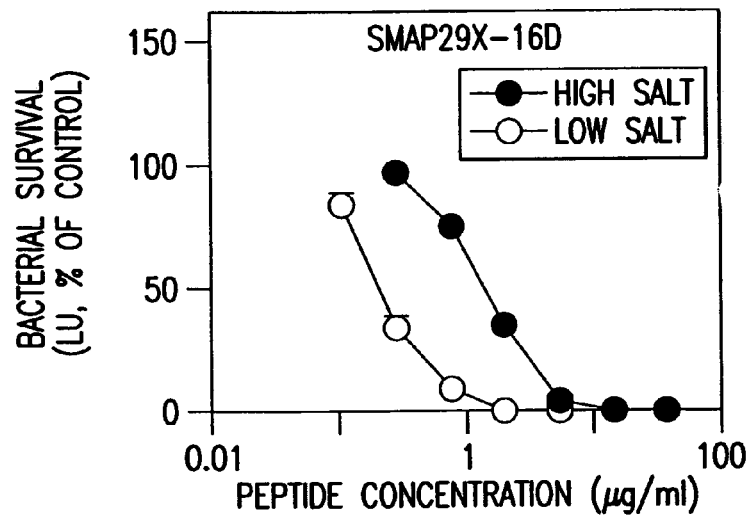

FIG. 8: Major Conformer B of Smap29 by 2D NMR.

Figures 2, 2B, 3, 4, 5, 6, 7, 8, 9:
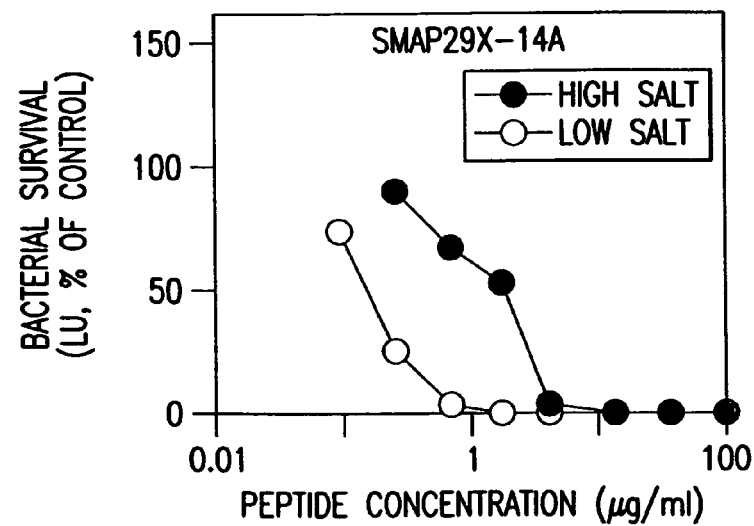

FIG. 9: Antimicrobial activity of SMAP-28 in 100 mM NaCl (Gram-positive bacteria).

Figures 2, 2B, 3, 4, 5, 6, 7, 8, 9, 10:
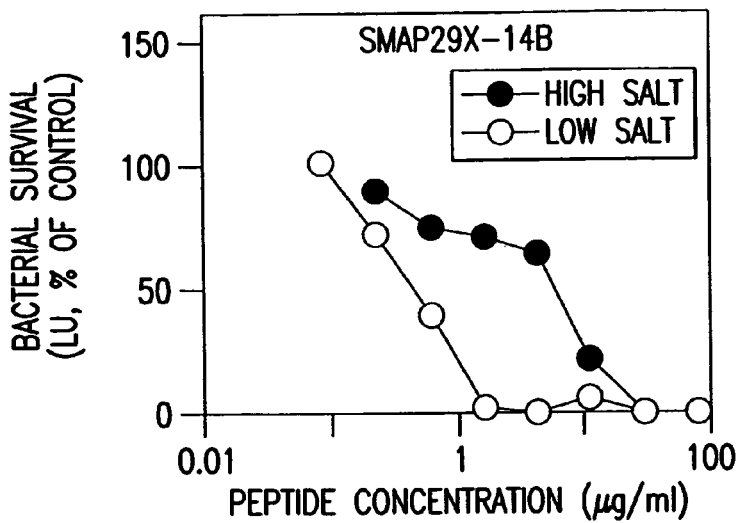
Figures 2, 2B, 3, 4, 5, 6, 7, 8, 9, 10, 11:
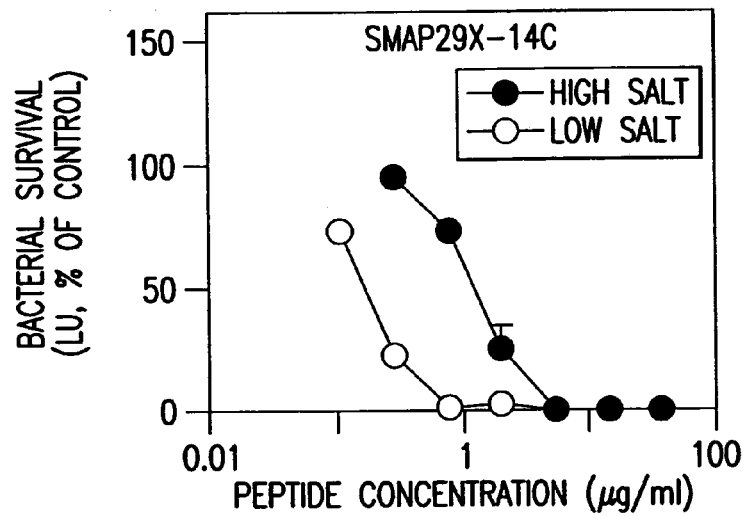
Figures 2, 2B, 3, 4, 5, 6, 7, 8, 9, 10, 11, 12:
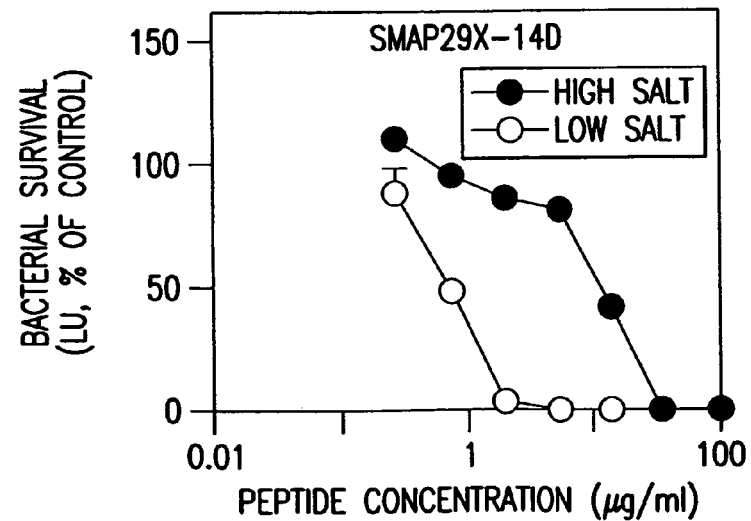

FIG. 10: Antimicrobial activity of SMAP-28 in 100 mM NaCl (Gram-negative bacteria)

DESCRIPTION OF ILLUSTRATIVE EMBODIMENTS

Although molecules with antibiotic properties have revolutionized medicine, increasingly their unrestrained use has led to the development of resistance in pathogenic strains. Therefore, in order to maintain the present standards of public health, new methods of controlling microbial infection must be devised.

Antimicrobial peptides of higher eukaryotes, though long recognized as components of the innate immune system, were initially considered primitive and of little clinical significance. However, the relative simplicity of these peptides belies their importance, not only in the prevention of primary microbial infection, but also in subsequent immunomodulation (Bowman, 1995). Further, the small size of the molecules suggests a decreased sensitivity to many of the mechanisms of microbial resistance.

Antimicrobial peptides are generally lethal to bacteria and some fungi. They exhibit differential toxicity towards mammalian cells (Hwang et al., 1998). While the mechanism of this action is not definitively known, it is nonetheless believed that the peptides interact with the lipid bilayer and may thus compromise the integrity of the bacterial membrane (Hwang P. et al. 1998).

SMAP 29 is an ovine antimicrobial peptide of the cathelicidin family originally identified through 3' RACE analysis of sheep bone marrow RNA (Mahoney, 1995; Bagella, 1995). RCAP 18 is a lupine antimicrobial peptide of the cathelicidin family originally identified from granulocytes (Hirata, 1994). The present invention arises, in one aspect, from the discovery of methods and compositions which capitalize upon unanticipated and unrecognized characteristics of these molecules.

It has been determined that the SMAP 29 and RCAP 18 peptides are suprisingly effective against bacterial strains previously determined to be resistant to one or more methods of control. More particularly, SMAP 29 compositions are capable of controlling infections by *Pseudomonas aeruginosa, Alcaligenes xylosoxidans,* and *Stenotrophomonas maltophila*, all strains previously exhibiting resistance to one or more conventional antibiotics. SMAP 29 and RCAP 18 are envisioned to be useful either alone or in combination with other antimicrobial agents or antibiotics in the control of, not only microbial strains normally susceptible to traditional antibiotics, but also those which have a recognized resistance to conventional therapies.

Further embodiments of the invention relate to truncated versions of the SMAP 29 and RCAP 18 peptides, which retain the bacteriostatic properties. It has been determined that the removal of certain terminal residues of these antimicrobial peptides does not profoundly effect the antimicrobial properties of the peptide. Thus, truncated peptides have been synthesized to determine what regions of the molecule are critical to antimicrobial function. Truncations include, for example, removal of the 8 C-terminal residues of the SMAP29 molecule (SEQ ID NO: 3), removal of the 4 C-terminal and the 5 N-terminal residues of the SMAP 29 molecule (SEQ ID NO: 4), and removal of the 11 N-terminal residues of the SMAP 29 molecule (SEQ ID NO: 5). Truncated RCAP 18 peptides with 18–22 amino acids retained activity against Gram-negative bacteria in high salt, but generally lost considerable activity against MRSA under these conditions.

While truncated peptides have utility in determining the active regions of the full peptide, they also are appropriate themselves for use in the control of microbial growth and proliferation. It is envisioned that those uses determined to be appropriate for the full SMAP29 and RCAP 18 molecules also are appropriate for the truncated versions of the molecules synthesized in specific embodiments of the invention.

As the important residues of the molecule were elicited, substitutions were envisioned which would maintain the bacteriostatic properties of such a peptide. Thus, this invention embodies synthesized peptides with a configuration related to that of SMAP 29 or RCAP 18, but possessing alternate structural properties deemed to maintain its antimicrobial characteristics. Alternate constructs, as set forth in SEQ ID NO: 1, 6–17 and 19–28, possess antimicrobial properties similar, but analogous or potentially superior to those exhibited by the SMAP 29 peptide or RCAP 18 peptide. There also is evidence that SMAPs and RCAPs can synergize with complement to increase cell killing.

The antibacterial potency of the full-length antimicrobial peptides correlated directly with the hydrophobicity gradient along their backbone, inversely with their relative abundance of anionic residues, and not with the extent of helix formation in trifluoroethanol. The impressive antipseudomonal and antistaphylococcal properties of SMAP 29 and RCAP 18, and the retention of activity in high salt solutions, suggests they, or derivatives thereof, will be effective therapeutic agents for bacterial infections on airway surfaces, for example, in patients with cystic fibrosis.

The antimicrobial potency of the disclosed molecules also translates to the ability to significantly attenuate the activity of viruses including retroviruses. Smap 29 has been demonstrated to have efficacy in reducing the activity of three retroviruses: namely HIV, HSV-1 and EIAV.

This invention thus encompasses methods to inhibit the microbial growth through the use of synthetic peptides demonstrated to have antimicrobial properties. It is contemplated that these peptides may be delivered into an environment in which bacteria are present or are likely to be present in order to control their growth and proliferation. It is further envisioned that such an environment would include a host organism. These embodiments, as well as others, are set forth in the following detailed description of the invention.

1. PEPTIDE PRODUCTION

A. Peptide Synthesis

The antimicrobial peptides envisioned in the instant invention may be chemically synthesized. An example of a method for chemical synthesis of such a peptide is as follows. Using the solid phase peptide synthesis method of Sheppard et al. (1981) an automated peptide synthesizer (Pharmacia LKB Biotechnology Co., LKB Biotynk 4170) adds N,N'-dicyclohexylcarbodiimide to amino acids whose amine functional groups are protected by 9-fluorenyl-methoxycarbonyl groups, producing anhydrides of the desired amino acid (Fmoc-amino acids). An Fmoc amino acid corresponding to the C-terminal amino acid of the desired peptide is affixed to Ultrosyn A resin (Pharmacia LKB Biotechnology Co.) through its carboxyl group, using dimethylaminopyridine as a catalyst. The resin is then washed with dimethylformamide containing iperidine resulting in the removal of the protective amine group of the C-terminal amino acid. A Fmoc-amino acid anhydride cooresponding to the next residue in the peptide sequence is then added to the substrate and allowed to couple with the unprotected amino acid affixed to the resin. The protective amine group is subsequently removed from the second amino acid and the above process is repeated with additional residues added to the peptide in a like manner until the sequence is completed. After the peptide is completed, the protective groups, other than the acetoamidomethyl group are removed and the peptide is released from the resin with a solvent consisting of, for example, 94% (by weight) trifluoroacetic acid, 5% phenol, and 1% ethaniol. The synthesized peptide is subsequently purified using high-performance liquid chromatography or other peptide purification technique discussed below.

In designing alternate peptide constructs with enhanced antimicrobial properties, substitutions may be used which modulate one or more properties of the molecule. Such variants typically contain the exchange of one amino acid for another at one or more sites within the peptide. For example, certain amino acids may be substituted for other amino acids in a peptide structure in order to enhance the interactive binding capacity of the structures. Since it is the interactive capacity and nature of a protein that defines that protein's biological functional activity, certain amino acid substitutions can be made in a protein sequence, and its underlying DNA coding sequence which potentially create a peptide with superior characteristics.

In making such changes, the hydropathic index of amino acids may be considered. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

Amino acid substitutions are generally based on the relative similarity of the amino acid side-chain substituents, for example, their hydrophobicity, hydrophilicity, charge, size, and the like but may nevertheless be made to highlight a particular property of the peptide. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

B. Fusion Proteins

The antimicrobial peptides of the instant application may be combined with fusion partners to produce fusion proteins. It is envisioned that such constructs might include combinations of an antimicrobial peptide with a partner also exhibiting some level of antimicrobial activity. Such a construct generally has all or a substantial portion of the native molecule, linked at the N- or C-terminus, to all or a portion of a second polypeptide. For example, fusions typically employ leader sequences from other species to permit the recombinant expression of a protein in a heterologous host. Another useful fusion includes the addition of an immunologically active domain, such as an antibody epitope, to facilitate purification of the fusion protein. Inclusion of a cleavage site at or near the fusion junction will facilitate removal of the extraneous polypeptide after purification if such removal is desired. Other useful fusions include linking of functional domains, such as active sites from enzymes, glycosylation domains, cellular targeting signals or transmembrane regions.

It is envisioned that, to construct fusion proteins, the cDNA sequence encoding the antimicrobial peptide would be linked to the cDNA sequence encoding the desired fusion partner. The antimicrobial peptide sequences disclosed in this application allow for the deduction of encoding DNA. Such sequences may be prepared using conventional techniques, and used as probes to recover corresponding DNA's from genomic or cDNA libraries. Following cloning, such DNA's can then be incorporated in appropriate expression vectors and used to transform host cells (e.g., bacterial or mammalian cells), which can be cultured to form recombinant antimicrobial peptides.

As used in this application, the term "an isolated nucleic acid encoding a antimicrobial peptide refers to a nucleic acid molecule that has been isolated free of total cellular nucleic acid. The term "functionally equivalent codon" is used herein to refer to codons that encode the same amino acid, such as the six codons for arginine or serine (Table 1, below), and also refers to codons that encode biologically equivalent amino acids, as discussed in the following pages.

TABLE 1

CODONS

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Typ | W | UGG | | | | | |
| Tyrosine | Tyr | Y | UAC | UAU | | | | |

Allowing for the degeneracy of the genetic code, sequences that have at least about 50%, usually at least about 60%, more usually about 70%, most usually about 80%, preferably at least about 90% and most preferably about 95% of nucleotides that are identical to the nucleotides of an antimicrobial peptide gene will be sequences that encompassed by the present invention. Nucleic acid sequences of the present invention may also be functionally defined as sequences that are capable of hybridizing to a nucleic acid segment encoding an antimicrobial peptide.

The DNA segments of the present invention include those encoding biologically functional equivalent antimicrobial peptides, as described above. Functionally equivalent proteins or peptides may be created via the application of recombinant DNA technology, in which changes in the protein structure may be engineered, based on considerations of the properties of the amino acids being exchanged, or as a result of natural selection. Changes designed by man may be introduced through the application of site-directed mutagenesis techniques or may be introduced randomly and screened later for the desired function.

C. Gene Therapy

In other embodiments, it is envisioned that antimicrobial peptides may be utilized in gene therapy. Individuals who are immunodeficient due to disease, injury or genetic defect may be the subject of gene therapy in which the genes for antimicrobial peptides are incorporated into host cells. To facilitate gene therapy, the cDNA for antimicrobial peptides must be incorporated into an expreession construct.

Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli is often transformed using derivatives of pBR322, a plasmid derived from an E. coli species. pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as E. coli LE392.

Further useful vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, the like.

Viral vectors are preferred eukaryotic expression systems. Included are adenoviruses, adeno-associated viruses, retroviruses, herpesviruses, poxviruses including vaccinia viruses and papilloma viruses including SV40.

(i) Regulatory Elements

Throughout this application, the term "expression construct" is meant to include any type of genetic construct containing a polynucleotide coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest.

In preferred embodiments, the nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term eukaryotic promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter employed to control the expression of a nucleic acid sequence of interest is not believed to be important, so long as it is capable of direction the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose.

By employing a promoter with well-known properties, the level and pattern of expression of the protein of interest following transfection or transformation can be optimized. Further, selection of a promoter that is regulated in response to specific physiologic signals can permit inducible expression of the gene product.

Enhancers are genetic elements that increase transcription from a promoter located at a distant position on the same molecule of DNA. Enhancers are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

(ii) Selectable Markers

In certain embodiments of the invention, the cells contain nucleic acid constructs of the present invention, a cell may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

(iii) Multigene Constructs and IRES

In certain embodiments of the invention, the use of internal ribosome binding sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picanovirus family (polio and encephalomyocarditis) have been described (Pelletier and Sonenberg, 1988), as well an IRES from a mammalian message (Macejak and Samow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

(iv) Host Cells and Delivery of Expression Vectors

Certain examples of prokaryotic hosts are *E. coli* strain RR1, *E. coli* LE392, *E. coli* B, *E. coli* X 1776 (ATCC No. 31537) as well as *E. coli* W3110 (F—, lambda-, prototrophic, ATCC No. 273325); bacilli such as *Bacillus* subtilis; and other enterobacteriaceae such as *Salmonella typhimurium, Serratia marcescens*, and various *Pseudomonas* species.

Primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented and are disclosed herein by reference (Freshner, 1992).

There are a number of ways in which expression vectors may introduced into cells. In certain embodiments of the invention, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubenstein, 1988; Temin, 1986).

One of the preferred methods for in vivo delivery involves the use of an adenovirus expression vector. "Adenovirus expression vector" is meant to include those constructs containing adenovirus sequences sufficient to (a) support packaging of the construct and (b) to express an antisense polynucleotide that has been cloned therein. In this context, expression does not require that the gene product be synthesized.

The expression vector comprises a genetically engineered form of adenovirus. Knowledge of the genetic organization of adenovirus, a 36 kb, linear, double-stranded DNA virus, allows substitution of large pieces of adenoviral DNA with foreign sequences up to 7 kb (Grunhaus & Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target cell range and high infectivity. Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MOI) (Mulligan, 1993).

Helper cell lines may be derived from human cells such as human embryonic 5 kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Racher et al. (1995) discloses improved methods for culturing 293 cells and propagating adenovirus. In one format, natural cell aggregates are grown by inoculating individual cells into 1 liter siliconized spinner flasks (Techne, Cambridge, UK) containing 100–200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 hours. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 hours.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al., (1986) or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$–$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact-sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al., recently introduced the chloramphenicol acetyltransferase (CAT) gene into duck hepatitis B virus genome in the place of the polymerase, surface, and pre-surface coding sequences. It was co-transfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

In order to effect expression of gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In still another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al., (1980) demonstrated the feasibility of liposome-mediated delivery and expression of foreign DNA in cultured chick embryo, HeLa and hepatoma cells. Nicolau et al., (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al., (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type such as lung, epithelial or tumor cells, by any number of receptor-ligand systems with or without liposomes. For example, epidermal growth factor (EGF) may be used as the receptor for mediated delivery of a nucleic acid encoding a gene in many tumor cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues.

D. Preparations

It is envisioned that the antimicrobial peptides and any second agents that might be delivered may be formulated and administered in any pharmacologically acceptable vehicle, such as parenteral, topical, aerosal, liposomal, nasal or ophthalmic preparations, with formulations designed for oral administration being currently preferred due to their ease of use. It is further envisioned that formulations antimicrobial peptides and any second agents that might be delivered may be formulated and administered in a manner that does not require that the be coupled with a pharmaceutically acceptable carrier. In those situations, it would be clear to one of ordinary skill in the art the types of diluents that would be proper for the proposed use of the peptides and any secondary agents required. Although further purification following synthesis may be desired, it is not necessarily required for use.

E. Protein Purification

Peptide purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic, immunologic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or HPLC.

Certain aspects of the present invention concern the purification, and in particular embodiments, the substantial purification, of an encoded peptide. The term "purified peptide" as used herein, is intended to refer to a composition, isolatable from other components, wherein the peptide is purified to any degree relative to its naturally-obtainable state. A purified peptide therefore also refers to a *peptide*, free from the environment in which it may naturally *occur*.

Generally, "purified" will refer to a peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more peptides in the composition. The term "purified to homogeneity" is used to mean that the composition has been purified such that there is single protein species based on the particular test of purity employed for example SDS-PAGE or HPLC.

Various methods for quantifying the degree of purification of the peptide will be known to those of skill in the art in light of the present disclosure. These include, for example, assessing the amount of peptides within a fraction by SDS/PAGE analysis.

There is no general requirement that the peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a peptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

2. THERAPEUTIC USES

This invention encompasses methods to reduce antimicrobial resistance, caused by any of the seven mechanisms described by Davies (1986) above, using an antimicrobial peptide and one or more antimicrobial agents or antibiotics. A list of bacterial strains that have developed antibiotic resistance by one or more of these mechanisms is listed in Table 2 (Lorian, 1991).

The peptides have broad spectrum antimicrobial properties effective against both Gram-positive and Gram-negative strains of bacteria and have been demonstrated to kill strains previously deemed multiply drug resistant. An attractive feature of these peptides is their tolerance for high salt concentrations. The peptides maintain activity in physiological salt solutions and thus are envisioned to be effective in the treatment lung diseases such as cystic fibrosis.

The bacteriocidal properties of the antimicrobial peptides disclosed in combination with their stability and insensitivity to high salt concentrations allow them to be included in formulations to inhibit microbial growth and proliferation. The purified antimicrobial peptide may be used without further modifications or it may be diluted in a pharmaceutically acceptable carrier. Because of the stability of the peptides it is contemplated that the invention may be administered to humans or animals, included in food preparations, pharmaceutical preparations, medicinal and pharmaceutical products, cosmetic products, hygienic products, cleaning products and cleaning agents, as well as any material to which the peptides could be sprayed on or adhered to wherein the inhibition of microbial growth on such a material is desired.

The proper dosage of an antimicrobial peptide necessary to prevent microbial growth and proliferation depends upon a number of factors including the types of bacteria that might be present, the environment into which the peptide is being introduced, and the time that the peptide is envisioned to remain in a given area.

It is further contemplated that the antimicrobial peptides of the invention may be used in combination with or to enhance the activity of other antimicrobial agents or antibiotics. Combinations of the peptide with other agents may be useful to allow antibiotics to be used at lower doses due to toxicity concerns, to enhance the activity of antibiotics whose efficacy has been reduced or to effectuate a synergism between the components such that the combination is more effective than the sum of the efficacy of either component independently. Antibiotics which may be combined with an antimicrobial peptide in combination therapy include but are not limited to penicillin, ampicillin, amoxycillin, vancomycin, cycloserine, bacitracin, cephalolsporin, imipenem, colistin, methicillin, streptomycin, kanamycin, tobramycin, gentamicin, tetracycline, chlortetracycline, doxycycline, chloramphenicol, lincomycin, clindamycin, erythromycin, oleandomycin, polymyxin nalidixic acid, rifamycin, rifampicin, gantrisin, trimethoprim, isoniazid, paraminosalicylic acid, and ethambutol. Table 3 (Reese and Betts, 1993), lists the antibiotics generally preferred for use against a given pathogenic bacterium. It is contemplated that the effectiveness of all the antibiotics listed in Table 3 will be increased upon combination with an antimicrobial peptide. Table 4 (Reese and Betts, 1993), itemizes the common pathogenic bacteria that are implicated in focal infections. The present invention is thus contemplated for use against all such infections.

TABLE 2

MECHANISMS OF RESISTANCE TO ANTIMICROBIAL AGENTS

| Antimicrobial Agent | Mechanisms Causing Resistance | Examples of Organisms |
|---|---|---|
| Aminoglycosides | Modifying enzymes: acetyltransferases, adenylyl-transferases (nucleotidyl-transferases), phosphotransferases | *Enterobacteriaceae, P. aeruginosa, S. aureus, E. faecalis* |
|  | Ribosomal resistance (streptomycin, spectinomycin) | *E. faecalis, Enterobacteriaceae, M. tuberculosis, P. aeruginosa* |
|  | Inadequate drug transport | *E. faecalis, P. aeruginosa,* anaerobes |
| β-Lactams | Enzymatic inactivation | *S. aureus, E. faecalis, Enterobacteriaceae, P. aeruginosa, Neisseria* spp., *H. influenzae* |
|  | Low affinity PBPs | *S. pneumoniae, N. gonorrhoeae, S. aureus,* |
|  | Lack of penetration through outer membrane | *P. aeruginosa, P. aeruginosa, Enterobacteriaceae* |
| Chloramphenicol | Acetylation | *Enterobacteriaceae, S. aureus,* streptococci, *Bacteroides uniformis* |
|  | Lack of penetration | *P. aeruginosa* |
| Clindamycin, erythromycin, lincomycin | Ribosomal resistance due to methylation of rRNA | Streptococci, *E. faecalis,* |
|  | Inactivation by esterase | *Enterobacteriaceae* |
|  | Decreased penetration | *Enterobacteriaceae S. hominis* |
| Fluoroquinolones | Decreased uptake | *Enterobacteriaceae, P. aeruginosa,* staphylococci |
|  | Altered target site (DNA gyrase) | *Enterobacteriaceae, P. aeruginosa* |
| Lincomycin | Inactivation | *S. aureus* |
| Sulfonamides | Synthesis of an altered or alternative target site (dihydropteroate synthetase) | *Enterobacteriaceae, Neisseria* spp., *P. aeruginosa* |
|  | Lack of penetration | Anaerobes |
|  | Overproduction of PABA | *Neisseria, S. aureus* |
| Tetracycline | Drug efflux | *Enterobacteriaceae,* staphylococci, streptococci |
|  | Protection of ribosome from tetracycline | Streptococci, *E. faecalis, Neisseria* spp., *Mycoplasma* spp. |
|  | Inactivation | Cryptic gene found in *B. fragilis,* expressed resistance in *E. coli* |
| Trimethoprim | Synthesis of an altered or alternative target site (dihydrofolate reductase) | *Enterobacteriaceae, V. cholerae,* staphylococci |
|  | Lack of penetration | *P. aeruginosa* |

TABLE 2-continued

MECHANISMS OF RESISTANCE TO ANTIMICROBIAL AGENTS

| Antimicrobial Agent | Mechanisms Causing Resistance | Examples of Organisms |
|---|---|---|
| | Ability to use alternative pathway | Enterococci H. influenzae |
| | Overproduction of dihydrofolate reductase | |
| Vancomycin | ? | Pediococci, Leuconostoc spp. (intrinsic) |
| | ?Blocking of target site | Enterococci (acquired) |

TABLE 3

ANTIBIOTICS OF CHOICE FOR COMMON PATHOGENS

| Pathogen | Antibiotic of First Choice[a] | Alternative Agents[a] |
|---|---|---|
| Gram-positive cocci | | |
| Staphylococcus aureus or S. epidermidis | Penicillin | A first-generation cephalosporin, vancomycin, imipenem, or clindamycin; a fluoroquinolone[b] |
| Non-penicillinase-producing | Penicillinase-resistant penicillin (e.g., oxacillin or nafcillin) | A first-generation cephalosporin, vancomycin, clindamycin, imipenem, amoxicillin-clavulanic acid, ticarcillin-clavulanic acid, ampicillin-sulbactam; a fluoroquinolone[b] TMP-SMZ, minocycline |
| Penicillinase-producing | | |
| Methicillin-resistant | Vancomycin with or without gentamicin and/or rifampin | |
| Streptococci Group A, C, G | Penicillin | A cephalosporin[a], vancomycin, erythromycin; clarithromycin; azithromycin; clindamycin |
| Group B | Penicillin (or ampicillin) | A cephalosporin[a], vancomycin, or erythromycin |
| Enterococcus | | |
| Endocarditis or other serious infection | Penicillin (or ampicillin) with gentamicin | Vancomycin with gentamicin |
| Uncomplicated urinary tract infection | Ampicillin or amoxicillin | A fluoroquinolone, nitrofurantoin |
| Viridans group | Penicillin G (with or without gentamicin) | A cephalosporin[a], vancomycin |
| S. bovis | Penicillin G | A cephalosporin[a], vancomycin |
| S. pneumoniae | Penicillin G | A cephalosporin[a], erythromycin, chloramphenicol, vancomycin |
| Gram-negative cocci | | |
| Neisseria gonorrhoeae | Ceftriaxone | Spectinomycin, a fluoroquinolone, cefoxitin, cefixime, cefotaxime (see Appendix E) |
| N. meningitidis | Penicillin G | Third-generation cephalosporin, chloramphenicol |
| Moraxella (Branhamella) catarrhalis | TMP-SMZ | Amoxicillin-clavulanic acid; an erythromycin; clarithromycin azithromycin, cefuroxime, cefixime, third-generation cephalosporin, tetracycline |
| Gram-positive bacilli | | |
| Clostridium perfringens (and Clostridium sp.) | Penicillin G | Chloramphenicol, metronidazole, or clindamycin |

TABLE 3-continued

ANTIBIOTICS OF CHOICE FOR COMMON PATHOGENS

| Pathogen | Antibiotic of First Choice[a] | Alternative Agents[a] |
|---|---|---|
| Listeria monocytogenes | Ampicillin with or without gentamicin | TMP-SMZ |
| Gram-negative bacilli | | |
| Acinetobacter | Imipenem | Tobramycin, gentamicin, or amikacin, usually with ticarcillin or piperacillin (or similar agent); TMP-SMZ |
| Aeromonas hydrophila | TMP-SMZ | Gentamicin, tobramycin; imipenem; a fluoroquinolone |
| Bacteroides Bacteroides sp. (oropharyngeal) | Penicillin G | Clindamycin, cefoxitin, metronidazole, chloramphenicol, cefotetan, ampicillin-sulbactam |
| B. fragilis strains (gastrointestinal strains) | Metronidazole | Clindamycin; ampicillin-sulbactam; imipenem; cefoxitin[c]; cefotetan[c]; ticarcillin-clavulanic acid; piperacillin[c]; chloramphenicol; cefmetazole[c] |
| Campylobacter fetus, jejuni | A fluoroquinolone (adults) or an erythromycin | A tetracycline, gentamicin |
| Enterobacter sp. | Imipenem | An aminoglycoside and piperacillin or ticarcillin or mezlocillin; a third-generation cephalosporin[d]; TMP-SMZ; aztreonam; a fluoroquinolone |
| Escherichia coli Uncomplicated urinary tract infection | TMP-SMZ | A cephalosporin or a fluoroquinolone |
| Recurrent or systemic infection | A cephalosporin[e] | Ampicillin with or without an aminoglycoside, TMP-SMZ, oral fluoroquinolones useful in recurrent infections, ampicillin-sulbactam, ticarcillin-clavulanic acid, aztreonam |
| Haemophilus influenzae (coccobacillary) | Cefotaxime or ceftriaxone | Chloramphenicol; cefuroxime for pneumonia) |
| Life-threatening infections | TMP-SMZ | Ampicillin or amoxicillin; cefuroxime; a sulfonamide with or without an erythromycin; cefuroxime-axetil; third-generation cephalosporin, amoxicillin-clavulanic acid, cefaclor, tetracycline; clarithromycin; azithromycin |
| Upper respiratory infections and bronchitis | | |
| Klebsiella pneumoniae | A cephalosporin[e] | An aminoglycoside, imipenem, TMP-SMZ, ticarcillin-clavulanic acid, ampicillin-sulbactam, aztreonam, a fluoroquinolone; amoxicillin-clavulanic acid |
| Legionella spp. | Erythromycin with rifampin | TMP-SMZ; clarithromycin; azithromycin; ciprofloxacin |
| Pasteurella multocida | Penicillin G | Tetracycline, cefuroxime, amoxicillin-clavulanic acid, ampicillin-sulbactam |
| Proteus sp. | Cefotaxime, ceftizoxime, or ceftriaxone[f] | An aminoglycoside; ticarcillin or piperacillin or mezlocillin; TMP-SMZ; amoxicillin-clavulanic acid; ticarcillin-clavulanic acid, ampicillin-sulbactam; a fluoroquinolone; aztreonam; imipenem |

TABLE 3-continued

ANTIBIOTICS OF CHOICE FOR COMMON PATHOGENS

| Pathogen | Antibiotic of First Choice[a] | Alternative Agents[a] |
|---|---|---|
| *Providencia stuartii* | Cefotaxime, ceftizoxime, or ceftriaxone[f] | Imipenem; an aminoglycoside often combined with ticarcillin or piperacillin or similar agent; ticarcillin-clavulanic acid; TMP-SMZ, a fluoroquinolone; aztreonam |
| *Pseudomonas aeruginosa* (nonurinary tract infection) | Gentamicin or tobramycin or amikacin (combined with ticarcillin, piperacillin, etc. for serious infections) | An aminoglycoside and ceftazidime; imipenem, or aztreonam plus an aminoglycoside; ciprofloxacin |
| (urinary tract infections) | Ciprofloxacin | Carbenicillin; ticarcillin, piperacillin, or mezlocillin; ceftazidime; imipenem; aztreonam; an aminoglycoside |
| *Pseudomonas cepacia* | TMP-SMZ | Ceftazidime, chloramphenicol |
| *Salmonella typhi* | Ceftriaxone | Ampicillin, amoxicillin, TMP-SMZ, chloramphenicol; a fluoroquinolone |
| Other species | Cefotaxime or ceftriaxone | Ampicillin or amoxicillin, TMP-SMZ, chloramphenicol; a fluoroquinolone |
| *Serratia* | Cefotaxime, ceftizoxime, or ceftriaxone[f] | Gentamicin or amikacin; imipenem; TMP-SMZ; ticarcillin, piperacillin, or mezlocillin; aztreonam; a fluoroquinolone |
| *Shigella* | A fluoroquinolone | TMP-SMZ; ceftriaxone; ampicillin |
| *Vibrio cholerae* (chlorea) | A tetracycline | TMP-SMZ; a fluoroquinolone |
| *Vibrio vulnificus* | A tetracycline | Cefotaxime |
| *Xanthomonas* (*Pseudomonas*) *maltophilia* | TMP-SMZ | Minocycline, ceftazidime, a fluoroquinolone |
| *Yersinia enterocolitica* | TMP-SMZ | A fluoroquinolone; an aminoglycoside; cefotaxime or ceftizoxime |
| *Yersinia pestis* (plague) | Streptomycin | A tetracycline; chloramphenicol; gentamicin |

Key: TMP-SMZ = trimethoprim-sulfamethoxazole.
[a] Choice presumes susceptibility studies indicate that the pathogen is susceptible to the agent.
[b] The experience with fluoroquinolone use in *staphylococcal* infections is relatively limited. The fluoroquinolones should be used only in adults.
[c] Up to 15–20% of strains may be resistant.
[d] *Enterobacter* spp. may develop resistance to the cephalosporins.
[e] Specific choice will depend on susceptibility studies. Third-generation cephalosporins may be exquisitely active against many Gram-negative bacilli (e.g., *E. coli, Klebsiella* sp.). In some geographic areas, 20–25% of community-acquired *E. coli* infections may be resistant to ampicillin (amoxicillin).
[f] In severely ill patients, this is often combined with an aminoglycoside while awaiting susceptibility data.

Key: TMP-SMZ=trimethoprim-sulfamethoxazole.

[a] Choice presumes susceptibility studies indicate that the pathogen is susceptible to the agent.

[b] The experience with fluoroquinolone use in staphylococcal infections is relatively limited. The fluoroquinolones should be used only in adults.

[c] Up to 15–20% of strains may be resistant.

[d] *Enterobacter* spp. may develop resistance to the cephalosporins.

[e] Specific choice will depend on susceptibility studies. Third-generation cephalosporins may be exquisitely active against many Gram-negative bacilli (e.g., *E. coli, Klebsiella* sp.). In some geographic areas, 20–25% of community-acquired *E. coli* infections may be resistant to ampicillin (amoxicillin).

[f] In severely ill patients, this is often combined with an aminoglycoside while awaiting susceptibility data.

TABLE 4

COMMON PATHOGENS IN FOCAL INFECTIONS

| Presumed location of Infection | Common pathogens | Gram stain Characteristics of exudate-if available |
|---|---|---|
| Urinary tract infections | Community-acquired: *Escherichia coli* | GNB |
|  |  | GNB |
|  | Recurrent or nosocomial: *E. coli: Klebsiella, Proteus, Pseudomonas* sp. *Enterococci* | GPC |
| Intravenous catheter phlebitis and/or sepsis | *Staphylococcus aureus* or *S. epidermidis* | GPC |
|  | *Klebsiella, Enterobacter, Pseudomonas* sp. | GNB |
| Peripheral catheter Hyperalimentation line | *Candida* sp., *S. aureus, S. epidermidis*, enterococci | Budding yeast; |
|  | *Klebsiella, Enterobacter* sp., etc. | GPC GNB |
| Arteriovenous shunt | *S. aureus, S. epidermidis* | GPC |
| Septic bursitis | *S. aureus* | GPC |
| Biliary tract | *E. coli, Klebsiella* sp., and enterococci; *Bacteroides fragilis* (in elderly patients), *Clostridia* sp. |  |
| Intra-abdominal abscess, peritonitis, or large bowel perforation; diverticulitis[a] | *E. coli* | GNB |
|  | *B. fragilis* | GNB |
|  | *Klebsiella* sp. | (thin, irregularly stained) |
|  | (*Enterococci*) | GNB |
|  |  | GPC |
| Burn wounds | Early: *S. aureus*, streptococci |  |
|  | Later: Gram-negative *bacilli*, fungi |  |
| Cellulitis, wound and soft tissue infections | *S. aureus* | GPC |
|  | Streptococci | GPC |
|  | *Clostridium* sp. | GPB |
| Meningitis | See Appendix C |  |
| Pneumonia | See Appendix D |  |
| Pelvic abscess, postabortal or postpartal | Anaerobic streptococci | GPC |
|  | *B. fragilis* | GNB (thin, irregularly stained) |
|  | *Clostridium* sp. | GPB |
|  | *E. coli* | GNB |
|  | Enterococci | GPC |
| Septic arthritis | *S. aureus* | GPC |
|  | *Haemophilus influenzae* (in children younger than 6 yr) | GNC |
|  | Group B *streptococci* (in neonates) | GPC |
|  | Gram-negative organisms[b] | GNB |

TABLE 4-continued

COMMON PATHOGENS IN FOCAL INFECTIONS

| Presumed location of Infection | Common pathogens | Gram stain Characteristics of exudate-if available |
|---|---|---|
| Acute osteomyelitis | S. aureus | GPC |
| | H. influenzae (in children younger than 6 yr) | GNC |
| | Group B streptococci (in neonates) | GPC |
| | Gram-negative organisms[b] | GNB |

Key: GNB = Gram-negative bacilli; GPC = Gram-positive cocci; GPB = Gram-positive bacilli; GNC = Gram-negative coccobacilli.
[a]The precise role of enterococci in intra-abdominal infections is unclear. In mild to moderate infections, it may not be necessary to provide antibiotic activity against enterococci.
[b]In high-risk patients (e.g., immunocompromised, elderly, IV drug abusers, diabetics, debilitated patients).

Key: GNB=Gram-negative bacilli; GPC=Gram-positive cocci; GPB=Gram-positive bacilli; GNC=Gram-negative coccobacilli.

[a]The precise role of enterococci in intra-abdominal infections is unclear.

In mild to moderate infections, it may not be necessary to provide antibiotic activity against enterococci.

[b]In high-risk patients (e.g., immunocompromised, elderly, IV drug abusers, diabetics, debilitated patients).

A. Dosage

To reduce the resistance of a microorganism to an antimicrobial agent, as exemplified by reducing the resistance of a bacterium to an antibiotic, or to kill a microorganism or bacterium, one would generally contact the microorganism or bacterium with an effective amount of the antibiotic or antimicrobial agent in combination with an amount of an antimicrobial peptide effective to inhibit growth of the microorganism or bacterium. In terms of killing or reducing the resistance of a bacterium, one would contact the bacterium with an effective amount of an antibiotic in combination with an amount of an antimicrobial peptide effective to inhibit growth and/or proliferation in the bacterium. The terms "microorganism" and "bacterium" are used for simplicity and it will be understood that the invention is suitable for use against a population of microorganisms, i.e., "bacteria".

The microorganism, e.g., bacterium, or population thereof, may be contacted either in vitro or in vivo. Contacting in vivo may be achieved by administering to an animal (including a human patient) that has, or is suspected to have a microbial or bacterial infection, a therapeutically effective amount of pharmacologically acceptable antimicrobial peptide formulation in alone or in combination with a therapeutic amount of a pharmacologically acceptable formulation of a antibiotic agent. The invention may thus be employed to treat both systemic and localized microbial and bacterial infections by introducing the combination of agents into the general circulation or by applying the combination, e.g., topically to a specific site, such as a wound or burn, or to the eye, ear or other site of infection.

Where an antimicrobial peptide is used in combination with other antimicrobial agents or antibiotics, an "effective amount of an antimicrobial agent or antibiotic" means an amount, or dose, within the range normally given or pre scribed. Such ranges are well established in routine clinical practice and will thus be known to those of skill in the art. Appropriate oral and parenteral doses and treatment regimens are further detailed herein in Table 5 and Table 6. As this invention provides for enhanced microbial and/or bacterial killing, it will be appreciated that effective amounts of an antimicrobial agent or antibiotic may be used that are lower than the standard doses previously recommended when the antimicrobial or antibiotic is combined with a antimicrobial peptide.

Naturally, in confirming the optimal therapeutic dose for antimicrobial peptides, first animal studies and then clinical trials would be conducted, as is routinely practiced in the art. Animal studies are common in the art and are further described herein (Example II) and in publications such as Lorian (1991, pp. 746–786, incorporated herein by reference) and Cleeland and Squires (incorporated herein by reference, from within the Lorian text).

The $ID_{50}/IC_{50}$ ratio required for safe use of the proposed inhibitor-antimicrobial peptide or combinations of peptide with other antimicrobial agents will be assessed by determining the $ID_{50}$ (median lethal toxic dosage) and the $IC_{50}$ (median effective therapeutic dosage) in experimental animals. The optimal dose for human subjects is then defined by fine-tuning the range in clinical trials. In the case of $ID_{50}$, the inhibitor is usually administered to mice or rats (orally or intraperitoneal) at several doses (usually 4–5) in the lethal rage. The dose in mg/kg is plotted against % mortality and the dose at 50% represents the $ID_{50}$ (Klaassen, 1990). The $IC_{50}$ is determined in a similar fashion as described by Cleeland and Squires (1991).

In a clinical trial, the therapeutic dose would be determined by maximizing the benefit to the patient, whilst minimizing any side-effects or associated toxicities. Throughout the detailed examples, various therapeutic ranges are listed. Unless otherwise stated, these ranges refer to the amount of an agent to be administered orally.

In optimizing a therapeutic dose within the ranges disclosed herein, one would not use the upper limit of the range as the starting point in a clinical trial due to patient heterogeneity. Starting with a lower or mid-range dose level, and then increasing the dose will limit the possibility of eliciting a toxic or untoward reaction in any given patient or subset of patients. The presence of some side-effects or certain toxic reactions per se would not, of course, limit the utility of the invention, as it is well known that most beneficial drugs also produce a limited amount of undesirable effects in certain patients. Also, a variety of means are available to the skilled practitioner to counteract certain side-effects, such as using vitamin $B_{12}$ in association with $N_2O$ treatment (Ostreicher, 1994).

Zak and Sande (1981) reported on the correlation between the in vitro and in vivo activity of a 1000 compounds that were randomly screened for antimicrobial activity. The important finding in this study is that negative in vitro data is particularly accurate, with the negative in vitro results showing more than a 99% correlation with negative in vivo activity. This is meaningful in the context of the present invention as one or more in vitro assays will be conducted prior to using any given combination in a clinical setting. Any negative result obtained in such an assay will thus be of value, allowing efforts to be more usefully directed.

In the treatment of animals or human patients with combination therapy, there are various appropriate formulations and treatment regimens that may be used. For example, the antimicrobial peptide and second agent(s) may be administered to an animal simultaneously, e.g., in the form of a single composition that includes the antimicrobial peptide and second agent, or by using at least two distinct compositions. The antimicrobial agent could also be administered to the animal prior to the second agent or the second agent may be given prior to the antimicrobial peptide.

Multiple combinations may also be used, such as more than one antimicrobial peptide used with one second agent or more than one second agent. Different classes second agents and antimicrobial peptides may be combined, naturally following the general guidelines known in the art regarding drug interactions. Typically, between one and about five distinct antimicrobial agents are contemplated for use along with between one and about six antimicrobial peptides.

Further embodiments of the invention include therapeutic kits that comprise, in suitable container means, a pharmaceutical formulation of at least one antimicrobial peptide and a pharmaceutical formulation of at least one antimicrobial agent or antibiotic. The antimicrobial peptide and antimicrobial agent or antibiotic may be contained within a single container means, or a plurality of distinct containers may be employed.

Depending on the circumstances, antimicrobial agents may be employed in oral or parenteral treatment regimens. Appropriate doses are well known to those of skill in the art and are described in various publications, such as (Reese and Betts, 1993; incorporated herein by reference). Table 5 and Table 6 (taken from Reese and Betts, 1993) are included herein to provide ready reference to the currently recommended doses of a variety of antimicrobial agents.

Following are definitions of terms that are used in Table 5 and Table 6: qid (4 times daily), tid (3 times daily), bid (twice daily), qd (once daily), q4h (every 4 hours around the clock), q6h (every 6 hours around the clock) and q8h (every 8 hours around the clock).

TABLE 5

COMMON ANTIBIOTICS AND USUAL ORAL DOSES

| ANTIBIOTIC | DOSAGE |
|---|---|
| Penicillin V | 2 |
| Rugby (generic) | 50 mg qid |
| V-cillin K | |
| Dicloxacillin | 250 mg qid |
| Glenlawn (generic) | |
| Dynapen | |
| Cloxacillin (Tegopen) | 250 mg qid |
| Amoxicillin | 250 mg tid |
| Rugby (generic) | |
| Polymox | |
| Ampicillin | 250 mg qid |
| Moore (generic) | |
| Polycillin | |
| Augmentin | tid |
| 250-mg tablets | |
| chewables (250 mg) | |
| 125-mg (suspension) | |
| chewables (125 mg) | |
| Carbenicillin (Geocillin) | 382 mg qid (1 tb) |
| | 2 tab qid |
| Cephalexin | 250 mg qid |
| Rugby (generic) | |
| Keflex | |
| Rugby (generic) | 500 mg qid |
| Keflex | |
| Cefadroxil | 1 gm bid |
| Rugby (generic) | |
| Duricef | |

TABLE 5-continued

COMMON ANTIBIOTICS AND USUAL ORAL DOSES

| ANTIBIOTIC | DOSAGE |
|---|---|
| Cephradine | 250 mg qid |
| Rugby (generic | 500 mg qid |
| Velosef | |
| Rugby (generic) | |
| Velosef | |
| Cefaclor | 250 mg tid |
| Ceclor | |
| Cefuroxime axetil | 125 mg bid |
| Ceftin | 250 mg bid |
| | 500 mg bid |
| Cefixime | 400 mg q24h |
| Suprax | |
| Cefprozil | 250 mg q12h |
| Cefzil | |
| Loracarbef (Lorabid) | 200 mg bid |
| Cefpodoxime proxetil | 200 mg bid |
| (Vantin) | |
| Clindamycin | 300 mg q8h |
| Cleocin | |
| TMP/SMZ | 1 double-strength bid |
| Bactrim | |
| Septra | |
| (generic) | |
| Trimethoprim | 100 mg bid |
| Rugby (generic) | |
| Proloprim | |
| Erythromycin (base) | 250 mg qid |
| Abbott | |
| E-mycin (delayed release) | |
| Erythromycin stearate | 250 mg qid |
| Rugby (generic) | |
| Azithromycin | 1 g once only 500 mg, |
| Zithromax | day 1, plus 250 mg, day 2–5 |
| Clarithromycin | 250 mg bid |
| Biaxin | 500 mg bid |
| Tetracycline hydrochloride | 250 mg qid |
| Mylan | |
| Sumycin 250 | |
| Doxycycline | 100 mg qd (with 200- |
| Lederle (generic) | mg initial load) |
| Vibramycin | |
| Vancomycin | Capsules |
| Vancocin HCl (oral | 125 mg q6h PO |
| soln/powder) | |
| Metronidazole | 250 mg qid |
| Rugby (generic) | |
| Flagyl | |
| Norfloxacin | 400 mg bid |
| Noroxin | |
| Ciprofloxacin | 250 mg bid |
| Cipro | 500 mg bid |
| | 750 mg bid |
| Ofloxacin | 200 mg bid |
| Floxin | 300 mg bid |
| | 400 mg bid |
| Lomefloxacin Maxaquin | 400 mg once qd |

TABLE 6

COMMON ANTIBIOTICS AND USUAL PARENTERAL DOSES

| ANTIBIOTIC | DOSAGE |
|---|---|
| Penicillin G | 2,400,000 units |
| Pfizerpen G (Pfizer) | 12 million units |
| Oxacillin | 12 g |
| Prostaphlin (Bristol) | |
| Nafcillin | 12 g |
| Nafcil (Bristol) | |
| Ampicillin | 6 g |
| Omnipen (Wyeth) | |

TABLE 6-continued

COMMON ANTIBIOTICS AND USUAL PARENTERAL DOSES

| ANTIBIOTIC | DOSAGE |
|---|---|
| Ticarcillin | 18 g |
| Ticar (Beecham) | |
| Piperacillin | 18 g |
| Pipracil (Lederle) | 16 g |
| Mezlocillin | 18 g |
| Mezlin (Miles) | 16 g |
| Ticarcillin-clavulanate | 18 g/0.6 g |
| Timentin (Beecham) | 12 g/0.4 g |
| Ampicillin-sulbactam | 6 g |
| Unasyn (Roerig) | 12 g |
| Cephalothin | 9 g (1.5 g q4h) |
| Keflin (Lilly) | |
| Cefazolin | 4 g (1 g q6h) |
| Ancef (SKF) | 3 g (1 g q8h) |
| Cefuroxime | 6 g 2.25 g (750 mg q8h) |
| Zinacef (Glaxo) | 4.5 g (1.5 g q8h) |
| Cefamandole | 9 g (1.5 g q4h) |
| Mandol (Lilly) | |
| Cefoxitin | 8 g (2 g q6h) |
| Mefoxin (MSD) | 6 g (2 g q8h) |
| Cefonicid | 1 g q12h |
| Monicid (SKF) | |
| Cefotetan | 2 g q12h |
| Cefotan (Stuart) | |
| Cefmetazole | 2 g q8h |
| Zefazone (Upjohn) | |
| Ceftriaxone | 2 g (2.0 g q24h) |
| Rocephin (Roche) | 1 g (1.0 g q24h) |
| Ceftazidime | 6 g (2 g q8h) |
| Fortax (Glaxo) | |
| Taxicef (SKF) | |
| Tozidime (Lilly) | |
| Cefotaxime | 2 g q6h |
| Claforan (Hoechst) | 2 g q8h |
| Cefoperazone | 8 g (2 g q6h) |
| Cefobid (Pfizer) | 6 g (2 g q8h) |
| Ceftizoxime | (2 g q8h) |
| Ceftizox (SKF) | |
| Aztreonam | 2 g q8h |
| Azactam (Squibb) | 1 g q8h |
| Imipenem | 2000 mg (500 mg 16h) |
| Primaxin (MSD) | |
| Gentamicin | 360 mg (1.5 mg/kg q8h for an 80-kg patient) |
| Garamycin (Schering) | |
| (generic) (Elkins-Sinn) | |
| Tobramycin | 360 mg (1.5 mg/kg q8h for an 80-kg patient) |
| Nebcin (Dista) | |
| Amikacin | 1200 mg (7.5 mg/kg q12h for an 80-kg patient) |
| Amikin (Bristol) | |
| Clindamycin | 2400 mg (600 mg q6h) |
| Cleocin (Upjohn) | 2700 mg (900 mg q8h) |
| | 1800 mg (600 mg q8h) |
| Chloramphenicol | 4 g (1 g q6h) |
| Chloromycetin (P/D) | |
| TMP/SMZ | 1400 mg TMP (5 mg TMP/kg q6h for a 70-kg patient) |
| Septra (Burroughs Wellcom) | |
| | 700 mg TMP (5 mg TMP/kg q12h for a 70-kg patient) |
| Erythromycin | 2000 mg (500 mg q6h) |
| Erythromycin (Elkins-Sinn) | |
| Doxycycline | 200 mg (100 mg q12h) |
| Vibramycin (Pfizer) | |
| Vancomycin | 2000 mg (500 mg q6h) |
| Vancocin (Lilly) | |
| Metronidazole | 2000 mg (500 mg q6h) |
| (generic) (Elkins-Sinn) | |
| Ciprofloxacin | 200 mg q12h |
| Cipro | 400 mg q12h |
| Pentamidine | 280 mg (4 mg/kg q24h for a 70-kg patient) |
| Pentam (LyphoMed) | |

The effectiveness of erythromycin and lincomycin against a wide variety of organisms is shown in Table 7 (taken from Lorian, 1991) to illustrate the range of antibiotic resistance acquired by various bacterial strains. The data presented in the tables of the present specification is merely illustrative and is considered another tool to enable the straightforward comparison of raw data with accepted clinical practice and to allow the determination of appropriate doses of combined agents for clinical use.

TABLE 7

SUSCEPTIBILITY TO ANTIBIOTICS

| Species | (n) | Range | $MIC_{50}$ | $MIC_{90}$ |
|---|---|---|---|---|
| ERYTHROMYCIN | 6 | | | |
| Bacillus spp. | 20 | 0.03–2 | 0.25 | 2 |
| Bacteroides fragilis | 97 | 0.25–16 | 1 | 8 |
| Bordetella bronchiseptica | 11 | 4–32 | 8 | 32 |
| Bordetella parapertussis | 46 | 0.125–4 | 0.25 | 0.25 |
| Bordetella pertussis | 32 | 1–0.5 | 0.25 | 0.25 |
| Bordetella pertussis | 75 | 0.125–0.5 | 0.125 | 0.125 |
| Borrelia burgdorferi | 10 | 0.03–0.125 | 0.03 | 0.06 |
| Branhamella (Moraxella) catarrhalis | 20 | 0.125–0.5 | 0.25 | 0.25 |
| Branhamella (Moraxella) catarrhalis | 20 | 0.125–0.5 | 0.25 | 1 |
| Branhamella (Moraxella) catarrhalis (non β-lactamase producer) | 40 | 0.06–0.5 | 0.25 | 0.5 |
| Branhamella (Moraxella) catarrhalis (non β-lactamase producer) | 13 | 0.03–0.125 | 0.06 | 0.06 |
| Branhamella (Moraxella) catarrhalis (non β-lactamase producer) | 14 | 0.06–1 | 0.125 | 1 |
| Branhamella (Moraxella) catarrhalis (non β-lactamase producer) | 16 | 0.015–1 | 0.06 | 0.25 |
| Branhamella (Moraxella) catarrhalis (β-lactamase producer) | 47 | 0.06–1 | 0.25 | 0.5 |
| Branhamella (Moraxella) catarrhalis (β-lactamase producer) | 58 | 0.03–0.25 | 0.125 | 0.125 |
| Branhamella (Moraxella) catarrhalis (β-lactamase producer) | 160 | 0.06–8 | 0.25 | 0.5 |
| Branhamella (Moraxella) catarrhalis (β-lactamase producer) | 35 | 0.03–0.125 | 0.06 | 0.06 |
| Campylobacter jejuni | 25 | 0.5–8 | 1 | 4 |
| Campylobacter jejuni | 16 | 0.125–4 | 0.25 | 2 |
| Campylobacter pylori | 56 | 0.25–16 | 0.5 | 1 |
| Campylobacter pylori | 13 | 0.125–0.25 | 0.125 | 0.25 |
| Corynebacterium JK | 102 | 0.5–$^3$128 | $^3$128 | $^3$128 |
| Corynebacterium JK | 19 | 0.125–$^3$64 | 2 | $^3$64 |
| Enterococcus faecalis | 26 | 1–$^3$64 | 1 | 4 |
| Enterococcus faecalis | 50 | 0.06–$^3$64 | 4 | $^3$64 |

TABLE 7-continued

SUSCEPTIBILITY TO ANTIBIOTICS

| Species | (n) | Range | $MIC_{50}$ | $MIC_{90}$ |
|---|---|---|---|---|
| Enterococcus faecalis | 86 | 0.125–$^3$64 | 1 | $^3$64 |
| Enterococcus faecalis | 97 | 0.125–128 | 2 | 128 |
| Enterococcus faecium | 14 | 0.06–$^3$64 | 1 | $^3$64 |
| Enterococcus spp. | 35 | 0.06–$^3$32 | 2 | $^3$32 |
| Haemophilus ducreyi | 122 | ?–0.125 | 0.004 | 0.06 |
| Haemophilus influenzae | 145 | 0.5–8 | 2 | 2 |
| Haemophilus influenzae | 97 | 0.25–$^3$16 | 1 | 4 |
| Haemophilus influenzae (non β-lactamase producer) | 22 | 0.125–8 | 2 | 4 |
| Haemophilus influenzae (non β-lactamase producer) | 137 | 0.06–$^3$8 | 4 | 8 |
| Haemophilus influenzae (β-lactamase producer) | 46 | 0.06–8 | 4 | 8 |
| Haemophilus influenzae (β-lactamase producer) | 17 | 0.25–4 | 2 | 4 |
| Haemophilus influenzae (penicillin susceptible) | 22 | 0.25–16 | 8 | 16 |
| Haemophilus influenzae (penicillin resistant) | 20 | 8–16 | 8 | 16 |
| Haemophilus parainfluenzae | 13 | 0.5–8 | 2 | 4 |
| Legionella spp. | 23 | 0.03–0.25 | 0.125 | 0.25 |
| Legionella pneumophila | 31 | 0.0075–0.25 | 0.06 | 0.125 |
| Legionella pneumophila | 48 | 0.03–2 | 0.25 | 0.5 |
| Legionella pneumophila | 25 | 0.125–1 | 0.25 | 1 |
| Listeria monocytogenes | 13 | 0.5–1 | 0.5 | 0.5 |
| Listeria monocytogenes | 16 | 0.125–2 | 0.25 | 1 |
| Listeria monocytogenes | 65 | 0.06–$^3$32 | 0.125 | 32 |
| Mycoplasma hominis | 26 | $^3$128 | $^3$128 | $^3$128 |
| Mycoplasma hominis | 20 | $^3$256 | $^3$256 | $^3$256 |
| Mycoplasma pneumoniae | 10 | 0.06–8 | 0.06 | 0.06 |
| Mycoplasma pneumoniae | 14 | 0.004–0.03 | 0.004 | 0.004 |
| Neisseria gonorrhoeae | 19 | 0.0075–8 | 0.25 | 1 |
| Neisseria gonorrhoeae (non β-lactamase producer) | 73 | 0.015–4 | 0.25 | 2 |
| Neisseria gonorrhoeae (non β-lactamase producer) | 78 | 0.03–2 | 0.25 | 1 |
| Neisseria gonorrhoeae (β-lactamase producer) | 12 | 0.03–4 | 0.5 | 2 |
| Neisseria gonorrhoeae (β-lactamase producer) | 17 | 1–4 | 2 | 4 |
| Neisseria meningitidis | 19 | 0.5–8 | 1 | 8 |
| Nocardia asteroides | 78 | 0.25–$^3$8 | $^3$8 | $^3$8 |
| Staphylococcus aureus | 44 | 0.125–1 | 0.125 | 0.5 |
| Staphylococcus aureus | 100 | 0.25–128 | 0.5 | 4 |
| Staphylococcus aureus (penicillin susceptible) | 20 | 0.125–0.5 | 0.5 | 0.5 |
| Staphylococcus aureus (penicillin susceptible) | 35 | 0.06–$^3$32 | 0.25 | 0.5 |
| Staphylococcus aureus (penicillin resistant) | 35 | 0.25–$^3$32 | 0.25 | $^3$32 |
| Staphylococcus aureus (methicillin susceptible) | 28 | 0.125–1 | 0.25 | 0.5 |
| Staphylococcus aureus (methicillin susceptible) | 97 | 0.125–$^3$64 | 0.25 | $^3$64 |
| Staphylococcus aureus (methicillin susceptible) | 20 | 0.125–1 | 0.5 | 0.5 |
| Staphylococcus aureus (methicillin resistant) | 17 | 0.5–$^3$128 | 128 | 128 |
| Staphylococcus aureus (methicillin resistant) | 15 | $^3$64 | $^3$64 | $^3$64 |
| Staphylococcus aureus (methicillin resistant) | 20 | $^3$64 | $^3$64 | $^3$64 |
| Staphylococcus aureus (methicillin resistant) | 30 | 0.06–$^3$32 | $^3$32 | $^3$32 |
| Staphylococcus coagulase f | 10 | 0.125–4 | 0.25 | 2 |
| Staphylococcus coagulase f | 100 | 0.125–$^3$64 | 0.25 | $^3$64 |
| Staphylococcus coagulase f (non β-lactamase producer) | 12 | 0.03–8 | 0.125 | 0.25 |
| Staphylococcus coagulase f (β-lactamase producer) | 38 | 0.06–16 | 0.125 | 4 |
| Staphylococcus epidermidis | 50 | 0.125–$^3$64 | $^3$64 | $^3$64 |
| Staphylococcus haemolyticus | 20 | 0.125–$^3$64 | $^3$64 | $^3$64 |
| Staphylococcus hominis | 20 | 0.125–$^3$64 | $^3$64 | $^3$64 |
| Streptococcus agalactiae | 20 | 0.03–0.25 | 0.03 | 0.125 |
| Streptococcus agalactiae | 34 | 0.015–0.06 | 0.03 | 0.03 |
| Streptococcus pneumoniae | 58 | 0.03–0.25 | 0.06 | 0.125 |
| Streptococcus pneumoniae | 91 | 0.125–4 | 0.125 | 0.125 |
| Streptococcus pneumoniae | 50 | 0.015–0.06 | 0.03 | 0.03 |
| Streptococcus pneumoniae | 16 | 0.03–0.125 | 0.06 | 0.125 |
| Streptococcus pneumoniae | 26 | 0.015–0.25 | 0.03 | 0.06 |
| Streptococcus pneumoniae | 50 | 0.03–0.125 | 0.06 | 0.06 |
| Streptococcus pyogenes | 19 | 0.03–0.25 | 0.06 | 0.125 |
| Streptococcus pyogenes | 20 | 0.03–0.25 | 0.06 | 0.125 |
| Streptococcus pyogenes | 33 | 0.015–0.03 | 0.03 | 0.03 |
| Streptococcus pyogenes | 20 | 0.06–$^3$32 | 0.125 | $^3$32 |
| Streptococcus spp. | 22 | 0.015–0.25 | 0.03 | 0.06 |
| Streptococcus spp. | 107 | 0.004–2 | 0.03 | 1 |
| Ureaplasma urealyticum | 28 | 0.015–$^3$256 | 2 | $^3$256 |
| Ureaplasma urealyticum | 19 | 8–$^3$128 | 16 | 32 |
| LINCOMYCIN | | | | |
| Mycoplasma hominis | 28 | 0.5–16 | 2 | 4 |
| Mycoplasma pneumoniae | 11 | 2–32 | 8 | 32 |
| Staphylococcus aureus | 100 | 0.5–512 | 1 | 1 |
| Ureaplasma urealyticum | 19 | 64–$^3$128 | $^3$128 | $^3$128 |

B. Pharmaceutical Compositions

The phrases "pharmaceutically" or "pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. Routes of administration may be selected from intravenous, intrarterial, intrabuccal, intraperitoneal, intramuscular, subcutaneous, oral, topical, rectal, vaginal, nasal and intraocular.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

In a particular embodiment, liposomal formulations are contemplated. Liposomal encapsulation of pharmaceutical agents prolongs their half-lives when compared to conventional drug delivery systems. Because larger quantities can be protectively packaged, this allow the opportunity for dose-intensity of agents so delivered to cells. This would be particularly attractive in the chemotherapy of cervical cancer if there were mechanisms to specifically enhance the cellular targeting of such liposomes to these cells.

"Liposome" is a generic term encompassing a variety of single and multilamellar lipid vehicles formed by the generation of enclosed lipid bilayers. Phospholipids are used for preparing the liposomes according to the present invention and can carry a net positive charge, a net negative charge or are neutral. Dicetyl phosphate can be employed to confer a negative charge on the liposomes, and stearylamine can be used to confer a positive charge on the liposomes. Liposomes are characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are cationic lipid-nucleic acid complexes, such as lipofectamine-nucleic acid complexes.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression vectors have been successfully employed in transfer and expression of a polynucleotide in vitro and in vivo, then they are applicable for the present invention. Where a bacterial promoter is employed in the DNA construct, it also will be desirable to include within the liposome an appropriate bacterial polymerase.

Lipids suitable for use according to the present invention can be obtained from commercial sources. For example, dimyristyl phosphatidylcholine ("DMPC") can be obtained from Sigma Chemical Co., dicetyl phosphate ("DCP") is obtained from K & K Laboratories (Plainview, N.Y.); cholesterol ("Chol") is obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform, chloroform/methanol or t-butanol can be stored at about −20° C. Preferably, chloroform is used as the only solvent since it is more readily evaporated than methanol.

Phospholipids from natural sources, such as egg or soybean phosphatidylcholine, brain phosphatidic acid, brain or plant phosphatidylinositol, heart cardiolipin and plant or bacterial phosphatidylethanolamine are preferably not used as the primary phosphatide, i.e., constituting 50% or more of the total phosphatide composition, because of the instability and leakiness of the resulting liposomes.

Liposomes used according to the present invention can be made by different methods. The size of the liposomes varies depending on the method of synthesis. A liposome suspended in an aqueous solution is generally in the shape of a spherical vesicle, having one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present both within and without the liposome, the lipid molecules will form a bilayer, known as a lamella, of the arrangement XY-YX.

Liposomes within the scope of the present invention can be prepared in accordance with known laboratory techniques. In one preferred embodiment, liposomes are prepared by mixing liposomal lipids, in a solvent in a container, e.g., a glass, pear-shaped flask. The container should have a volume ten-times greater than the volume of the expected suspension of liposomes. Using a rotary evaporator, the solvent is removed at approximately 40° C. under negative pressure. The solvent normally is removed within about 5 min to 2 hours, depending on the desired volume of the liposomes. The composition can be dried further in a desiccator under vacuum. The dried lipids generally are discarded after about 1 week because of a tendency to deteriorate with time.

Dried lipids can be hydrated at approximately 25–50 mM phospholipid in sterile, pyrogen-free water by shaking until all the lipid film is resuspended. The aqueous liposomes can be then separated into aliquots, each placed in a vial, lyophilized and sealed under vacuum.

In the alternative, liposomes can be prepared in accordance with other known laboratory procedures: the method of Bangham et al. (1965), the contents of which are incorporated herein by reference; the method of Gregoriadis (1979), the contents of which are incorporated herein by reference; the method of Deamer and Uster (1983), the contents of which are incorporated by reference; and the reverse-phase evaporation method as described by Szoka and Papahadjopoulos (1978). The aforementioned methods differ in their respective abilities to entrap aqueous material and their respective aqueous space-to-lipid ratios.

The dried lipids or lyophilized liposomes prepared as described above may be reconstituted in a solution of nucleic acid and diluted to an appropriate concentration with an suitable solvent, e.g., DPBS. The mixture is then vigorously shaken in a vortex mixer. Unencapsulated nucleic acid is removed by centrifugation at 29,000×g and the liposomal pellets washed. The washed liposomes are resuspended at an appropriate total phospholipid concentration, e.g., about 50–200 mM. The amount of nucleic acid encapsulated can be determined in accordance with standard methods. After determination of the amount of nucleic acid encapsulated in the liposome preparation, the liposomes may be diluted to appropriate concentration and stored at 4° C. until use.

In a preferred embodiment, the lipid dioleoylphosphatidylchoine is employed. Nuclease-resistant oligonucleotides were mixed with lipids in the presence of excess t-butanol. The mixture was vortexed before being frozen in an acetone/dry ice bath. The frozen mixture was lyophilized and hydrated with Hepes-buffered saline (1 mM Hepes, 10 mM NaCl, pH 7.5) overnight, and then the liposomes were sonicated in a bath type sonicator for 10 to 15 min. The size of the liposomal-oligonucleotides typically ranged between 200–300 nm in diameter as determined by the submicron particle sizer autodilute model 370 (Nicomp, Santa Barbara, Calif.).

The purified antimicrobial peptide may be used without further modifications or it may be diluted in a pharmaceutically acceptable carrier. The peptides may be used independently or in combination with other antimicrobial agents. Because of the stability of the peptides it is contemplated that the invention may be administered to humans or animals, included in food preparations, pharmaceutical preparations, medicinal and pharmaceutical products, cosmetic products, hygienic products, cleaning products and cleaning agents, as well as any material to which the peptides could be sprayed on or adhered to wherein the inhibition of microbial growth is desired.

3. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Peptide Synthesis

All peptides were synthesized by the solid-phase method employing an Applied Biosystems model 433A peptide synthesizer and Fastmoc strategy at the 0.1 mM scale. Peptides were purified by reversed-phase HPLC on a Waters Delta Prep employing a Vydac 218TP1022 (22×250 mm) column. Separation was performed with a gradient system of aqueous 0.1% trifluoroacetic acid (solvent A) and 100% acetonitrile containing 0.085% trifluoroacetic acid (solvent B). A linear gradient from 0 to 100% B was applied over 70 min and fractions collected every 0.2 min. Fractions were subsequently monitored by analytical scale reversed-phase HPLC on a Beckman Gold System using a Vydac 218TP54 (4.6×250 mm) column at a flow rate of 0.5 ml/min under isocratic elution conditions. Select fractions were pooled and lyophilized; further characterization of peptides was provided by mass spectrometry and capillary electrophoresis. Mass measurements were performed by flow injection at 0.1 ml/min in 64% acetonitrile containing 0.05% trifluoroacetic acid with a Hewlett-Packard model 1100 MSD equipped with an electrospray ionization source. Capillary electrophoresis was performed on a Hewlett-Packard 3D instrument equipped with an extended light path fused-silica column 75 micrometers (ID)×80.5 centimeters (total length). Capillary electrophoresis experiments were conducted at 18 C in 100 mM sodium phosphate buffer, pH 2.9 at 20,000 volts. Peptide concentration was determined by quantitative amino acid analysis on a Beckman 6300 Amino Acid analyzer.

Example 2

Bacterial Strains and Antimicrobial Assays

We adapted a luminescence assay that we had previously used with *E. coli* (Singh, 1999 and Travis, 1999) to examine the time-course of killing and the potency of the peptides against *P. aeruginosa* PAO1 in high and low salt buffer solutions. This assay measured antimicrobial activity as a decrease in energy-dependent luminescence of bacteria containing luminescence genes. *P. aeruginosa* strain PAO1 was transformed with the *Vibrio fischeri* luminescence genes on the pBBRIMCS-5 plasmid (Frackman, 1999). *P. aeruginosa* was grown to early log phase (2.5×10$^7$ bacteria/ml) at 30° C. in tryptic soy broth containing 25 µg/ml gentamicin, then used without centrifugation. For each assay, 5×10$^5$ bacteria were incubated in 6.7 mM potassium phosphate, pH 7.4, 3.3% tryptic soy broth, antimicrobial peptide and other additions in a total volume of 150 µl in 96-well plates (Optiplate, Packard Instruments). After incubation at 30° C. for the indicated time, relative emission of light (in arbitrary units) was measured with a Packard Instruments luminometer (Meriden, Conn.). We defined the EC$_{50}$ as the amount of antimicrobial peptide that decreased luminescence by 50%. The ionic strength of the standard low salt assay solution was calculated to be 25 mM. In some experiments the ionic strength was increased to 175 mM by the addition of 150 mM NaCl. For colony counting assays, bacteria were prepared and incubated with antimicrobial peptides as described above, then plated on nutrient agar plates. Colonies were counted after incubation of the plates for 24–48 hr at 37° C.

Minimal inhibitory concentrations (MICs) for Gram-positive and Gram-negative clinical isolates were determined by a Microbroth tray dilution assay. Serial two-fold dilutions of peptides (0.06–32 ug/ml) in Mueller-Hinton broth ([Na+]=128 mM, [Cl−]=108 mM) were inoculated with 100,000 CFU of bacteria, incubated at 35° C. and read at 24 hr.

The two stage radial diffusion assay used in these studies has been described elsewhere (Lehrer et al., 1991). Briefly, the purified peptides were serially diluted in acidified water (0.01% acetic acid) that contained 0.1% human serum albumin (Sigma A-8763). The bacteria (*E. coli* ML-35P, *P. aeruginosa* MR 3007, *S. aureus* 930918-3, and methicillin-resistant *S. aureus* ATCC 33591 (MRSA) were grown to mid-logarithmic phase in trypticase soy broth and washed with 10 mM phosphate buffer, pH 7.4. Approximately 2×10$^5$ CFU/ml was incorporated into a thin (1.23 mm) agarose underlay gel that contained 1% w/v agarose (Sigma A-6013), 10 mM sodium phosphate buffer, pH 7.4, and 0.3 mg/ml trypticase soy broth powder±100 mM NaCl. A regularly spaced, 5-by-5 array of wells was made in the underlay gel. The wells, 3.2 mm in diameter, had a 10 µl capacity. Six serially diluted samples of each peptide were prepared, ranging in concentration from 0.79 to 250 µg/ml, and 5 µl aliquots were added to the wells. After 3 hours, a 10 ml overlay gel composed of 6% trypticase soy broth powder, 1% agarose and 10 mM sodium phosphate buffer, pH 7.4 was poured, and the plates were incubated overnight to allow surviving organisms to form microcolonies.

The zone diameters were measured to the nearest 0.1 mm and were expressed in units (1 unit=0.1 mm), after first subtracting the diameter of the well. A linear relationship existed between the zone diameter and the log$_{10}$ of the peptide concentration. The minimal inhibitory concentration was determined by performing a least mean squares fit and solving for the X-intercept with a Hewlett Packard 20S Scientific Calculator or its equivalent.

Example 3

CD Spectroscopy

Circular dichroism (CD) spectroscopy was performed on an AVIV 62 DS spectrometer (AVIV Associates, Lakewood, N.J.) equipped with a thermoelectric temperature control at 25 C. Samples contained 0.11–0.24 mg/mL peptide in either 50 mM sodium phosphate, pH 7.0; some samples also contained 40% trifluoroethanol or 0.1% (0.22 mM) lipopolysaccharide (LPS). LPS from a clinical isolate of *Neisseria meningitidis* Type B was provided by Dr. M. A. Apicella. Spectra were collected at 0.5 nm intervals with an averaging time of 2 s per datum point using a pathlength of 0.1 cm. The spectra were smoothed once over an interval of five data points prior to plotting with each spectrum representing the average of two scans. The average of two buffer scans was subtracted prior to data smoothing. The fractional helical content was calculated from the ratio of observed mean residue ellipticity to the mean residue ellipticity for a 100% helical peptide of identical length at 25° C. according to Luo and Baldwin (1997).

Example 4

Calculation of Peptide Hydrophobic Moment and Hydrophobicity

Peptide hydrophobicities and hydrophobic moments were calculated as described by Eisenberg (1986) using normalized consensus hydrophobicity scales.

Example 5

Hemolysis Assay

Hemolytic activity of the peptides was assayed with heparinized human red blood cells. The cells were collected from a normal volunteer and washed three times in Dulbecco's PBS (PBS, Sigma). A 10% suspension of red blood cells was combined with peptide in a final volume of 200 µl in PBS. PBS was used as a negative control; 0.2% Triton X-100 was used as a positive control. After 30 min incubation, the mixture was centrifuged 10 min at 3000 rpm in a Beckman TJ6 benchtop centrifuge. Supernatant was carefully transferred to a flat bottom polystyrene 96 well microtiter plate and read at 540 nm. Percent hemolysis was calculated using the formula: $(A_{Sample}-A_{blank})/(A_{Triton}-A_{blank}) \times 100$.

Example 6

Ovine In Vivo Pulmonary Infection Model

Fifteen lambs were randomized to four groups and were lightly sedated with 10 mg xylazine. A small plastic tube was inserted into the oral cavity and served as a speculum. A bronchoscope was inserted into the tube and lidocaine (0.5 ml of 2% lidocaine hydrochloride) was administered at the larynx. The tip of the bronchoscope was placed into the dorsum of the caudal portion of the right cranial lobe (pulmonary deposition site) in each animal for deposition of bacterial suspension and treatment inocula). After inoculation, the effects of xylazine were reversed by intravenous injection of 100 mg tolazoline HCl. Lambs in Group I (2 lambs) and Group II (3 lambs) received 10 ml PBS/PS. Lambs in Group III (5 lambs) and Group IV (5 lambs) received 10 ml PBS/PS and $2.5 \times 10^8$ CFU/ml P. haemolytica in PBS/PS, respectively.

At 24 hr post inoculation (PI), lambs in Group I and Group III received an additional 10 ml PBS/PS at the same deposition site. Lambs in Group II received 10 ml PBS/PS with 100 ug SMAP/ml and Group IV received 10 ml PBS/PS with 50 ug SMAP29/ml. At 48 h PI, all lambs were euthanized with pentobarbital and exsanguinated. At necropsy, the lungs were evaluated grossly and total lung involvement was calculated as the sum of the consolidated portions of each lobe multiplied by the percent each lobe contributes to the total lung volume as previously described (Brogden, 199). The pulmonary inoculation and treatment site was lavaged with 20 ml of PBS. The bronchoalveolar lavage fluids (BALF) were collected for quantitative culture and determination of total cell count. Tissue was then taken for quantitative bacteriological culture and isolated bacterial species were identified by conventional methodology. All P. haemolytica isolates were serotyped to confirm their identity as the original organism.

Pieces of tissue were also taken from the pulmonary deposition site and fixed in 10% neutral buffered formalin solution, dehydrated and cleared, embedded in paraffin, sectioned, and stained with Giemsa and hematoxylin and eosin stains. Lung sections were scored histopathologically in terms of cellular infiltration (lymphocytic and/or neutrophilic), necrosis and collapse as previously described (Brogden, 199). The maximum score was 4 for each category.

Example 7

Statistics

Statistical differences among gross pulmonary lesions, histopathological lesions, pulmonary cells and P. haemolytica in BAL fluids, and P. haemolytica in consolidated pulmonary tissue were determined with the Sigmastat 2.03 and Sigmaplot 4.01 (SPSS Inc., Chicago, Ill.).

Example 8

Results

The following tables summarize the results of experiments described in the preceding section, as do the attached figures and related figure descriptions. These tables exemplify the efficacy of the disclosed peptides and reflect specific peptides which applicants feel have maximum effectiveness.

TABLE 8A

INHIBITION OF P. AERUGINOSA PAO1 AND E. COLI DH5α BY CAP18 PEPTIDES[1]

| Peptide | Sequence | Ionic Strength (mM) | $EC_{50}$ P. aeruginosa PAO1 | | | $EC_{50}$ E. coli DH5α | | |
|---|---|---|---|---|---|---|---|---|
| | | | µg/ml ± sem | µM ± sem | N | µg/ml ± sem | µM ± sem | N |
| CAP 18 | GLRKRLRKFRNKIKEKLKKIG QKIQGLLPKLAPRTDY (SEQ ID NO:18) | 25<br>175 | 0.98 ± 0.24<br>0.50 ± 0.10 | 0.22 ± 0.05<br>0.11 ± 0.02 | (6)<br>(4) | 0.69 ± 0.08 | 0.15 ± 0.02 | (4) |
| CAP18-21a | GLRKRLRKFRNKIKEKLKKIG (SEQ ID NO:19) | 25<br>175 | 0.58 ± 0.09<br>0.54 ± 0.10 | 0.22 ± 0.03<br>0.21 ± 0.04 | (3)<br>(3) | 0.48 ± 0.03 | 0.19 ± 0.01 | (3) |
| CAP18-18 | KRLRKFRNKIKEKLKKIG (SEQ ID NO:20) | 25<br>175 | 1.05 ± 0.37<br>1.59 ± 0.29 | 0.46 ± 0.16<br>0.69 ± 0.13 | (3)<br>(3) | 0.47 ± 0.06 | 0.20 ± 0.03 | (3) |
| CAP18-22 | RKRLRKFRNKIKEKLKKIGQKI (SEQ ID NO:21) | 25<br>175 | 1.38 ± 0.49<br>0.88 ± 0.12 | 0.49 ± 0.17<br>0.31 ± 0.04 | (4)<br>(4) | 1.47 ± 0.44 | 0.52 ± 0.16 | (3) |
| CAP18-19 | LRKFRNKIKEKLKKIGQKI (SEQ ID NO:22) | 25<br>175 | 1.65 ± 0.27<br>3.06 ± 0.36 | 0.70 ± 0.11<br>1.29 ± 0.15 | (3)<br>(3) | 2.27 ± 0.30 | 0.96 ± 0.13 | (4) |
| CAP18-21b | LRKFRNKIKEKLKKIGQKIQG (SEQ ID NO:23) | 25<br>175 | 1.83 ± 0.51<br>3.45 ± 0.02 | 0.72 ± 0.20<br>1.35 ± 0.01 | (4)<br>(2) | 2.99 ± 0.33 | 1.17 ± 0.13 | (3) |
| CAP18-15a | RKFRNKIKEKLKKIG (SEQ ID NO:24) | 25<br>175 | 1.54 ± 0.43<br>>20 | 0.81 ± 0.23<br>>10 | (3)<br>(3) | 0.46 ± 0.12 | 0.24 ± 0.07 | (3) |
| CAP18-15b | KIKEKLKKIGQKIQG (SEQ ID NO:25) | 25<br>175 | 10.3 ± 0.3<br>>80 | 5.92 ± 0.20<br>>45 | (3)<br>(3) | 7.23 ± 1.81 | 4.15 ± 1.04 | (4) |
| CAP18-17 | KIKEKLKKIGQKIQGLL (SEQ ID NO:26) | 25<br>175 | 2.33 ± 0.35<br>>25 | 1.18 ± 0.18<br>>13 | (4)<br>(3) | 2.51 ± 0.38 | 1.27 ± 0.20 | (4) |

[1]$EC_{50}$s were measured in the luminescence assay, performed at 25 mM and 175 mM ionic strength with PAO1 and 25 mM with DH5α. Data are average ± Sem.

[1] $EC_{50}$s were measured in the luminescence assay, performed at 25 mM and 175 mM ionic strength with PAO1 and 25 mM with DH5α. Data are average±Sem.

TABLE 8B

INHIBITION OF *P. AERUGINOSA* PAO1 BY SMAP29 PEPTIDES[2]

| Peptide | Sequence | Ionic Strength (mM) | $EC_{50}$ *P. aeruginosa* PAO1 µg/ml ± sem | µM ± sem | N |
|---|---|---|---|---|---|
| SMAP29 | RGLRRLGRKIAHGVKKYGPT VLRIIRIAG (SEQIDNO:2) | 25 | 0.17 ± 0.02 | 0.05 ± 0.01 | (8) |
|  |  | 175 | 0.21 ± 0.03 | 0.06 ± 0.01 | (7) |
| SMAP29-18 | RGLRRLGRKIAHGVKKYG (SEQIDNO:5) | 25 | 0.43 ± 0.08 | 0.21 ± 0.04 | (7) |
|  |  | 175 | 0.76 ± 0.09 | 0.37 ± 0.05 | (7) |
| SMAP29-21 | KIAHGVKKYGPTVLRIIRIAG (SEQIDNO:3) | 25 | 1.09 ± 0.16 | 0.48 ± 0.07 | (5) |
|  |  | 175 | 16.6 ± 1.41 | 7.25 ± 0.62 | (3) |
| SMAP29-20 | LGRKIAHGVKKYGPTVLRII (SEQIDNO:4) | 25 | 0.83 ± 0.10 | 0.37 ± 0.05 | (5) |
|  |  | 175 | 27.3 ± 3.97 | 12.3 ± 1.79 | (5) |
| SMAP29-18AA | RGLRALGRKIAHGVKAYG (SEQIDNO:29) | 25 | 0.62 ± 0.13 | 0.32 ± 0.07 | (3) |
|  |  | 175 | 7.85 ± 1.16 | 4.08 ± 0.87 | (3) |
| SMAP29X | KNLRRIIRKIIHIIKKYGPTILR IIRIIG-NH2 (SEQIDNO:28) | 25 | 2.74 ± 0.65 | 0.78 ± 0.19 | (4) |
|  |  | 175 | 4.51 ± 0.24 | 1.29 ± 0.07 | (3) |
| SMAP29X-18A | KNLRRIIRKIIHIIKKYG-NH2 (SEQIDNO:1) | 25 | 0.22 ± 0.00 | 0.10 ± 0.00 | (3) |
|  |  | 175 | 0.49 ± 0.02 | 0.22 ± 0.01 | (3) |
| SMAP29X-18B | KNIRRIIRKIIHIIKKYG-NH2 (SEQIDNO:6) | 25 | 0.16 ± 0.01 | 0.07 ± 0.00 | (3) |
|  |  | 175 | 0.54 ± 0.05 | 0.24 ± 0.02 | (3) |
| SMAP29X-18C | KNIRRIIRKIIHIIKKYG (SEQ IDNO:7) | 25 | 0.24 ± 0.01 | 0.11 ± 0.00 | (3) |
|  |  | 175 | 0.61 ± 0.12 | 0.27 ± 0.05 | (3) |
| SMAP29X-18D | KNLRRIIRKIIHIIKKYG (SEQ IDNO:8) | 25 | 0.29 ± 0.01 | 0.13 ± 0.01 | (3) |
|  |  | 175 | 0.58 ± 0.05 | 0.26 ± 0.02 | (3) |
| SMAP29X-16A | NLRRIIRKIIHIIKKY (SEQID NO:9) | 25 | 0.90 ± 0.54 | 0.43 ± 0.26 | (3) |
|  |  | 175 | 1.78 ± 0.26 | 0.86 ± 0.12 | (3) |
| SMAP29X-16B | NLRRIIRKIIHIIKKY-NH2 (SEQIDNO:30) | 25 | 0.75 | 0.36 | (1) |
|  |  | 175 | 3.78 | 1.82 | (1) |
| SMAP29X-16C | NIIRRIIRKIIHIIKKY-NH2 (SEQIDNO:31) | 25 | 0.65 | 0.31 | (1) |
|  |  | 175 | 2.21 | 1.07 | (1) |
| SMAP29X-16D | NIRRIIRKIIHIIKKY (SEQID NO:10) | 25 | 0.70 ± 0.36 | 0.34 ± 0.17 | (3) |
|  |  | 175 | 3.64 ± 1.75 | 1.75 ± 0.84 | (3) |
| SMAP29X-14A | LRRIIRKIIHIIKK-NH2 (SEQ IDNO:11) | 25 | 0.23 ± 0.03 | 0.13 ± 0.02 | (3) |
|  |  | 175 | 1.59 ± 0.22 | 0.88 ± 0.12 | (3) |
| SMAP29X-14B | LRRIIRKIIHIIKK (SEQID NO:12) | 25 | 0.55 ± 0.03 | 0.30 ± 0.02 | (3) |
|  |  | 175 | 5.55 ± 0.42 | 3.08 ± 0.23 | (3) |
| SMAP29X-14C | IRRIIRKIIHIIKK-NH2 (SEQID NO:13) | 25 | 0.29 ± 0.04 | 0.16 ± 0.02 | (3) |
|  |  | 175 | 1.21 ± 0.05 | 0.67 ± 0.03 | (3) |
| SMAP29X-14D | IRRIIRKIIHIKK (SEQID NO:14) | 25 | 0.65 ± 0.06 | 0.36 ± 0.03 | (3) |
|  |  | 175 | 7.11 ± 2.40 | 3.95 ± 1.34 | (3) |

[2]$EC_{50}$s were measured in the luminescence assay, performed at 25 mM and 175 mM ionic strength. Data are average ± sem.

[2] $EC_{50}$s were measured in the luminescence assay, performed at 25 mM and 175 mM ionic strength. Data are average±sem.

| Peptide | Sequence | Ionic Strength (mM) | $EC_{50}$ *P. aeruginosa* PAO1 µg/ml ± sem | µM ± sem | N |
|---|---|---|---|---|---|
| SMAP29X-13A | LRRIIRKIIHIIK-NH2 (SEQID NO:15) | 25 | 0.27 ± 0.03 | 0.16 ± 0.02 | (3) |
|  |  | 175 | 2.23 ± 0.41 | 1.34 ± 0.25 | (3) |
| SMAP29X-13B | RRIIRKIIHIIKK-NH2 (SEQID NO:16) | 25 | 0.22 ± 0.02 | 0.13 ± 0.01 | (3) |
|  |  | 175 | 1.51 ± 0.09 | 0.90 ± 0.06 | (3) |
| SMAP29X-12 | RRIIRKIIHIIK-NH2 (SEQID NO:17) | 25 | 0.31 ± 0.01 | 0.20 ± 0.01 | (3) |
|  |  | 175 | 3.83 ± 0.22 | 2.46 ± 0.14 | (3) |
| SMAP29X-11A | RRIIRKIIHII-NH2 (SEQID NO:32) | 25 | 0.38 ± 0.04 | 0.27 ± 0.03 | (3) |
|  |  | 175 | 4.92 ± 0.43 | 3.44 ± 0.30 | (3) |
| SMAP29X-11B | RIIRKIIHIIK-NH2 (SEQID NO:33) | 25 | 0.46 ± 0.02 | 0.33 ± 0.01 | (3) |
|  |  | 175 | 10.42 ± 0.26 | 7.43 ± 0.19 | (3) |
| SMAP29X-10 | RIIRKIIHII-NH2 (SEQID NO:34) | 25 | 0.51 ± 0.00 | 0.40 ± 0.00 | (3) |
|  |  | 175 | 18.67 ± 0.97 | 14.66 ± 0.77 | (3) |

TABLE 9

Relative Time for Killing of *P. aeruginosa* PAO1 by CAP18 and SMAP29 Peptides[1]

| Peptide | Peptide (µg/ml) | Half-time of Killing (min. avg. ± sem) |
|---|---|---|
| CAP18 | 10 | 4.0 + 1.4 |
| CAP18-21A | 6 | 9.2 ± 3.4 |
| CAP18-18 | 10 | 19.5 ± 8.2 |
| CAP18-22 | 14 | 9.8 ± 2.5 |
| CAP18-19 | 16 | 8.0 ± 1.6 |
| SMAP29 | 2 | 2.3 ± 0.8 |
| SMAP29X-18D | 5[a] | 2.9 |
| SMAP29X-14A | 4[b] | 20.9 |

[1]Peptides were used at a concentration of ten times their $EC_{50}$, except where noted, with *P. aeruginosa* at 25 mM ionic strength (Tables 8A and 8B). Bacteria were incubated with peptide, and luminescence was measured at intervals. The half-time of killing is that time at which luminescence was decreased to half its original value.
[a]The concentration of SMAP29X-18D was 15.7 X the EC50.
[b]The concentration of SMAP29X-14A was 17.4 X the EC50.

[1] Peptides were used at a concentration of ten times their $EC_{50}$, except where noted, with *P. aeruginosa* at 25 mM ionic strength (Tables 8A and 8B). Bacteria were incubated with peptide, and luminescence was measured at intervals. The half-time of killing is that time at which luminescence was decreased to half its original value. [a]The concentration of SMAP29X-18D was 15.7× the EC50. [b]The concentration of SMAP29X-14A was 17.4× the EC50.

TABLE 10A

MULTIPLY DRUG-RESISTANT STRAINS OF *P. AERUGINOSA* FROM CF PATIENTS ARE INHIBITED BY CAP18 PEPTIDES[3]
(MIC, µg/ml)

| Strain # | ID | CAP18 | CAP18-22 | CAP18-18 |
|---|---|---|---|---|
| 85BM | P.a | 2 | 4 | 16 |
| 45BN | P.a | 1 | 1 | 2 |
| 83BN | P.a | 1 | 4 | 16 |
| 50BK | P.a | 4 | 2 | 8 |
| 18BA | P.a | 4 | 2 | 2 |
| 75BN | P.a | 8 | 32 | >32 |
| 13BK | MP.a | 4 | 2 | 16 |
| 7BN | MP.a | 2 | 4 | 16 |
| 1BH | MP.a | 1 | 4 | 8 |
| 26BL | MP.a | 8 | 16 | >32 |
| 38BJ | MP.a | 1 | 0.5 | 1 |
| 68BM | MP.a | 4 | 8 | 32 |

P.a: Nonmucoid
MP.a: Mucoid
These data were provided by Dr. Lisa Saiman, Dept. of Pediatrics, Columbia University, New York, NY.
[3]Determined by Microbroth Dilution Assay.

[3] Determined by Microbroth Dilution Assay.

TABLE 10B

MULTIPLY DRUG-RESISTANT STRAINS OF *P. AERUGINOSA* FROM CF PATIENTS ARE INHIBITED BY SMAP29 PEPTIDES[4]
(MIC, µg/ml)

| Strain# | ID | SMAP29 | SMAP29-18 | SMAP29X-14A | SMAP29X-14B/D | SMAP29X-18A | SMAP29X-18C | SMAP29X-18D |
|---|---|---|---|---|---|---|---|---|
| 18BA | P.a | 1 | 8 | 2 | >32 | 8 | 4 | 8 |
| 73BI | P.a | 2 | >32 | 2 | >32 | 8 | 16 | 8 |
| 3BJ | P.a | 0.5 | 4 | 2 | >32 | 4 | 8 | 4 |
| 23BJ | P.a | 8 | 8 | 16 | >32 | >32 | 32 | 16 |
| 38BK | P.a | 1 | 32 | 2 | >32 | 8 | 8 | 8 |
| 50BK | P.a | 2 | 8 | 2 | >32 | 4 | 4 | 4 |
| 1BL | P.a | 2 | >32 | 16 | >32 | 16 | 16 | 16 |
| 26BL | MP.a | 2 | >32 | 4 | >32 | 16 | 16 | 8 |
| 41BL | MP.a | 0.5 | 16 | 2 | >32 | 2 | 4 | 4 |
| 84BL | MP.a | 1 | >32 | 4 | >32 | 4 | 4 | 8 |
| 68BM | MP.a | 2 | 32 | 1 | >32 | 8 | 8 | 8 |
| 82BM | MP.a | 1 | 32 | 0.06 | >32 | 4 | 4 | 4 |
| 1BH | MP.a | 0.5 | 4 | 2 | >32 | 2 | 2 | 2 |
| 13BH | MP.a | 0.13 | 1 | 0.5 | >32 | 0.5 | 0.06 | 0.12 |
| 32BH | MP.a | 1 | 32 | 2 | >32 | 4 | 4 | 4 |
| 38BJ | MP.a | 0.5 | 32 | 4 | >32 | >32 | 2 | 16 |
| 95BJ | MP.a | 0.5 | 16 | 1 | >32 | 2 | 1 | 2 |
| 13BK | MP.a | 1 | 16 | 2 | >32 | 4 | 8 | 4 |
| 57BK | MP.a | 0.5 | 32 | 4 | >32 | 4 | 4 | 4 |

P.a: Nonmucoid
MP.a: Mucoid
These data were provided by Dr. Lisa Saiman, Dept. of Pediatrics, Columbia University, New York, NY.
[4]Determined by Microbroth Dilution Assay.

[4] Determined by Microbroth Dilution Assay.

[5] Determined by Microbroth Dilution Assay.

TABLE 11

INHIBITION OF OTHER MULTIPLY DRUG-RESISTANT BACTERIA FROM CF PATIENTS BY SMAP29 AND CAP18 PEPTIDES[5]
(MIC, µg/ml)

| Strain # | API-ID | SMAP29 | CAP18 |
|---|---|---|---|
| 29AX | A.x | 1 | 2 |
| 34AX | A.x | 32 | >32 |
| 39DB | A.x | 32 | >32 |
| 61AW | A.x | 32 | 32 |
| 62AZ | A.x | 32 | 16 |
| 33BI | B.c | >32 | >32 |
| 45BI | B.c | >32 | >32 |
| 54BK | B.c | >32 | >32 |
| 90BD | B.c | >32 | >32 |
| 96BD | B.c | >32 | >32 |
| 59BH | X.m | 2 | 4 |
| 77BJ | X.m | 4 | 16 |
| 81BG | X.m | 4 | 16 |
| 85BG | X.m | 8 | 16 |
| 100BC | X.m | 1 | 2 |

A.x: *Alcaligenes xylosoxidans*
B.c: *Burkholderia cepacia*
X.m: *Stenotrophomonas maltophilia*
These data were provided by Dr. Lisa Saiman, Dept. of Pediatrics, Columbia University, New York, NY.
[5]Determined by Microbroth Dilution Assay.

TABLE 12

VANCOMYCIN AND METHICILLIN-RESISTANT GRAM-POSITIVES ARE INHIBITED BY SMAP29 PEPTIDES[6]
(MIC, µG/ML)

| Organism | Phenotype/Genotype | Smap29 | Smap29X-18D | Smap29X-14A |
|---|---|---|---|---|
| E.f 142-1498-1 | Van A | 16 | 32 | >64 |
| E.f 142-6873-3 | Van B | 32 | 64 | >64 |
| E.fm 110-2733-2 | Van B | 4 | 16 | 16 |
| E.fm 110-6802-2 | Van A | 4 | 8 | 8 |
| E.fm 115-7485-1 | Susc. | 4 | 16 | 16 |
| S.e Dade 352 | MecA+ | 8 | 8 | 8 |
| S.e Dade 354 | MecA+ | 4 | 4 | 4 |
| S.e Dade 370 | MecA− | 4 | 4 | 8 |
| S.e Dade 371 | MecA− | 4 | 4 | 8 |
| S.a ATCC 25932 | MecA− | 8 | 16 | 64 |
| S.a ATCC 29213 | MecA− | 8 | 16 | 32 |
| S.a Dade 377 | MecA+ | 8 | 16 | 64 |
| S.a Dade 382 | MecA+ | 8 | 16 | 32 |
| S.a Mu 3 | Visa | 16 | 32 | 64 |
| S.a Mu 50 | Visa | 16 | 32 | 32 |

E.f: *Enterococcus fecaelis*
E.fm: *Enterococcus faecium*
S.a: *Staphylococcus aureus S. aureus*
S.e: *Staphylococcus epidermidis*
Mec A+: Methicillin-resistant
Mec A−: Methicillin-sensitive
Visa: Vancomycin intermediately-resistant
Van A,B: Vancomycin-resistant
These data were provided by Dr. Patrica Winokur, Dept. of Internal Medicine, U of I, Iowa City, IA.
[6]Determined by Microbroth Dilution Assay.

TABLE 13

ANTIPSEUDOMONAL AND ANTISTAPHYLOCOCCAL ACTIVITIES OF CAP18 AND SMAP29 PEPTIDES ASSESSED BY A RADIAL DIFFUSION ASSAY (MIC, µg/ml)

| | E. coli [NaCl] | | P. aeruginosa [NaCl] | | MRSA [NaCl] | | S. aureus [NaCl] | |
|---|---|---|---|---|---|---|---|---|
| | Low | High | Low | High | Low | High | Low | High |
| SMAP29 and Related Peptides | | | | | | | | |
| SMAP29 | 0.6 | 0.4 | 1.1 | 0.6 | 7.1 | 3.3 | 1.0 | 1.4 |
| SMAP29-18 | 1.9 | 0.4 | 1.0 | 9.9 | 8.7 | >250 | 2.4 | 24.5 |
| SMAP29X | 1.5 | 0.8 | 2.6 | 1.0 | 6.2 | 1.0 | 1.6 | 1.5 |
| SMAP29X-18D | 0.8 | 0.5 | 1.1 | 0.5 | 8.7 | 0.8 | 2.0 | 1.4 |
| SMAP29X-14A | 2.9 | 0.9 | 2.0 | 2.7 | 7.6 | >79.1 | 1.1 | 1.9 |
| CAP18 and Related Peptides | | | | | | | | |
| CAP18 | 0.2 | 0.4 | 0.2 | 1.6 | 8.2 | 6.1 | 1.8 | 2.8 |
| CAP18-22 | 0.1 | 1.7 | 0.7 | 7.6 | 8.1 | >79.1 | 7.9 | >79.1 |
| CAP18-21a | 2.3 | 0.4 | 0.7 | 0.9 | 19.4 | >250 | 1.8 | 2.2 |
| CAP18-18 | 2.8 | 1.5 | 2.1 | 3.2 | 14.9 | >250 | 9.7 | 29.0 |
| CAP18-15a | 0.2 | 0.7 | 1.5 | 5.3 | >250 | >250 | 19.5 | >250 |
| CAP18-21b | 2.3 | 0.5 | 2.9 | 23.5 | 10.3 | >250 | 16.3 | >250 |
| CAP18-19 | 0.4 | 18.2 | 1.0 | 26.7 | 4.5 | >79.1 | 6.0 | >79.1 |
| CAP18-17 | 9.7 | 1.9 | 5.1 | >250 | >250 | >250 | >250 | >250 |
| CAP18-15b | 1.6 | >250 | 8.7 | >250 | >250 | >250 | >250 | >250 |

Assays were performed in low salt (10 mM sodium phosphate buffer, pH 7.4) and high salt underlays (10 mM sodium phosphate buffer, +100 mM NaCl, pH 7.4). The bacterial strains were *E. coli* ML-35p, *P. aeruginosa* MR 3007, *S. aureus* 930918-3 and MRSA, ATCC 33591. These data were provided by Dr. Robert I. Lehrer, Dept. of Medicine, UCLA, Los Angeles, Calif.

TABLE 14

CONCENTRATION OF *PASTEURELLA HAEMOLYTICA*[1] IN BRONCHOAVEOLAR LAVAGE FLUID (BALF) AND CONSOLIDATED LUNG TISSUE (CLT) OF INFECTED SHEEP

| Group | $Log_{10}$ CFU/ml of BALF | $Log_{10}$ CFU/gm ofclt |
|---|---|---|
| 1 Control: PBS/PS[4] | 0 | PBS/PND |
| 2 Control: PBS/PS/SMAP29 | 0 | ND |
| 3 *P haemolytica* | $2.9 \pm 0.7^2$ | $5.1 \pm 1.0^2$ |
| 4 *P. haemolytica* + SMAP29 | $1.6 \pm 0.4^3$ | $3.7 \pm 0.9^3$ |

[1]Serotype A1, strain 82-25
[2]Mean CFU in 4 of 5 lambs
[3]Mean CFU in 3 of 5 lambs
[4]Phosphate Buffered Saline pH 7.4/Ovine Pulmonary Surfactant
These date were provided by Dr. Kim Brogden, NADC, ARS, USDA, Ames, IA.

1 Serotype A1, strain 82-25
2 Mean CFU in 4 of 5 lambs
3 Mean CFU in 3 of 5 lambs
4 Phosphate Buffered Saline pH 7.4/Ovine Pulmonary Surfactant These data were provided by Dr. Kim Brogden, NADC, ARS, USDA, Ames, Iowa.

Example 9

Susceptibility of a variety of bacterial starains to the disclosed peptides under either normal, high and low salinity were evaluated. Bacterial strains *E. coli* ML-35P, *P. aeruginosa* MR 3007, *S. aureus* 930918-3 and MRSA ATCC 33591 MICs were determined over a broader range of salt concentration, i.e. 0 to 175 mM. The susceptibility of several additional strains of bacteria were also evaluated by the Radial Immunodiffusion Assay including *E. coli* ATCC 33780 (Serotype 0111), *E. coli* DH-5alpha, *P. aeruginosa* PAO1, *N. gonorrhoeae*, *B. cepacia* ATCC 25416 and *L. monocytogenes* EGD. Results of these assays are setforth in Tables 15–24.

Example 10

The Smap28 peptide (SEQ ID NO:27), has been is the the physiologically relevant form of the sheep myeloid antimicrobial protein Smap29. The peptide was purified from sheep leukocytes, and its structure determined by mass spectrometry analysis and Edman degradation. The structure of the Smap28 peptide is represented by two interconvertable conformers of the "helix-hinge-helix" motif. It is believed that the the N- and C-termini of Smap 29 constitute distinct LPS-binding domains, the primary means by which these peptides recognize Gram-negative bacteria (FIGS. 7 & 8).

Activities of the peptide were evaluated towards *E. coli* ML-35P, *P. aeruginosa* MR 3007, *L. monocytogenes* EGD and MRSA ATCC 33591 (See Tables 15–17). Activity of the native peptide was determined to be indistinguisable from the synthetic version of Smap28 (FIGS. 9 and 10). Activity was concentration dependent but efficacy of the native and synthetic proteins was determined to be statistically the same.

TABLE 15

*E. coli* ML-35p, MIC(µg/ml) in underlays of low, normal and high salinity

| Seq. ID | Primary Structure | 0 mM NaCl | 100 mM NaCl | 175 mM NaCl |
|---|---|---|---|---|
| 2 | RGLRR LGRKI AHGVK KYGPT VLRII RIAG | 0.54 ± 0.15 | 0.35 ± 0.05 | 0.32 ± 0.08 |
| 3 | KI AHGVK KYGPT VLRII RIAG | 0.20 ± 0.09 | 6.21 ± 0.62 | >79.1 |
| 4 | LGRKI AHGVK KYGPT VLRII | 0.20 ± 0.08 | 21.97 ± 0.63 | >79.1 |
| 5 | RGLRR LGRKI AHGVK KYG | 0.44 ± 0.15 | 5.87 ± 0.52 | 58.6 ± 11.79 |
| 8 | KNLRR IIRKI IHIIK KYG | 0.45 ± 0.10 | 0.38 ± 0.02 | 0.41 ± 0.06 |
| 11 | LRR IIRKI IHIIK K-NH$_2$ | 0.63 ± 0.05 | 5.87 ± 0.04 | 49.2 ± 15.2 |
| 12 | LRR IIRKI IHIIK K | 0.68 ± 0.07 | 15.9 ± 5.0 | >79.1 |
| 13 | IRR IIRKI IHIIK K-NH$_2$ | n.t | n.t | n.t |
| 15 | LRR IIRKI IHIIK-NH$_2$ | 0.64 ± 0.15 | 2.24 ± 0.32 | 12.6 ± 2.8 |
| 17 | RR IIRKI IHIIK-NH$_2$ | 0.29 ± 0.06 | 17.6 ± 5.73 | >79.1 |
| 18 | GLRKR LRKFR NKIKE KLKKI GQKIQ GLLPK LAPRT DY | 2.8 | 1.5 | n.t. |
| 19 | GLRKR LRKFR NKIKE KLKKI G | 2.3 | 0.4 | n.t. |
| 20 | KR LRKFR NKIKE KLKKI G | 2.3 | 0.5 | n.t. |
| 21 | RKR LRKFR NKIKE KLKKI GQKI | 0.2 | 0.4 | n.t. |
| 22 | LRKFR NKIKE KLKKI GQKI | 0.1 | 1.7 | n.t. |
| 23 | LRKFR NKIKE KLKKI GQKIQ G | 0.2 | 0.7 | n.t. |
| 24 | RKFR NKIKE KLKKI G | 9.7 | 1.9 | n.t. |
| 25 | KIKE KLKKI GQKIQ G | 1.6 | >250 | n.t. |
| 26 | KIKE KLKKI GQKIQ GLL | 0.4 | 18.2 | n.t. |
| 27 | RGLRR LGRKI AHGVK KYGPT VLRII RIA-NH$_2$ | 0.37 ± 0.09 | 0.34 ± 0.02 | 0.42 ± 0.17 |
| 28 | KNLRR IIRKI IHIIK KYGPT ILRII RIIG-NH$_2$ | 0.16 ± 0.03 | 0.52 ± 0.12 | 0.58 ± 0.12 |

TABLE 16

*E. coli* ATCC 33780 (Serotype 0111) MIC (μg/mL) in underlays of low, normal and high salinity

| Seq. # | Primary Structure | 0 mM NaCl | 100 mM NaCl | 175 mM NaCl |
|---|---|---|---|---|
| 2 | RGLRR LGRKI AHGVK KYGPT VLRII RIAG | 0.46 ± 0.09 | 0.28 ± 0.01 | 0.26 ± |
| 3 | KI AHGVK KYGPT VLRII RIAG | 0.53 ± 0.24 | 6.80 ± 0.60 | 73.2 ± 5.84 |
| 4 | LGRKI AHGVK KYGPT VLRII | 0.82 ± 0.22 | 20.8 ± 1.46 | >79.1 |
| 5 | RGLRR LGRKI AHGVK KYG | 2.98 ± 1.39 | 9.74 ± 6.03 | 38.0 ± 20.5 |
| 27 | RGLRR LGRKI AHGVK KYGPT VLRII RIA-NH$_2$ | 0.61 ± 0.15 | 0.36 ± 0.04 | 0.36 ± 0.04 |

TABLE 17

*E. coli* DH-5α, MIC(μg/mL) in underlays of low, normal and high salinity

| Seq. ID | Primary Structure | 0 mM NaCl | 100 mM NaCl | 175 mM NaCl |
|---|---|---|---|---|
| 2 | RGLRR LGRKI AHGVK KYGPT VLRII RIAG | 0.55 ± 0.15 | 0.32 ± 0.04 | 0.31 ± 0.08 |
| 3 | KI AHGVK KYGPT VLRII RIAG | 0.42 ± 0.10 | 22.91 ± 12.01 | >79.1 |
| 4 | LGRKI AHGVK KYGPT VLRII | 0.76 ± 0.12 | 47.79 ± 20.40 | >79.1 |
| 5 | RGLRR LGRKI AHGVK KYG | 1.15 ± 0.16 | 15.63 ± 4.46 | 60.03 ± 13.2 |
| 8 | KNLRR IIRKI IHIIK KYG | 0.26 ± 0.05 | 0.31 ± 0.06 | 0.35 ± 0.09 |
| 11 | LRR IIRKI IHIIK K-NH$_2$ | 0.85 ± 0.04 | 1.91 ± 0.40 | 5.92 ± 1.02 |
| 12 | LRR IIRKI IHIIK K | 1.36 ± 0.19 | 4.93 ± 1.41 | 19.1 ± 5.0 |
| 13 | IRR IIRKI IHIIK K-NH$_2$ | n.t | n.t | n.t |
| 15 | LRR IIRKI IHIIK-NH$_2$ | 0.82 ± 0.12 | 1.84 ± 0.36 | 5.35 ± 1.87 |
| 17 | RR IIRKI IHIIK-NH$_2$ | 0.51 ± 0.09 | 6.19 ± 1.67 | 46.1 ± 16.1 |
| 18 | GLRKR LRKFR NKIKE KLKKI GQKIQ GLLPK LAPRT DY | 0.84 | 0.91 | n.t. |
| 27 | RGLRR LGRKI AHGVK KYGPT VLRII RIA-NH$_2$ | 0.47 ± 0.11 | 0.30 ± 0.04 | 0.37 ± 0.17 |
| 28 | KNLRR IIRKI IHIIK KYGPT ILRII RIIG-NH$_2$ | 0.0042 ± 0.0027 | 0.27 ± 0.05 | 0.40 ± 0.09 |

TABLE 18

*P. aeruginosa* MR-3007 MIC(μg/ml) in underlays of low, normal and high salinity

| Seq. # | Structure | 0 mM NaCl | 100 mM NaCl | 175 mM NaCl |
|---|---|---|---|---|
| 2 | RGLRR LGRKI AHGVK KYGPT VLRII RIAG | 0.60 ± 0.07 | 0.60 ± 0.05 | 0.50 ± 0.05 |
| 3 | KI AHGVK KYGPT VLRII RIAG | 0.61 ± 0.12 | 15.8 ± 0.62 | 30.1 ± 0.9 |
| 4 | LGRKI AHGVK KYGPT VLRII | 0.64 ± 0.16 | 44.5 ± 0.63 | >79.1 |
| 5 | RGLRR LGRKI AHGVK KYG | 1.14 ± 0.29 | 8.22 ± 0.52 | 13.2 ± 4.2 |
| 8 | KNLRR IIRKI IHIIK KYG | 0.67 ± 0.12 | 0.57 ± 0.02 | 0.59 ± 0.05 |
| 11 | LRR IIRKI IHIIK K-NH$_2$ | 0.92 ± 0.06 | 4.36 ± 0.04 | 20.1 ± 6.9 |
| 12 | LRR IIRKI IHIIK K | 0.98 ± 0.08 | 9.38 ± 5.0 | 46.3 ± 9.1 |
| 13 | IRR IIRKI IHIIK K-NH$_2$ | 0.84 ± 0.06 | 3.99 ± | 19.7 ± 2.2 |
| 15 | LRR IIRKI IHIIK-NH$_2$ | 0.96 ± 0.08 | 3.07 ± 0.32 | 9.14 ± 4.81 |
| 17 | RR IIRKI IHIIK-NH$_2$ | 0.72 ± 0.15 | 44.6 ± 5.73 | >79.1 |
| 18 | GLRKR LRKFR NKIKE KLKKI GQKIQ GLLPK LAPRT DY | 2.1 | 3.2 | n.t. |
| 19 | GLRKR LRKFR NKIKE KLKKI G | 0.7 | 0.9 | n.t. |
| 20 | KR LRKFR NKIKE KLKKI G | 2.9 | 23.5 | n.t. |
| 21 | RKR LRKFR NKIKE KLKKI GQKI | 0.2 | 1.6 | n.t. |
| 22 | LRKFR NKIKE KLKKI GQKI | 0.7 | 7.6 | n.t. |
| 23 | LRKFR NKIKE KLKKI GQKIQ G | 1.5 | 5.3 | n.t. |
| 24 | RKFR NKIKE KLKKI G | 5.1 | >250 | n.t. |
| 25 | KIKE KLKKI GQKIQ G | 8.7 | >250 | n.t. |
| 26 | KIKE KLKKI GQKIQ GLL | 1.0 | 26.7 | n.t. |
| 28 | KNLRR IIRKI IHIIK KYGPT ILRII RIIG-NH$_2$ | 0.34 ± 0.22 | 0.51 ± 0.04 | 0.49 ± 0.06 |

TABLE 19

*P. aeruginosa* PA-01 MIC(μg/mL) in underlays of low, normal and high salinity

| Seq. # | Structure | 0 mM NaCl | 100 mM NaCl | 175 mM NaCl |
|---|---|---|---|---|
| 2 | RGLRR LGRKI AHGVK KYGPT VLRII RIAG | 0.78 ± 0.01 | 0.59 ± 0.03 | 0.51 ± 0.03 |
| 3 | KI AHGVK KYGPT VLRII RIAG | 0.44 ± 0.06 | 13.6 ± 7.56 | 32.2 ± 0.7 |
| 4 | LGRKI AHGVK KYGPT VLRII | 0.47 ± 0.10 | 39.0 ± 20.1 | >79.1 |
| 5 | RGLRR LGRKI AHGVK KYG | 0.28 ± 0.04 | 1.72 ± 0.6 | 5.40 ± 1.25 |
| 8 | KNLRR IIRKI IHIIK KYG | 0.83 ± 0.05 | 0.70 ± 0.02 | 0.82 ± 0.05 |

TABLE 19-continued

*P. aeruginosa* PA-01 MIC(μg/mL) in underlays of low, normal and high salinity

| Seq. # | Structure | 0 mM NaCl | 100 mM NaCl | 175 mM NaCl |
| --- | --- | --- | --- | --- |
| 11 | LRR IIRKI IHIIK K-NH$_2$ | 0.96 ± 0.05 | 2.28 ± 1.02 | 6.51 ± 1.02 |
| 12 | LRR IIRKI IHIIK K | 0.98 ± 0.05 | 4.19 ± 1.63 | 11.9 ± 4.7 |
| 13 | IRR IIRKI IHIIK K-NH$_2$ | 1.03 ± 0.08 | 1.98 ± 0.74 | 7.45 ± 0.87 |
| 15 | LRR IIRKI IHIIK-NH$_2$ | 1.07 ± 0.19 | 4.86 ± 2.69 | 4.66 ± 1.57 |
| 17 | RR IIRKI IHIIK-NH$_2$ | 0.69 ± 0.08 | 7.09 ± 2.80 | 17.2 ± 4.6 |
| 18 | GLRKR LRKFR NKIKE KLKKI GQKIQ GLLPK LAPRT DY | 0.88 | 2.77 | n.t. |
| 28 | KNLRR IIRKI IHIIK KYGPT ILRII RIIG-NH$_2$ | 0.53 ± 0.14 | 0.70 ± 0.09 | 1.17 ± 0.23 |

TABLE 20

*B. cepacia* ATCC 25416 in underlays of low, normal and high salinity

| Seq. # | Structure | 0 mM NaCl | 100 mM NaCl | 175 mM NaCl |
| --- | --- | --- | --- | --- |
| 2 | RGLRR LGRKI AHGVK KYGPT VLRII RIAG | 19.7 | >250 | n.t. |
| 5 | RGLRR LGRKI AHGVK KYG | >250 | >250 | n.t. |
| 8 | KNLRR IIRKI IHIIK KYG | 20.2 | >250 | n.t. |
| 11 | LRR IIRKI IHIIK K-NH$_2$ | >79.1 | >250 | n.t. |
| 18 | GLRKR LRKFR NKIKE KLKKI GQKIQ GLLPK LAPRT DY | >79.1 | >250 | n.t. |
| 19 | GLRKR LRKFR NKIKE KLKKI G | >250 | >250 | n.t. |
| 20 | KR LRKFR NKIKE KLKKI G | >250 | >250 | n.t. |
| 21 | RKR LRKFR NKIKE KLKKI GQKI | >250 | >250 | n.t. |
| 22 | LRKFR NKIKE KLKKI GQKI | >250 | >250 | n.t. |
| 23 | LRKFR NKIKE KLKKI GQKIQ G | >250 | >250 | n.t. |
| 24 | RKFR NKIKE KLKKI G | >250 | >250 | n.t. |
| 25 | KIKE KLKKI GQKIQ G | >250 | >250 | n.t. |
| 26 | KIKE KLKKI GQKIQ GLL | >250 | >250 | n.t. |
| 28 | KNLRR IIRKI IHIIK KYGPT ILRII RIIG-NH$_2$ | 17.0 | >79.1 | n.t. |

TABLE 21

*N. gonorrhoeae*-done only at 100 mM NaCl

| Seq. # | Structure | FA 19 (serum-resistant) | F 62 (serum-sensitive) |
| --- | --- | --- | --- |
| 2 | RGLRR LGRKI AHGVK KYGPT VLRII RIAG | 0.2 | 0.3 |
| 5 | RGLRR LGRKI AHGVK KYG | 56.9 | 20.6 |
| 8 | KNLRR IIRKI IHIIK KYG | 0.2 | 0.5 |
| 11 | LRR IIRKI IHIIK K-NH$_2$ | 0.9 | 0.8 |
| 18 | GLRKR LRKFR NKIKE KLKKI GQKIQ GLLPK LAPRT DY | 0.6 | 0.7 |
| 19 | GLRKR LRKFR NKIKE KLKKI G | >79.1 | 0.6 |
| 20 | KR LRKFR NKIKE KLKKI G | >250 | >250 |
| 21 | RKR LRKFR NKIKE KLKKI GQKI | >250 | 22.0 |
| 22 | LRKFR NKIKE KLKKI GQKI | >250 | >79.1 |
| 23 | LRKFR NKIKE KLKKI GQKIQ G | >250 | >79.1 |
| 24 | RKFR NKIKE KLKKI G | >250 | >250 |
| 25 | KIKE KLKKI GQKIQ G | >250 | >79.1 |
| 26 | KIKE KLKKI GQKIQ GLL | >250 | >79.1 |
| 28 | KNLRR IIRKI IHIIK KYGPT ILRII RIIG-NH$_2$ | 0.1 | 0.1 |

TABLE 22

*S. aureus* 930918-3 MIC(μg/mL) in underlays of low, normal and high salinity

| Seq. # | Structure | 0 mM NaCl | 100 mM NaCl | 175 mM NaCl |
| --- | --- | --- | --- | --- |
| 2 | RGLRR LGRKI AHGVK KYGPT VLRII RIAG | 1.01 ± 0.20 | 0.82 ± 0.08 | 1.62 ± 0.35 |
| 3 | KI AHGVK KYGPT VLRII RIAG | 2.57 ± 0.23 | 26.7 ± 2.5 | >79.1 |
| 4 | LGRKI AHGVK KYGPT VLRII | 6.97 ± 0.59 | >79.1 | >79.1 |
| 5 | RGLRR LGRKI AHGVK KYG | 6.75 ± 0.51 | >79.1 | >79.1 |
| 8 | KNLRR IIRKI IHIIK KYG | 0.84 ± 0.14 | 0.79 ± 0.02 | 0.86 ± 0.06 |
| 11 | LRR IIRKI IHIIK K-NH$_2$ | 1.38 ± 0.21 | 4.70 ± 1.36 | 16.4 ± 5.1 |
| 12 | LRR IIRKI IHIIK K | 2.40 ± 0.17 | 65.4 ± 13.7 | 79.1 ± 0 |
| 13 | LRR IIRKI IHIIK K-NH$_2$ | 1.03 ± 0.03 | 2.01 ± 0.06 | 5.93 ± 1.12 |

TABLE 22-continued

*S. aureus* 930918-3 MIC(μg/mL) in underlays of low, normal and high salinity

| Seq. # | Structure | 0 mM NaCl | 100 mM NaCl | 175 mM NaCl |
|---|---|---|---|---|
| 15 | LRR IIRKI IHIIK-NH$_2$ | 1.32 ± 0.22 | 3.88 ± 0.93 | 6.39 ± 1.12 |
| 17 | RR IIRKI IHIIK-NH$_2$ | 2.29 ± 0.07 | >79.1 | >79.1 |
| 18 | GLRKR LRKFR NKIKE KLKKI GQKIQ GLLPK LAPRT DY | 1.8 | 2.8 | n.t. |
| 19 | GLRKR LRKFR NKIKE KLKKI G | 1.8 | 2.2 | n.t. |
| 20 | KR LRKFR NKIKE KLKKI G | 9.7 | 29.0 | n.t. |
| 21 | RKR LRKFR NKIKE KLKKI GQKI | 7.9 | >79.1 | n.t. |
| 22 | LRKFR NKIKE KLKKI GQKI | 6.0 | >79.1 | n.t. |
| 23 | LRKFR NKIKE KLKKI GQKIQ G | 16.3 | >250 | n.t. |
| 24 | RKFR NKIKE KLKKI G | 19.5 | >250 | n.t. |
| 25 | KIKE KLKKI GQKIQ G | >250 | >250 | n.t. |
| 26 | KIKE KLKKI GQKIQ GLL | >250 | >250 | n.t. |
| 28 | KNLRR IIRKI IHIIK KYGPT ILRII RIIG-NH$_2$ | 0.55 ± 0.17 | 0.82 ± 0.04 | 1.14 ± 0.23 |

TABLE 23

MRSA ATCC 33591 MIC(μg/mL) in underlays of low, normal and high salinity

| Seq. # | Primary Structure | 0 mM NaCl | 100 mM NaCl | 175 mM NaCl |
|---|---|---|---|---|
| 2 | RGLRR LGRKI AHGVK KYGPT VLRII RIAG | 0.77 ± 0.08 | 0.90 ± 0.17 | 1.34 ± 0.23 |
| 3 | KI AHGVK KYGPT VLRII RIAG | 2.53 ± 0.07 | >79.1 | >79.1 |
| 4 | LGRKI AHGVK KYGPT VLRII | 7.03 ± 0.66 | >79.1 | >79.1 |
| 5 | RGLRR LGRKI AHGVK KYG | 5.28 ± 0.49 | >79.1 | >79.1 |
| 8 | KNLRR IIRKI IHIIK KYG | 0.77 ± 0.04 | 0.75 ± 0.06 | 0.89 ± 0.05 |
| 11 | LRR IIRKI IHIIK K-NH$_2$ | 4.42 ± 1.73 | 23.6 ± 1.6 | >79.1 |
| 12 | LRR IIRKI IHIIK K | 11.0 ± 3.96 | >79.1 | >79.1 |
| 13 | IRR IIRKI IHIIK K-NH$_2$ | 2.39 ± 0.07 | 21.6 ± 0.3 | >79.1 |
| 15 | LRR IIRKI IHIIK-NH$_2$ | 2.49 ± 0.27 | 24.7 ± 2.5 | 65.8 ± 13.3 |
| 17 | RR IIRKI IHIIK-NH$_2$ | 11.9 ± 4.7 | >79.1 | >79.1 |
| 18 | GLRKR LRKFR NKIKE KLKKI GQKIQ GLLPK LAPRT DY | 8.2 | 2.8 | n.t. |
| 19 | GLRKR LRKFR NKIKE KLKKI G | 19.4 | 2.2 | n.t. |
| 20 | KR LRKFR NKIKE KLKKI G | 14.9 | 29.0 | n.t. |
| 21 | RKR LRKFR NKIKE KLKKI GQKI | 8.1 | >79.1 | n.t. |
| 22 | LRKFR NKIKE KLKKI GQKI | 4.5 | >79.1 | n.t. |
| 23 | LRKFR NKIKE KLKKI GQKIQ G | 10.3 | >250 | n.t. |
| 24 | RKFR NKIKE KLKKI G | >250 | >250 | n.t. |
| 25 | KIKE KLKKI GQKIQ G | >250 | >250 | n.t. |
| 26 | KIKE KLKKI GQKIQ GLL | >250 | >250 | n.t. |
| 28 | KNLRR IIRKI IHIIK KYGPT ILRII RIIG-NH$_2$ | 0.32 ± 0.04 | 0.81 ± 0.07 | 1.57 ± 0.30 |

TABLE 24

*L. monocytogenes* in underlays of low, normal and high salinity

| Seq. # | Structure | 0 mM NaCl | 100 mM NaCl | 175 mM NaCl |
|---|---|---|---|---|
| 2 | RGLRR LGRKI AHGVK KYGPT VLRII RIAG | 0.5 | 0.4 | n.t. |
| 5 | RGLRR LGRKI AHGVK KYG | 1.0 | 9.7 | n.t. |
| 8 | KNLRR IIRKI IHIIK KYG | 2.1 | 0.7 | n.t. |
| 11 | LRR IIRKI IHIIK K-NH$_2$ | 0.7 | 0.5 | n.t. |
| 18 | GLRKR LRKFR NKIKE KLKKI GQKIQ GLLPK LAPRT DY | 0.6 | 0.7 | n.t. |
| 19 | GLRKR LRKFR NKIKE KLKKI G | 0.3 | 0.5 | n.t. |
| 20 | KR LRKFR NKIKE KLKKI G | 2.3 | >250 | n.t. |
| 21 | RKR LRKFR NKIKE KLKKI GQKI | 7.0 | 30.3 | n.t. |
| 22 | LRKFR NKIKE KLKKI GQKI | 5.9 | >79.1 | n.t. |
| 23 | LRKFR NKIKE KLKKI GQKIQ G | 5.5 | >79.1 | n.t. |
| 24 | RKFR NKIKE KLKKI G | 24.1 | >250 | n.t. |
| 25 | KIKE KLKKI GQKIQ G | >250 | >250 | n.t. |
| 26 | KIKE KLKKI GQKIQ GLL | 5.7 | >79.1 | n.t. |
| 28 | KNLRR IIRKI IHIIK KYGPT ILRII RIIG-NH$_2$ | 0.4 | 0.5 | n.t. |

All of the COMPOSITIONS and/or METHODS disclosed and claimed herein can be made and executed without undue experimentation in light of the present disclosure. While the compositions and methods of this invention have been described in terms of preferred embodiments, it will be apparent to those of skill in the art that variations may be applied to the COMPOSITIONS and/or METHODS and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Agerberth et al., *Proc. Nat'l Acad. Sci. USA*, 92:195–199, 1995.
Bagella et al., *FEBS Lett.*, 376:225–228, 1995.
Baichwal and Sugden, In: *Gene Transfer*, Kucherlapati R, ed., New York, Plenum Press, 117–148, 1986.
Bals et al., *J Clin. Invest.*, 102:874–880, 1998.
Bals et al., "The peptide antibiotic LL-37/hCAP-18 is expressed in epithelia of the human lung where it has broad antimicrobial activity at the airway surface," *Proc. Nat'l Acad. Sci. USA*, 95:9541–9546, 1998.
Bangham et al., *J. Mol. Biol.*, 13: 238–252, 1965.
Bennik et al., "A novel bacteriocin with a YGNGV motif from vegetable-associated *Enterococcus mundtii*: full characterization and interaction with target organisms," *Biochim Biophys Acta*, 1373:47–58, 1998.
Benvenisty and Neshif, *Proc. Nat'l Acad. Sci. USA*, 83:9551–9555, 1986.
Berklman et al., *J Infect Dis.*, 170(2):272–7, 1994.
Boman, "Peptide antibiotics and their role in innate immunity," *Annu. Rev. Immunol.*, 13:61–92, 1995.
Boman, *Annu. Rev. Immunol.*, 13, 61–92, 1995.
Brasseur et al., *Trends in Biochem Soc.*, 22:167–71, 1997.
Capaldi et al., *Biochem Biophys Res Commun*, 74(2):425–33, 1977.
Chang et al., *Hepatology*, 14:124A, 1991.
Chen and Okayama, *Mol. Cell Biol.*, 7:2745–2752, 1987.
Chen et al., *FEBS Lett.*, 370:46–52, 1995.
Cleeland and Squires, In. *Lorian, Antibiotics in Laboratory Medicine*, Satterfield (Ed), Williams & Wilkins, Philadelphia, 1991.
Coffin, In: Fields BN, Knipe DM, ed. *Virology.* New York: Raven Press, pp. 1437–1500, 1990.
Couch et al., *Am. Rev. Resp. Dis.*, 88:394–403, 1963.
Coupar et al., *Gene*, 68:1–10, 1988.
Davies, *FEMS Microbiology Reviews*, 39:363–371, 1986.
Deamer and Uster, "Liposome Preparation: Methods and Mechanisms," In. *Liposomes*, M. Ostro (Ed.), 1983
Dubensky et al., *Proc. Nat'l Acad. Sci. USA*, 81:7529–7533, 1984.
Eisenberg, D. et al. *J Cell Biochem* 31: 11–7, 1986.8
Epand et al., *Biopolymers*, 37:319–338, 1995.
EPO 0273085

Fechheimer et al., *Proc. Nat'l. Acad. Sci. USA*, 84:8463–8467, 1987.
Ferkol et al., *FASEB J.*, 7:1081–1091, 1993.
Frackman et al., *J. Bacteriol.*, 172:5767–5773, 1990.
Fraley et al., *Proc. Nat'l Acad. Sci. USA*, 76:3348–3352, 1979.
Freshner, In: *Animal Cell Culture: a Practical Approach* Second Edition, Oxford/New York, IRL Press, Oxford University Press, 1992.
Friedmann, *Science*, 244:1275–1281, 1989.
Frohm Nilsson et al., *Infect Immun*, 67(5):2561–6, 1999.
Gallo et al., *J. Biol. Chem.*, 272:13088–13093, 1997.
Gallo et al., *J Invest Dermatol.*, 111(5):739–43, 1998.
Ganz and Lehrer, *Pharmac. Ther.*, 66:191–205, 1995.
Ganz and Lehrer, *Current Opinions Immun,*. 10:41, 1998.
Ghosh and Bachhawat, In: Wu G. and C. Wu (eds.) Liver diseases, targeted diagnosis and therapy using specific receptors and ligands, New York: Marcel Dekker, pp. 87–104, 1991.
Ghosh-Choudhury et al., *EMBO J*, 6:1733–1739, 1987.
Goldman et al., *Cell*, 88:553–560, 1997.
Gomez-Foix et al., *J. Biol. Chem.*, 267:25129–25134, 1992.
Gopal, *Mol. Cell Biol.*, 5:1188–1190, 1985.
Graham and Prevec, *Biotechnology*, 20:363–390, 1992.
Graham and Prevec, In: E. J. Murray (ed.), *Methods in Molecular Biology. Gene Transfer and Expression Protocol*, Clifton, N.J.: Humana Press, 7:109–128, 1991.
Graham and Van Der Eb, *Virology*, 52:456–467, 1973.
Graham et al., *J. Gen. Virol.*, 36:59–72, 1977.
Gregoriadis (ed.), In. *Drug Carriers in Biology and Medicine*, pp 287–341, 1979.
Grunhaus and Horwitz, *Seminar in Virology*, 3:237–252, 1992.
Hancock and Lehrer, 16:82–88, 1998.
Harland and Weintraub, *J. Cell Biol.*, 101:1094–1099, 1985.
Hernonat and Muzycska, *Proc. Nat'l Acad. Sci. USA*, 81:6466–6470, 1984.
Hersdorffer et al., *DNA Cell Biol.*, 9:713–723, 1990.
Herz and Gerard, Proc. Nat'l Acad. Sci. USA, 90:2812–2816, 1993.
Hirata, et al., *Infect. Immun.* 62 (4), 1421–1426 (1994)
Horwich, et al., *J. Virol*, 64:642–650, 1990.
Huttner et al., *Gene*, 206:85–91, 1998.
Hwang et al., *Biochem Cell Biol*, 76(2–3):235–46, 1998.
Inouye et al., *Nucleic Acids Res.*, 13:3101–3109, 1985.
Johansson et al., *J. Biol. Chem,*. 273:3718–3724, 1998.
Jones and Shenk, *Cell*, 13:181–188, 1978.
Kaneda, *J Biol Chem,*. 264(21): 12126–9, 1989.
Karlsson et al., *EMBO J*, 5:2377–2385, 1986.
Kato et al., *J. Biochem. Tokyo*, 101:207–215, 1987.
Klaassen, In: *The Pharmacological Basis of Therapeutics*, Goodman & Gilman, Eds., Pergamon Press, 8th Ed., pp. 49–61, 1990.
Klein et al., *Nature*, 327:70–73, 1987.
Kovach et al., *Gene*, 166:175–176, 1995.
Kyte J., Doolittle R. F., *J Mol Biol*, 157(1):105–32, 1982.
Larrick et al., *Antimicrob. Agents Chemother.*, 37:2534–2539, 1993.
Larrick et al*Biochem. Biophys. Res. Commun.*, 179:170–175, 1991.
Larrick et al., *Infect. Immun.*, 63:1291–1297, 1995.
Le Gal La Salle et al., *Science*, 259:988–990, 1993.
Lehrer et al., *Annu. Rev. Immuniol.*, 11:105–128, 1993.
Lehrer et al., J. Immunol. Methods, 137:167–173.
Levrero et al., *Gene*, 101: 195–202, 1991.

Lorian, In: *Antibiotics in Laboratory Medicine*, Satterfield (Ed), Williams & Wilkins, Philadelphia, pp. 558–559;718, 1991.
Luo and Baldwin, *Biochemistry*, 36: 8413–21, 1997.
Macejak and Sarnow, *Nature*, 353:90–94, 1991.
Mahoney et al., *FEBS Lett*, 377:519–522, 1995.
Mahoney et al., *FEBS Letters*, 377, 319–322, 1995.
Maloy and Kari, *Biopolymers*, 37:105–122, 1995.
Markowitz et al., *J. Virol.*, 62:1120–1124, 1988.
Martin et al., *Leuko. Biol.*, 58:128–136, 1995.
Mason et al., *Antimicrob. Agents Chemother.*, 41:624–629, 1997.
Mulligan, *Science*, 260:926–932, 1993.
Nicolas and Rubenstein, In: *Vectors: A survey of molecular cloning vectors and their uses*, Rodriguez and Denhardt (eds.), Stoneham: Butterworth, pp. 494–513, 1988.
Nicolau and Sene, *Biochem. Biophys. Acta*, 721:185–190, 1982.
Nicolau et al., *Methods Enzymol.*, 149:157–176, 1987.
Oren et al., *Biopolymers*, 47(6):451–63, 1998.
Ostreicher, *NY State Dent. J*, 60(3):47–49, 1994.
Paskind et al., *Virology*, 67:242–248, 1975.
Pelletier and Sonenberg, *Nature*, 334:320–325, 1988.
Perales et al, *Proc. Nat'l Acad. Sci.*, 91:4086–4090, 1994.
Perez-Mendez et al., *Eur. J. Biochem,.* 256:570–579, 1998.
Popsueva et al., *FEBS Lett.*, 391:5–8, 1996.
Porter et al., *Infect. Immun,.* 65:2396–2401, 1997.
Potter et al., *Proc. Nat'l Acad. Sci. USA*, 81:7161–7165, 1984. Publications, Bern, Switzerland, pp. 555–67, 1981.
Racher et al., *Biotechnology Techniques*, 9:169–174, 1995.
Ragot et al., *Nature*, 361:647–650, 1993.
Reese and Betts, In: *A Practical Approach to Infectious Diseases*, (3rd ed.), Boston, Little Brown, 1991.
Renan, *Radiother. Oncol.*, 19:197–218, 1990.
Rich et al., *Hum. Gene Ther.*, 4:461–476, 1993.
Ridgeway, In: Rodriguez RL, Denhardt DT, ed. *Vectors. A survey of molecular cloning vectors and their uses*, Stoneham: Butterworth, pp. 467–492, 1988.
Rippe et al., *Mol. Cell Biol.*, 10:689–695, 1990.
Rosenfeld et al., *Cell*, 68:143–155, 1992.
Rosenfeld et al., *Science*, 252:431–434, 1991.
Roux et al., *Proc. Nat'l Acad. Sci. USA*, 86:9079–9083, 1989.
Russel et al., *Infect Immun*, 64(5): 1565–8, 1996.
Selsted et al., "Purification and antibacterial activity of antimicrobial peptides of rabbit granulocytes," *Infect. Immun.*, 45:150–154, 1984.
Sheppard et al., *Journal of Chemical Society*, p. 538, 1981.
Singh et al., *PNAS*, 95:14961–5, 1998.
Stratford-Perricaudet and Perricaudet, In: *Human Gene Transfer*, Eds, O. Cohen-Haguenauer and M. Boiron, Editions John Libbey Eurotext, France, pp. 51–61, 1991.
Stratford-Perricaudet et al., *Hum. Gene Ther.*, 1:241–256, 1990.
Szoka and Papahadjopoulos, *Proc. Nat'l Acad. Sci. USA*, 75: 4194–4198, 1978.
Temin, In: *Gene Transfer*, Kucherlapati (ed.), New York: Plenum Press, pp. 149–188, 1986.
Top et al., *J. Infect. Dis.*, 124:155–160, 1971.
Tossi et al., *FEBS Lett.*, 339:108–112, 1994.
Travis et al., *Am. J. Resp. Pul. Mol. Biol.* 20:872–9, 1999.
Travis, J., *Science*, 264(5157):360–2, 1994.
Tur-Kaspa et al., *Mol. Cell Biol.*, 6:716–718, 1986.
Turner et al., "Activities of LL-37, a cathelin-associated antimicrobial peptide of human neutrophils," *Antimicrob Agents Chemother*, 42:2206–2214, 1998.
U.S. Pat. No. 4,554,101
Valore et al., 101:1633–1642, 1998.
Varmus et al., *Cell*, 25:23–36, 1981.
Wong et al., *Gene*, 10:87–94, 1980.
Wu & Wu, *Biochemistry*, 27:887–892, 1988.
Wu & Wu, *J. Biol. Chem.*, 262:4429–4432, 1987.
Wu and Wu, *Adv. Drug Delivery Rev.*, 12:159–167, 1993.
Yang et al., *Proc. Nat'l Acad. Sci USA*, 87:9568–9572, 1990
Zak and Sande, In: *Action of Antibiotics in Patients*, Sabath, Ed., Hans Huber
Zanetti et al., *FEBS Lett.*, 374:1–5, 1995.
Zanetti et al., *Ann. NY Acad. Sci.* 832:147–62, 1997.
Zelenin et al., *FEBS Lett.*, 280:94–96, 1991.

---

What is claimed is:

1. An isolated antimicrobial peptide of 12–37 residues, the peptide comprising one of the amino acid sequences selected from the group consisting of:
KNLRRIIRKIIHIIKKYG-NH$_2$ (SEQ ID NO: 1),
KNIRRIIRKIIHIIKKYG-NH$_2$ (SEQ ID NO: 6),
KNIRRIIRKIIHIIKKYG (SEQ ID NO: 7),
KNLRRIIRKIIHIIKKYG (SEQ ID NO: 8),
NLRRIIRKIIHIIKKY (SEQ ID NO 9),
NIRRIIRKIIHIIKKY (SEQ ID NO: 10),
LRRIIRKIIHIIKK-NH$_2$ (SEQ ID NO: 11),
LRRIIRKIIHIIKK (SEQ ID NO: 12),
IRRIIRKIIHIIKK-NH$_2$ (SEQ ID NO: 13),
IRRIIRKIIHIIKK (SEQ ID NO: 14),
LRRIIRKIIHIIK-NH$_2$ (SEQ ID NO: 15),
RRIIRKIIHIIKK-NH$_2$ (SEQ ID NO: 16),
RRIIRKIIHIIK-NH$_2$ (SEQ ID NO: 17),
RKRLRKFRNKIKEKLKKIGQKI (SEQ ID NO: 21),
LRKFRNKIKEKLKKIGQKI (SEQ ID NO: 22),
LRKFRNKIKEKLKKIGQKIQG (SEQ ID NO: 23),
KIKEKLKKIGQKIQG (SEQ ID NO: 25),
KIKEKLKKIGQKIQGLL (SEQ ID NO: 26), and
KNLRRIIRKIIHIIKKYGPTILRIIRIIG-NH$_2$ (SEQ ID NO: 28).

2. A pharmaceutical composition comprising an antimicrobial peptide of 12 to 37 residues, the peptide comprising one of the amino acid sequences selected from the group consisting of:
KNLRRIIRKIIHIIKKYG-NH$_2$ (SEQ ID NO: 1),
KNIRRIIRKIIHIIKKYG-NH$_2$ (SEQ ID NO: 6),
KNIRRIIRKIIHIIKKYG (SEQ ID NO: 7),
KNLRRIIRKIIHIIKKYG (SEQ ID NO: 8),
NLRRIIRKIIHIIKKY (SEQ ID NO 9),
NIRRIIRKIIHIIKKY (SEQ ID NO: 10),
LRRIIRKIIHIIKK-NH$_2$ (SEQ ID NO: 11),
LRRIIRKIIHIIKK (SEQ ID NO: 12),
IRRIIRKIIHIIKK-NH$_2$ (SEQ ID NO: 13),
IRRIIRKIIHIIKK (SEQ ID NO: 14),
LRRIIRKIIHIIK-NH$_2$ (SEQ ID NO: 15),
RRIIRKIIHIIKK-NH$_2$ (SEQ ID NO: 16),
RRIIRKIIHIIK-NH$_2$ (SEQ ID NO: 17),
RKRLRKFRNKIKEKLKKIGQKI (SEQ ID NO: 21),
LRKFRNKIKEKLKKIGQKI (SEQ ID NO: 22),
LRKFRNKIKEKLKKIGQKIQG (SEQ ID NO: 23),
KIKEKLKKIGQKIQG (SEQ ID NO: 25),
KIKEKLKKIGQKIQGLL (SEQ ID NO: 26), and
KNLRRIIRKIIHIIKKYGPTILRIIRIIG-NH$_2$ (SEQ ID NO: 28), formulated in a pharmaceutically acceptable carrier.

3. An isolated peptide consisting of the sequence KNLRRIIRKIIHIIKKYG-NH$_2$ (SEQ ID NO: 1).

4. The antimicrobial peptide of claim 1, consisting of the sequence KNIRRIIRKIIHIIKKYG-NH$_2$ (SEQ ID NO: 6).

5. The antimicrobial peptide of claim 1, consisting of the sequence KNIRRIIRKIIHIIKKYG (SEQ ID NO: 7).

6. The antimicrobial peptide of claim 1, consisting of the sequence KNLRRIIRKIIHIIKKYG (SEQ ID NO: 8).

7. The antimicrobial peptide of claim 1, consisting of the sequence NLRRIIRKIIHIIKKY (SEQ ID NO 9).

8. The antimicrobial peptide of claim 1, consisting of the sequence NIRRIIRKIIHIIKKY (SEQ ID NO: 10).

9. The antimicrobial peptide of claim 1, consisting of the sequence LRRIIRKIIHIIKK-NH$_2$ (SEQ ID NO: 11).

10. The antimicrobial peptide of claim 1, consisting of the sequence LRRIIRKIIHIIKK (SEQ ID NO: 12).

11. The antimicrobial peptide of claim 1, consisting of the sequence IRRIIRKIIHIIKK-NH$_2$ (SEQ ID NO: 13).

12. The antimicrobial peptide of claim 1, consisting of the sequence IRRIIRKIIHIIKK (SEQ ID NO: 14).

13. The antimicrobial peptide of claim 1, consisting of the sequence LRRIIRKIIHIIK-NH$_2$ (SEQ ID NO: 15).

14. The antimicrobial peptide of claim 1, consisting of the sequence RRIIRKIIHIIKK-NH$_2$ (SEQ ID NO: 16).

15. The antimicrobial peptide of claim 1, consisting of the sequence RRIIRKIIHIIK-NH$_2$ (SEQ ID NO: 17).

16. The antimicrobial peptide of claim 1, consisting of the sequence RKRLRKFRNKIKEKLKKIGQKI (SEQ ID NO: 21).

17. The antimicrobial peptide of claim 1, consisting of the sequence LRKFRNKIKEKLKKIGQKI (SEQ ID NO: 22).

18. The antimicrobial peptide of claim 1, consisting of the sequence LRKFRNKIKEKLKKIGQKIQG (SEQ ID NO: 23).

19. The antimicrobial peptide of claim 1, consisting of the sequence KIKEKLKKIGQKIQG (SEQ ID NO: 25).

20. The antimicrobial peptide of claim 1, consisting of the sequence KIKEKLKKIGQKIQGLL (SEQ ID NO: 26).

21. The antimicrobial peptide of claim 1, consisting of the sequence KNLRRIIRKIIHIIKKYGPTILRIIRIIG-NH$_2$ (SEQ ID NO: 28).

* * * * *